(12) United States Patent
Binkert et al.

(10) Patent No.: US 8,067,419 B2
(45) Date of Patent: Nov. 29, 2011

(54) PIPERAZINES AS ANTIMALARIAL AGENTS

(75) Inventors: Christoph Binkert, Basel (CH);
Christoph Boss, Allschwil (CH);
Olivier Corminboeuf, Allschwil (CH);
Corinna Grisostomi, Allschwil (CH);
Solange Meyer, Schlierbach (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 527 days.

(21) Appl. No.: 12/090,816

(22) PCT Filed: Oct. 20, 2006

(86) PCT No.: PCT/IB2006/053868
§ 371 (c)(1),
(2), (4) Date: Apr. 18, 2008

(87) PCT Pub. No.: WO2007/046075
PCT Pub. Date: Apr. 26, 2007

(65) Prior Publication Data
US 2008/0234272 A1   Sep. 25, 2008

(30) Foreign Application Priority Data

Oct. 21, 2005   (WO) .................. PCT/IB2005/053457

(51) Int. Cl.
*A61K 31/4965*   (2006.01)
*C07D 487/00*   (2006.01)
(52) U.S. Cl. .................................. 514/255.01; 544/351
(58) Field of Classification Search .................. None
See application file for complete search history.

(56) References Cited

FOREIGN PATENT DOCUMENTS

| EP | 0 407 200 A1 | 1/1991 |
|---|---|---|
| EP | 0407200 A1 * | 9/1991 |
| JP | 03 127732 A | 5/1991 |
| WO | WO-00/15657 A1 | 3/2000 |
| WO | WO-02/098856 A2 | 12/2002 |
| WO | WO-2004/032874 A2 | 4/2004 |
| WO | WO-2005/013909 A1 | 2/2005 |
| WO | WO-2005/058822 A1 | 6/2005 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Chawla et. al. Current Research & Information on Pharmaceutical Science, 2004, 5(1), p. 9, col. 2, para.1).*
Newman et. al.; Drug Discovery Today; 2003, 8(19) p. 898, col. 2, Para.3.*
http://www.thefreedictionary.com/prevent, last accessed on Aug. 26, 2010.*
Gould, Philip L.; "Salt Selection for basic drugs"; *International Journal of Pharmaceutics*, 33 (1986), pp. 201-217.
Gibson, Mark, Editor, Pharmaceutical Preformulation and Formulation, IHS Health Group, Englewood, CO, USA, 2001.
Database Chemcats, Chemical Abstracts Service, Columbus, OH, USA; XP002420714; Order No. CGX-3221820. Apr. 15, 2005.
Database Chemcats, Chemical Abstracts Service, Columbus, OH, USA; XP002420715; Order No. T5569369, T5467386. Jan. 24, 2006.
Gennaro, Alfonso R., Editor, "Remington: the Science and Practice of Pharmacy", 20th Edition, Philadelphia College of Pharmacy and Science. Table of Contents, 2003.

* cited by examiner

*Primary Examiner* — Jeffrey Murray
(74) *Attorney, Agent, or Firm* — Hoxie & Associates LLC

(57) ABSTRACT

The invention relates to novel piperazine derivatives and their use as active ingredients in the preparation of pharmaceutical compositions. The invention also concerns related aspects including pharmaceutical compositions containing one or more of those compounds and their use as medicaments for the treatment or prevention of protozoal infections, especially malaria.

31 Claims, No Drawings

PIPERAZINES AS ANTIMALARIAL AGENTS

The invention relates to novel compounds of the formula I. The invention also concerns related aspects including processes for the preparation of the compounds, pharmaceutical compositions containing one or more compounds of the formula I and especially their use as medicaments to treat or prevent malaria infections or to treat or prevent other protozoal diseases like sleeping sickness, Chagas disease, amebiasis, giardiasis, trichomoniasis, toxoplasmosis, leishmaniasis etc.

BACKGROUND OF THE INVENTION

Numerous serious diseases affecting humans as well as domestic and livestock animal are caused by protozoal organisms such as kinetoplastida, apicomplexa, anaerobic protozoa, *microsporidia* and *plasmodium*. The clinically most relevant of these diseases is malaria.

Malaria is one of the most serious and complex health problems affecting humanity in the 21$^{st}$ century. The disease affects about 300 million people worldwide, killing 1 to 1.5 million people every year. Malaria is an infectious disease caused by four species of the protozoan parasite *plasmodium, P. falciparum* being the most severe of the four. All attempts to develop vaccines against *P. falciparum* have failed so far. Therefore, therapies and preventive measures against malaria are confined to drugs. Various classes of antimalarial drugs exist. The most widely used are the quinoline antimalarials, e.g. chloroquine which has been an especially effective drug for both prophylaxis and therapy. However, resistance to many of the currently available antimalarial drugs is spreading rapidly, threatening people in areas where malaria is endemic. Reports of multi-drug resistant strains of malaria parasites render the search for new antimalarial agents especially urgent.

*P. falciparum* enters the human body by way of bites of the female anophelino mosquito (it may also be transmitted by blood transfusion from asymptotic donors; almost all infected blood components including red cells, platelet concentrates, white cells, cryoprecipitates and fresh plasma can transmit malaria). The *plasmodium* parasite initially populates the liver, and during later stages of the infectious cycle reproduces in red blood cells. During this stage, the parasite degrades hemoglobin and uses the degradation products as nutrients for growth. The limitations of the current antiprotozoal chemotherapeutic arsenal underscore the need for new drugs in this therapeutic area. The present invention relates to the identification of novel low molecular weight, non-peptidic, non-quinoline compounds of formula I which are useful in the treatment and/or prevention of protozoal infections, especially in the treatment and/or prevention of malaria, in particular *plasmodium falciparum* malaria.

DETAILED DESCRIPTION OF THE INVENTION

The present invention relates to novel compounds of the formula I:

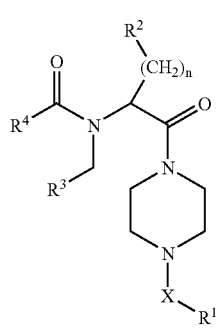

formula I wherein
X represents —(CH$_2$)$_{0-2}$— or —C(=O)—;
n represents the integer 0, 1 or 2;
R$^1$ represents hydrogen; alkyl; cycloalkyl; ethoxy-carbonyl; hydroxy-ethyl; benzo[1,3]dioxolyl; aryl that can be mono-, di-, tri-, or tetra-substituted, wherein the substituents are independently selected from halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —CF$_3$, —OCF$_3$, hydroxy, alkoxy-carbonyl, and carboxyl; furanyl that can be mono-, or di-substituted, wherein the substituents are independently selected from methyl, hydroxy-methyl, and bromine; thienyl that can be mono-substituted with methyl or chlorine; pyrimidinyl that can be mono-substituted with alkyl, halogen, cyclopropyl, CH$_3$—S—, or methylsulfonyl or that can be mono- or di-substituted with methoxy; pyridazinyl; benzothienyl; benzofuranyl; quinolinyl; isoquinolinyl; benzhydryl, wherein both phenyl rings can be mono- or di-substituted, wherein the substituents are independently selected from halogen, alkyl, alkoxy, —CF$_3$, —OCF$_3$, hydroxy, cyano, alkoxy-carbonyl, and alkyl-carbonyl; imidazolyl optionally mono-substituted with alkyl; thiazolyl; or oxazolyl;
R$^2$ represents hydrogen; alkyl; indolyl; carboxyl; alkoxy-carbonyl; amino-carbonyl; imidazolyl optionally mono-substituted with alkyl; cycloalkyl; aryl that can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —CF$_3$, —OCF$_3$, hydroxy, alkoxy-carbonyl, and carboxyl; benzothienyl; thiazolyl; or thienyl;
R$^3$ represents hydrogen; alkyl; cycloalkyl; formyl; acetyl; ethoxy-carbonyl; hydroxy-ethyl; benzo[1,3]dioxolyl; indolyl; pyridyl that can be mono-, di-, or tri-substituted, wherein the substituents are independently selected from: halogen, alkyl, alkoxy, alkoxy-alkoxy, —CF$_3$, —OCF$_3$, hydroxy, alkoxy-carbonyl, carboxyl, hydroxy-C$_{1-5}$-alkyl, 2,3-dihydroxypropyl, di-(hydroxy-C$_{1-5}$-alkyl)-C$_{1-5}$-alkyl, —CH$_2$—(CH$_2$)$_k$—NR$^{31}$R$^{32}$, (azetidine-3-carboxylic acid)-1-yl-methyl, (azetidine-3-carboxylic acid C$_{1-5}$-alkylester)-1-yl-methyl, 2-[(azetidine-3-carboxylic acid)-1-yl]-ethyl, 2-[(azetidine-3-carboxylic acid C$_{1-5}$-alkylester)-1-yl]-ethyl, 3-[(azetidine-3-carboxylic acid)-1-yl]-propyl, 3-[(azetidine-3-carboxylic acid C$_{1-5}$-alkylester)-1-yl]-propyl, (pyrrolidine-3-carboxylic acid)-1-yl-methyl, (pyrrolidine-3-carboxylic acid C$_{1-5}$-alkylester)-1-yl-methyl, (pyrrolidine-2-carboxylic acid)-1-yl-methyl, (pyrrolidine-2-carboxylic acid C$_{1-5}$-alkylester)-1-yl-methyl, 2-[(pyrrolidine-3-carboxylic acid)-1-yl]-ethyl, 2-[(pyrrolidine-3-carboxylic acid C$_{1-5}$-alkylester)-1-yl]-ethyl, 2-[(pyrrolidine-2-carboxylic acid)-1-yl]-ethyl, 2-[(pyrrolidine-2-carboxylic acid C$_{1-5}$-alkylester)-1-yl]-ethyl, 3-[(pyrrolidine-3-carboxylic acid)-1-yl]-propyl, 3-[(pyrrolidine-3-carboxylic acid C$_{1-5}$-alkylester)-1-yl]-propyl, 3-[(pyrrolidine-2-carboxylic acid)-1-yl]-propyl, 3-[(pyrrolidine-2-carboxylic acid C$_{1-5}$-alkylester)-1-yl]-propyl, —CH$_2$—(CH$_2$)$_p$—CONR$^{31}$R$^{32}$, —CO—NHR$^{31}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3- propionyl, 1-(3-carboxy-pyrrolidinyl)-3-propionyl, —$(CH_2)_pCH(OH)$—$CH_2$—$NR^{31}R^{32}$, hydroxy-$C_{2-5}$-alkoxy, di-(hydroxy-$C_{1-5}$-alkyl)-$C_{1-5}$-alkoxy, 2,3-dihydroxypropoxy, 2-hydroxy-3-methoxy-propoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, 1-(3-carboxy-azetidinyl)-1-oxo-2-ethoxy, 1-(pyrrolidine-2-carboxylic acid)-1-yl-1-oxo-2-ethoxy, 1-(pyrrolidine-3-carboxylic acid)-1-yl-1-oxo-2-ethoxy, 3-carbamoyl-propoxy, 3-($C_{1-5}$-alkylcarbamoyl) propoxy, 3-(2-hydroxyethylcarbamoyl)propoxy, —$OCH_2$—$CH(OH)$—$CH_2$—$NR^{31}R^{32}$ 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —$R^{31}R^{32}$, —$CH_2$—$(CH_2)_k$—$NHSO_2R^{33}$, —$(CH_2)_pCH(OH)$—$CH_2$—$NHSO_2R^{33}$, —$OCH_2$—$(CH_2)_m$—$NHSO_2R^{33}$, —$OCH_2$—$CH(OH)$—$CH_2$—$NHSO_2R^{33}$, —$CH_2$—$(CH_2)_k$—$NHCOR^{34}$, —$(CH_2)_pCH(OH)$—$CH_2$—$NHCOR^{34}$, —$OCH_2$—($CH_2)_m$—$NHCOR^{34}$, —$OCH_2$—$CH(OH)$—$CH_2$—NH-$COR^{34}$, —$SO_2NHR^{31}$, morpholino, piperidino, oxo-piperidinyl, oxo-pyrrolidinyl, pyridyl, and phenyl wherein the phenyl-ring can again be mono-, di-, tri-, or tetra-substituted wherein the substituents are independently selected from halogen, alkyl, alkoxy, cyano, —$CF_3$, —$OCF_3$, hydroxy, alkoxy-carbonyl, and carboxyl; furanyl that can be mono- or di-substituted, wherein the substituents are independently selected from methyl, hydroxy-methyl, bromine, and phenyl wherein the phenyl-ring can again be mono-, di-, or tri-substituted wherein the substituents are independently selected from halogen, alkyl, alkoxy, cyano, —$CF_3$, —$OCF_3$, hydroxy, alkoxy-carbonyl, alkyl-carbonyl, carboxyl, and methylene-dioxy; thienyl that can be mono-substituted with methyl, chlorine, or phenyl wherein the phenyl-ring can again be mono-, di-, or tri-substituted wherein the substituents are independently selected from halogen, alkyl, alkoxy, cyano, —$CF_3$, —$OCF_3$, hydroxy, alkoxy-carbonyl, alkyl-carbonyl, carboxyl, and methylene-dioxy; pyrimidinyl that can be mono-substituted with alkyl, halogen, cyclopropyl, $CH_3$—S—, methylsulfonyl, or phenyl wherein the phenyl-ring can again be mono-, di-, or tri-substituted wherein the substituents are independently selected from halogen, alkyl, alkoxy, cyano, —$CF_3$, and —$OCF_3$; pyrimidinyl mono- or di-substituted with methoxy; pyridazinyl; benzothienyl; benzofuranyl; quinolinyl; isoquinolinyl; or benzhydryl, wherein both phenyl rings can be mono- or di-substituted, wherein the substituents are independently selected from halogen, alkyl, alkoxy, —$CF_3$, —$OCF_3$, hydroxy, cyano, alkoxy-carbonyl, and alkyl-carbonyl; or $R^3$ represents aryl that can be mono-, di-, tri-, or tetra-substituted, wherein the substituents are independently selected from the group consisting of: hydroxy-$C_{1-5}$-alkyl; 2,3-dihydroxypropyl; di-(hydroxy-$C_{1-5}$-alkyl)-$C_{1-5}$-alkyl; —$CH_2$—$(CH_2)_k$—$NR^{31}R^{32}$; (azetidine-3-carboxylic acid)-1-yl-methyl; (azetidine-3-carboxylic acid $C_{1-5}$-alkylester)-1-yl-methyl; 2-[(azetidine-3-carboxylic acid)-1-yl]-ethyl; 2-[(azetidine-3-carboxylic acid $C_{1-5}$-alkylester)-1-yl]-ethyl; 3-[(azetidine-3-carboxylic acid)-1-yl]-propyl; 3-[(azetidine-3-carboxylic acid $C_{1-5}$-alkylester)-1-yl]-propyl; (pyrrolidine-3-carboxylic acid)-1-yl-methyl; (pyrrolidine-3-carboxylic acid $C_{1-5}$-alkylester)-1-yl-methyl; (pyrrolidine-2-carboxylic acid)-1-yl-methyl; (pyrrolidine-2-carboxylic acid $C_{1-5}$-alkylester)-1-yl-methyl; 2-[(pyrrolidine-3-carboxylic acid)-1-yl]-ethyl; 2-[(pyrrolidine-3-carboxylic acid $C_{1-5}$-alkylester)-1-yl]-ethyl; 2-[(pyrrolidine-2-carboxylic acid)-1-yl]-ethyl; 2-[(pyrrolidine-2-carboxylic acid $C_{1-5}$-alkylester)-1-yl]-ethyl; 3-[(pyrrolidine-3-carboxylic acid)-1-yl]-propyl; 3-[(pyrrolidine-3-carboxylic acid $C_{1-5}$-alkylester)-1-yl]-propyl; 3-[(pyrrolidine-2-carboxylic acid)-1-yl]-propyl; 3-[(pyrrolidine-2-carboxylic acid $C_{1-5}$-alkylester)-1-yl]-propyl; —$CH_2$—$(CH_2)_p$—$CONR^{31}R^{32}$; —CO—$NHR^{31}$; 1-(3-carboxy-azetidinyl)-2-acetyl; 1-(2-carboxy-pyrrolidinyl)-2-acetyl; 1-(3-carboxy-pyrrolidinyl)-2-acetyl; 1-(3-carboxy-azetidinyl)-3-propionyl; 1-(2-carboxy-pyrrolidinyl)-3-propionyl; 1-(3-carboxy-pyrrolidinyl)-3-propionyl; —$(CH_2)_pCH(OH)$—$CH_2$—$NR^{31}R^{32}$; hydroxy-$C_{2-5}$-alkoxy; di-(hydroxy-$C_{1-5}$-alkyl)-$C_{1-5}$-alkoxy; 2,3-dihydroxypropoxy; 2-hydroxy-3-methoxy-propoxy; —$OCH_2$—$(CH_2)_m$—$NR^{31}R^{32}$; 2-pyrrolidin-1-yl-ethoxy; 3-pyrrolidin-1-yl-propoxy; 2-piperazin-1-yl-ethoxy; 2-[4-($C_{1-5}$-alkyl)-piperazin-1-yl]-ethoxy; 2-[4-(2-hydroxy-ethyl)-piperazin-1-yl]-ethoxy; 3-piperazin-1-yl-propoxy; 3-[4-($C_{1-5}$-alkyl)-piperazin-1-yl]-propoxy; 3-[4-(2-hydroxy-ethyl)-piperazin-1-yl]-propoxy; 2-morpholin-4-yl-ethoxy; 3-morpholin-4-yl-propoxy; 2-[(azetidine-3-carboxylic acid)-1-yl]-ethoxy; 2-[(azetidine-3-carboxylic acid $C_{1-5}$-alkylester)-1-yl]-ethoxy; 2-[(pyrrolidine-3-carboxylic acid)-1-yl]-ethoxy; 2-[(pyrrolidine-3-carboxylic acid $C_{1-5}$-alkylester)-1-yl]-ethoxy; 2-[(pyrrolidine-2-carboxylic acid)-1-yl]-ethoxy; 2-[(pyrrolidine-2-carboxylic acid $C_{1-5}$-alkylester)-1-yl]-ethoxy; 2-[(2-hydroxy-pyrrolidine)-1-yl]-ethoxy; 2-[(3-hydroxy-pyrrolidine)-1-yl]-ethoxy; 3-[(azetidine-3-carboxylic acid)-1-yl]-propoxy; 3-[(azetidine-3-carboxylic acid $C_{1-5}$-alkylester)-1-yl]-propoxy; 3-[(pyrrolidine-3-carboxylic acid)-1-yl]-propoxy; 3-[(pyrrolidine-3-carboxylic acid $C_{1-5}$-alkylester)-1-yl]-propoxy; 3-[(pyrrolidine-2-carboxylic acid)-1-yl]-propoxy; 3-[(pyrrolidine-2-carboxylic acid $C_{1-5}$-alkylester)-1-yl]-propoxy; 3-[(2-hydroxy-pyrrolidine)-1-yl]-propoxy; 3-[(3-hydroxy-pyrrolidine)-1-yl]-propoxy; 2-amino-3-hydroxy-2-hydroxymethyl-propoxy; —O—$CH_2$—$CONR^{31}R^{32}$; 1-(3-carboxy-azetidinyl)-1-oxo-2-ethoxy; 1-(pyrrolidine-2-carboxylic acid)-1-yl-1-oxo-2-ethoxy; 1-(pyrrolidine-3-carboxylic acid)-1-yl-1-oxo-2-ethoxy; 3-carbamoyl-propoxy; 3-($C_{1-5}$-alkylcarbamoyl)

propoxy; 3-(2-hydroxyethylcarbamoyl)propoxy; —OCH$_2$—CH(OH)—CH$_2$—NR$^{31}$R$^{32}$; 3-[(azetidine-3-carboxylic acid)-1-yl]-2-hydroxypropoxy; 3-[(azetidine-3-carboxylic acid C$_{1-5}$-alkylester)-1-yl]-2-hydroxypropoxy; 2-hydroxy-3-[(pyrrolidine-3-carboxylic acid)-1-yl]-propoxy; 2-hydroxy-3-[(pyrrolidine-3-carboxylic acid C$_{1-5}$-alkylester)-1-yl]-propoxy; 2-hydroxy-3-[(pyrrolidine-2-carboxylic acid)-1-yl]-propoxy; 2-hydroxy-3-[(pyrrolidine-2-carboxylic acid C$_{1-5}$-alkylester)-1-yl]-propoxy; 2-hydroxy-3-[(2-hydroxy-pyrrolidine)-1-yl]-propoxy; 2-hydroxy-3-[(3-hydroxy-pyrrolidine)-1-yl]-propoxy; 2-hydroxy-3-pyrrolidin-1-yl-propoxy; 2-hydroxy-3-piperazin-1-yl-propoxy; 2-hydroxy-3-[4-(C$_{1-5}$-alkyl)-piperazin-1-yl]-propoxy; 2-hydroxy-3-[4-(2-hydroxy-ethyl)-piperazin-1-yl]-propoxy; 2-hydroxy-3-morpholin-4-yl-propoxy; —NR$^{31}$R$^{32}$; —NHCO—R$^{31}$; —CH$_2$—(CH$_2$)$_k$—NHSO$_2$R$^{33}$; —(CH$_2$)$_p$CH(OH)—CH$_2$—NHSO$_2$R$^{33}$; —OCH$_2$—(CH$_2$)$_m$—NHSO$_2$R$^{33}$; —OCH$_2$—CH(OH)—CH$_2$—NHSO$_2$R$^{33}$; —CH$_2$—(CH$_2$)$_k$—NHCOR$^{34}$; —(CH$_2$)$_p$CH(OH)—CH$_2$—NHCOR$^{34}$; —OCH$_2$—(CH$_2$)$_m$—NHCOR$^{34}$; —OCH$_2$—CH(OH)—CH$_2$—NHCOR$^{34}$; —SO$_2$NHR$^{31}$; phenyl, wherein said phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; pyridyl, wherein said pyridyl ring can further be mono- or di-substituted, wherein the substituents are independently selected from alkyl, alkoxy, halogen, hydroxy, and —CF$_3$; furanyl, wherein said furanyl ring can further be mono- or di-substituted, wherein the substituents are independently selected from alkyl, alkoxy, and halogen; thienyl, wherein said thienyl ring can further be mono- or di-substituted, wherein the substituents are independently selected from alkyl, alkoxy, and halogen; oxadiazolyl, wherein said oxadiazolyl ring can further be mono-substituted with alkyl, pyridyl or phenyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; isoxazolyl, wherein said isoxazolyl ring can further be mono- or di-substituted, wherein the substituents are independently selected from alkyl, phenyl and pyridyl; halogen; alkyl; alkoxy; —CF$_3$; —OCF$_3$; hydroxy; cyano; alkoxy-carbonyl; alkyl-carbonyl; carboxyl; monoalkyl-amino; dialkyl-amino; pyrrolidino; morpholino; thiomorpholino; piperidino; N-benzyl-N-alkyl-amino; N-pyridyl-N-methyl-amino; (dialkyl-amino)-alkoxy; phenyl-alkoxy, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; phenyl-amino-carbonyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; phenyl-alkyl-amino-carbonyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; alkyl-amino-carbonyl; dialkyl-amino-carbonyl; pyridyl-amino-carbonyl; phenyl-carbonyl-amino, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; phenyl-alkyl-carbonyl-amino, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; alkyl-carbonyl-amino; pyridyl-carbonyl-amino; and tetrahydro-isoquinolinyl;

or R$^3$ represents the following group:

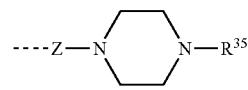

wherein Z represents phenyl or pyridyl;
R$^{31}$ represents hydrogen, methyl, ethyl, 1-propyl, 2-propyl, 2-hydroxyethyl, 2-hydroxy-1-hydroxymethyl-ethyl, 2,3-dihydroxypropyl, 2-C$_{1-5}$-alkoxyethyl, 3-hydroxypropyl, 3-C$_{1-5}$-alkoxypropyl, 2-aminoethyl, 2-(C$_{1-5}$-alkylamino)ethyl, 2-(di-(C$_{1-5}$-alkyl)amino)ethyl, carboxymethyl, 1-(C$_{1-5}$-alkylcarboxy)methyl, 2-carboxyethyl, 2-(C$_{1-5}$-alkylcarboxy)ethyl, phenyl, pyridyl, phenyl-alkyl, hydroxyalkyl-carbonyl, alkyl-carbonyl, cycloalkyl-carbonyl, or phenyl-carbonyl;
R$^{32}$ represents hydrogen, methyl, or ethyl;
R$^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;
R$^{34}$ represents hydroxymethyl, hydroxyethyl, aminomethyl, methylaminomethyl, dimethylaminomethyl, aminoethyl, 2-methylamino-ethyl, or 2-dimethylamino-ethyl;
k represents the integer 1, 2, or 3;
m represents the integer 1 or 2;
p represents 0, 1, or 2;
R$^{35}$ represents alkyl; alkyl-carbonyl; alkoxy-carbonyl; cycloalkyl-carbonyl; aryl, wherein the aryl-ring can be mono-, di-, tri-, or tetra-substituted wherein the substituents are independently selected from halogen, alkyl, alkoxy, —CF$_3$, —OCF$_3$, hydroxy, alkoxy-carbonyl, and carboxyl; aryl-carbonyl, wherein the aryl-ring can be mono-, di-, tri-, or tetra-substituted wherein the substituents are independently selected from halogen, alkyl, alkoxy, —CF$_3$, —OCF$_3$, hydroxy, alkoxy-carbonyl, and carboxyl; aryl-alkyl, wherein the aryl-ring can be mono-, di-, tri-, or tetra-substituted wherein the substituents are independently selected from halogen, alkyl, alkoxy, —CF$_3$, —OCF$_3$, hydroxy, alkoxy-carbonyl, and carboxyl; pyridyl, wherein the pyridyl-ring can be mono-, di-, or tri-substituted wherein the substituents are independently selected from halogen, alkyl, alkoxy, —CF$_3$, —OCF$_3$, hydroxy, alkoxy-carbonyl, and carboxyl; pyridyl-alkyl, wherein the pyridyl-ring can be mono-, di-, or tri-substituted wherein the substituents are independently selected from halogen, alkyl, alkoxy, —CF$_3$, —OCF$_3$, hydroxy, alkoxy-carbonyl, and carboxyl; pyrimidinyl, wherein the pyrimidinyl-ring can be mono-, or di-substituted wherein the substituents are independently selected from halogen, alkyl, alkoxy, and —CF$_3$; furanyl-carbonyl; furanyl-alkyl, wherein the furanyl-ring can be mono-, or di-substituted wherein the substituents are independently selected from methyl, hydroxy-methyl, and bromine; thienyl-alkyl that can be mono-substituted with methyl or chlorine; benzothienyl-alkyl; benzofuranyl-alkyl; imidazolyl-alkyl; or thiazolyl-alkyl; and
R$^4$ represents alkyl; cycloalkyl; benzo[1,3]dioxolyl; benzo[1,3]dioxolyl —CH$_2$—; benzothienyl; benzofuranyl; indazolyl; indolyl that can be mono- or di-substituted, wherein the substituents are independently selected from halogen, alkyl, alkoxy, —CF$_3$, —OCF$_3$, and hydroxy; quinolinyl; isoquinolinyl; benzhydryl, wherein both phenyl-rings can be mono- or di-substituted, wherein the substituents are independently selected from halogen, alkyl, alkoxy, —$CF_3$, —$OCF_3$, hydroxy, cyano, alkoxy-carbonyl, and alkyl-carbonyl; aryl that can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —$CF_3$, —$OCF_3$, hydroxy, alkoxy-carbonyl, and carboxyl; aryl —CH=CH—, wherein aryl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; aryl —$CH_2$—$CH_2$—, wherein aryl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl —CH=CH—, wherein pyridyl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl —$CH_2$—$CH_2$—, wherein pyridyl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; aryl —$CH_2$—, wherein aryl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl —$CH_2$—, wherein pyridyl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; thienyl —$CH_2$—; pyrimidinyl —CH=CH—; furanyl —CH=CH—; or thienyl —CH=CH—;

and optically pure enantiomers, mixtures of enantiomers such as for example racemates, optically pure diastereomers, mixtures of diastereomers, diastereomeric racemates, mixtures of diastereomeric racemates, and meso-forms, as well as salts and solvates of such compounds, and morphological forms.

The present invention also relates to compounds of the formula I':

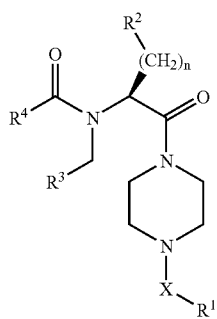

formula I' wherein n, X, $R^1$, $R^2$, $R^3$ and $R^4$ are as defined for formula I above.

The present invention further also relates to compounds of the formula I, wherein X represents —$(CH_2)_{0-2}$— or —C(=O)—;

n represents the integer 0, 1 or 2;

$R^1$ represents hydrogen; alkyl; cycloalkyl; ethoxy-carbonyl; hydroxy-ethyl; benzo[1,3]dioxolyl; aryl that can be mono-, di-, tri-, or tetra-substituted, wherein the substituents are independently selected from halogen, alkyl, alkoxy, —$CF_3$, —$OCF_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —$CF_3$, —$OCF_3$, hydroxy, alkoxy-carbonyl, and carboxyl; furanyl that can be mono-, or di-substituted, wherein the substituents are independently selected from methyl, hydroxy-methyl, and bromine; thienyl that can be mono-substituted with methyl or chlorine; pyrimidinyl that can be mono-substituted with alkyl, halogen, cyclopropyl, $CH_3$—S—, or methylsulfonyl or that can be mono- or di-substituted with methoxy; pyridazinyl; benzothienyl; benzofuranyl; quinolinyl; isoquinolinyl; or benzhydryl, wherein both phenyl rings can be mono- or di-substituted, wherein the substituents are independently selected from halogen, alkyl, alkoxy, —$CF_3$, —$OCF_3$, hydroxy, cyano, alkoxy-carbonyl, and alkyl-carbonyl;

$R^2$ represents hydrogen; alkyl; indolyl; carboxyl; alkoxy-carbonyl; amino-carbonyl; imidazolyl; cycloalkyl; aryl that can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —$CF_3$, —$OCF_3$, hydroxy, alkoxy-carbonyl, and carboxyl; benzothienyl; thiazolyl; or thienyl;

$R^3$ represents hydrogen; alkyl; cycloalkyl; formyl; acetyl; ethoxy-carbonyl; hydroxy-ethyl; benzo[1,3]dioxolyl; pyridyl that can be mono-, di-, or tri-substituted, wherein the substituents are independently selected from phenyl, halogen, alkyl, alkoxy, —$CF_3$, —$OCF_3$, hydroxy, alkoxy-carbonyl, and carboxyl; furanyl that can be mono- or di-substituted, wherein the substituents are independently selected from phenyl, methyl, hydroxy-methyl, and bromine; thienyl that can be mono-substituted with phenyl, methyl, or chlorine; pyrimidinyl that can be mono-substituted with phenyl, alkyl, halogen, cyclopropyl, $CH_3$—S—, or methylsulfonyl or that can be mono- or di-substituted with methoxy; pyridazinyl; benzothienyl; benzofuranyl; quinolinyl; isoquinolinyl; or benzhydryl, wherein both phenyl rings can be mono- or di-substituted, wherein the substituents are independently selected from halogen, alkyl, alkoxy, —$CF_3$, —$OCF_3$, hydroxy, cyano, alkoxy-carbonyl, and alkyl-carbonyl; or $R^3$ represents aryl that can be mono-, di-, tri-, or tetra-substituted, wherein the substituents are independently selected from the group consisting of:

phenyl, wherein said phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; pyridyl, wherein said pyridyl ring can further be mono- or di-substituted, wherein the substituents are independently selected from alkyl, alkoxy, halogen, hydroxy, and —$CF_3$; furanyl, wherein said furanyl ring can further be mono- or di-substituted, wherein the substituents are independently selected from alkyl, alkoxy, and halogen; thienyl, wherein said thienyl ring can further be mono- or di-substituted, wherein the substituents are independently selected from alkyl, alkoxy, and halogen; oxadiazolyl, wherein said oxadiazolyl ring can further be mono-substituted with alkyl or phenyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; pyridyl; isoxazolyl, wherein said isoxazolyl ring can further be mono- or di-substituted, wherein the substituents are independently selected from alkyl, phenyl and pyridyl; halogen; alkyl; alkoxy; —CF$_3$; —OCF$_3$; hydroxy; cyano; alkoxy-carbonyl; alkyl-carbonyl; carboxyl; monoalkyl-amino; dialkyl-amino; pyrrolidino; morpholino; thiomorpholino; piperidino; N-benzyl-N-alkyl-amino; N-pyridyl-N-methyl-amino; (dialkyl-amino)-alkoxy; phenyl-alkoxy, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; phenyl-amino-carbonyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; phenyl-alkyl-amino-carbonyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; alkyl-amino-carbonyl; dialkyl-amino-carbonyl; pyridyl-amino-carbonyl; phenyl-carbonyl-amino, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; phenyl-alkyl-carbonyl-amino, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; alkyl-carbonyl-amino; and pyridyl-carbonyl-amino; and R$^4$ represents alkyl; cycloalkyl; benzo[1,3]dioxolyl; benzo[1,3]dioxolyl —CH$_2$—; benzothienyl; benzofuranyl; indazolyl; indolyl that can be mono- or di-substituted, wherein the substituents are independently selected from halogen, alkyl, alkoxy, —CF$_3$, —OCF$_3$, and hydroxy; quinolinyl; isoquinolinyl; benzhydryl, wherein both phenyl-rings can be mono- or di-substituted, wherein the substituents are independently selected from halogen, alkyl, alkoxy, —CF$_3$, —OCF$_3$, hydroxy, cyano, alkoxy-carbonyl, and alkyl-carbonyl; aryl that can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —CF$_3$, —OCF$_3$, hydroxy, alkoxy-carbonyl, and carboxyl; aryl —CH═CH—, wherein aryl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; aryl —CH$_2$—CH$_2$—, wherein aryl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl —CH═CH—, wherein pyridyl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl —CH$_2$—CH$_2$—, wherein pyridyl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; aryl —CH$_2$—, wherein aryl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl —CH$_2$—, wherein pyridyl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; or thienyl —CH$_2$—;

and optically pure enantiomers, mixtures of enantiomers such as for example racemates, optically pure diastereomers, mixtures of diastereomers, diastereomeric racemates, mixtures of diastereomeric racemates, and meso-forms, as well as salts and solvates of such compounds, and morphological forms.

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference to a compound of formula I is to be understood as referring also to optically pure enantiomers, mixtures of enantiomers such as racemates, diastereomers, mixtures of diastereomers, diastereomeric racemates, mixtures of diastereomeric racemates, and meso-forms, as well as salts (especially pharmaceutically acceptable salts) and solvates (including hydrates) of such compounds, and morphological forms, as appropriate and expedient.

In the definitions of formula I—if not otherwise stated—the term alkyl, alone or in combination with other groups, means saturated, straight or branched chain groups with one to seven carbon atoms, preferably one to four carbon atoms. Examples of alkyl groups are methyl, ethyl, n-propyl, iso-propyl, n-butyl, iso-butyl, sec-butyl, tert-butyl, 2,2-dimethyl-propyl, pentyl, hexyl and heptyl. The methyl, ethyl and iso-propyl groups are preferred, unless indicated otherwise.

The term alkoxy, alone or in combination with other groups, refers to an R—O— group, wherein R is an alkyl. Examples of alkoxy groups are methoxy, ethoxy, propoxy, iso-propoxy, n-butoxy, iso-butoxy, sec-butoxy and tert-butoxy.

The term halogen means fluorine, chlorine, bromine or iodine, preferably fluorine and chlorine.

The term cycloalkyl, alone or in combination with other groups, means a saturated cyclic hydrocarbon ring system with 3 to 7 carbon atoms, e.g. cyclopropyl, cyclobutyl, cyclopentyl, cyclohexyl and cycloheptyl. The cyclopropyl group is a preferred group.

The term aryl, alone or in combination with other groups, relates to a phenyl or naphthyl group, preferably a phenyl group.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methane-sulfonic acid, ethanesulfonic acid, ethanedisulfonic acid, p-toluenesulfonic acid, salicylic acid, succinic acid, trifluoroacetic acid, and the like that are non toxic to living organisms or in case the compound of formula I is acidic in nature with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", *Int. J. Pharm.* (1986), 33, 201-217.

The compounds of the formula I contain one or more asymmetric carbon atoms and may be prepared in form of optically pure enantiomers, mixtures of enantiomers such as racemates, diastereomers, mixtures of diastereomers, diastereomeric racemates, mixtures of diastereomeric racemates, or meso-forms.

The present invention encompasses all these forms. Mixtures can be separated in a manner known per se, e.g. by column chromatography, thin layer chromatography (TLC), high performance liquid chromatography (HPLC), or crystallization.

Preferred compounds are compounds of the formula I, wherein
X represents —$CH_2$—;
n represents the integer 1;
$R^1$ represents aryl that can be mono-, di-, tri-, or tetra-substituted, wherein the substituents are independently selected from halogen, alkyl, alkoxy, —$CF_3$, —$OCF_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —$CF_3$, —$OCF_3$, hydroxy, alkoxy-carbonyl, and carboxyl; furanyl that can be mono- or di-substituted, wherein the substituents are independently selected from methyl, hydroxy-methyl, and bromine; thienyl that can be mono-substituted with methyl or chlorine; benzothienyl; benzofuranyl; quinolinyl; or isoquinolinyl;
$R^2$ represents aryl that can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —$CF_3$, —$OCF_3$, hydroxy, alkoxy-carbonyl, and carboxyl; benzothienyl; thiazolyl; or thienyl; and
$R^3$ and $R^4$ are as defined for formula I above.

Also preferred compounds are compounds of the formula I, wherein
X represents —$CH_2$—;
n represents the integer 1;
$R^1$ and $R^2$ both represent phenyl; and
$R^3$ and $R^4$ are as defined for formula I above.

Also preferred compounds are compounds of the formula I, wherein
X represents —$CH_2$—;
n represents the integer 1;
$R^1$ and $R^2$ both represent phenyl;
$R^3$ is as defined for formula I above; and
$R^4$ represents a radical of the formula

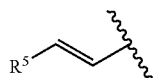

wherein $R^5$ represents phenyl that can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl.

The present invention also relates to compounds of formula I wherein the meanings of one or more of the substituents and symbols as defined for formula I, or a preferred embodiment of formula I, are replaced by their preferred meanings as defined herein, such as those defined for the above-given preferred compounds.

In an especially preferred embodiment, the present invention relates to a compound of formula I, wherein
X represents —$(CH_2)_{0-1}$— or —C(=O)—;
n represents the integer 1;
$R^1$ represents hydrogen; alkyl; ethoxy-carbonyl; hydroxy-ethyl; benzo[1,3]dioxolyl; aryl that can be mono-substituted with halogen, alkyl, alkoxy, —$CF_3$, or alkyl-carbonyl; pyridyl that can be mono-substituted with halogen, alkyl, alkoxy, or —$CF_3$; furanyl that can be mono- or di-substituted, wherein the substituents are independently selected from methyl, hydroxy-methyl, and bromine; thienyl that can be mono-substituted with methyl or chlorine; pyrimidinyl; isoquinolinyl; or benzhydryl;
$R^2$ represents indolyl; imidazolyl; aryl that can be mono- or di-substituted, wherein the substituents are independently selected from halogen, alkyl, hydroxy, and cyano; pyridyl; benzothienyl; thiazolyl; or thienyl;
$R^3$ represents aryl that is mono-substituted with phenyl, pyridyl, alkyl, alkoxy, pyrrolidino, (dialkyl-amino)-alkoxy or phenyl-alkoxy; and
$R^4$ represents aryl —CH=CH—, wherein aryl is mono-substituted with alkoxy or —$CF_3$, especially methoxy or —$CF_3$; or aryl —$CH_2$—$CH_2$—, wherein aryl is di-substituted with —$CF_3$.

In a further especially preferred embodiment, the present invention relates to a compound of formula I, wherein
X represents —($CH_2$)—;
n represents the integer 1;
$R^1$ represents hydrogen; methyl; cycloalkyl; benzo[1,3]dioxolyl; aryl that can be mono-, di-, tri-, or tetra-substituted, wherein the substituents are independently selected from halogen, alkyl, alkoxy, —$CF_3$, —$OCF_3$, hydroxy, cyano, alkoxy-carbonyl, alkyl-carbonyl, and carboxyl; pyridyl that can be mono-, or di-substituted, wherein the substituents are independently selected from halogen, alkyl, alkoxy, —$CF_3$, —$OCF_3$, hydroxy, alkoxy-carbonyl, and carboxyl; furanyl that can be mono-, or di-substituted, wherein the substituents are independently selected from methyl, hydroxy-methyl, and bromine; thienyl that can be mono-substituted with methyl or chlorine; pyrimidinyl that can be mono-substituted with alkyl, halogen, or cyclopropyl or that can be mono- or di-substituted with methoxy; pyridazinyl; benzothienyl; benzofuranyl; quinolinyl; isoquinolinyl; imidazolyl; thiazolyl; or oxazolyl;
$R^2$ represents cycloalkyl; aryl that can be mono-, di-, or tri-substituted, wherein the substituents are independently selected from halogen, alkyl, alkoxy, —$CF_3$, and cyano; pyridyl that can be mono-, or di-substituted, wherein the substituents are independently selected from halogen, alkyl, alkoxy, —$CF_3$, and —$OCF_3$; thiazolyl; or thienyl;
$R^3$ represents alkyl; cycloalkyl; pyridyl that can be mono-, di-, or tri-substituted, wherein the substituents are independently selected from: halogen, alkyl, alkoxy, —$CF_3$, —$OCF_3$, alkoxy-carbonyl, carboxyl, hydroxy-$C_{1-5}$-alkyl, 2,3-dihydroxypropyl, di-(hydroxy-$C_{1-5}$-alkyl)-$C_{1-5}$-alkyl, —$CH_2$—($CH_2$)$_k$—$NR^{31}R^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —$CH_2$—$(CH_2)_p$—$CONR^{31}R^{32}$, —CO—$NHR^{31}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —$(CH_2)_p$CH(OH)—$CH_2$—$NR^{31}R^{32}$, hydroxy-$C_{2-5}$-alkoxy, di-(hydroxy-$C_{1-5}$-alkyl)-$C_{1-5}$-alkoxy, 2,3-dihydroxypropoxy, 2-hydroxy-3-methoxy-propoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, 1-(3-carboxy-azetidinyl)-1-oxo-2-ethoxy, 1-(pyrrolidine-2-carboxylic acid)-1-yl-1-oxo-2-ethoxy, 1-(pyrrolidine-3-carboxylic acid)-1-yl-1-oxo-2-ethoxy, 3-carbamoyl-propoxy, 3-($C_{1-5}$-alkylcarbamoyl) propoxy, 3-(2-hydroxyethylcarbamoyl)propoxy, —$OCH_2$—CH(OH)—$CH_2$—$NR^{31}R^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —$NR^{31}R^{32}$, —NHCO—$R^{31}$, —$CH_2$—$(CH_2)_k$—$NHSO_2R^{33}$, —$(CH_2)_p$CH(OH)—$CH_2$—$NHSO_2R^{33}$, —$OCH_2$—$(CH_2)_m$—$NHSO_2R^{33}$, —$OCH_2$—CH(OH)—$CH_2$—$NHSO_2R^{33}$, —$CH_2$—$(CH_2)_k$—$NHCOR^{34}$, —$(CH_2)_p$CH(OH)—$CH_2$—$NHCOR^{34}$, —$OCH_2$—$(CH_2)_m$—$NHCOR^{34}$, —$OCH_2$—CH(OH)—$CH_2$—$NHCOR^{34}$, —$SO_2NHR^{31}$, and phenyl wherein the phenyl-ring can again be mono-, di-, tri-, or tetra-substituted wherein the substituents are independently selected from halogen, alkyl, alkoxy, —$CF_3$, —$OCF_3$, hydroxy, alkoxy-carbonyl, and carboxyl; furanyl that can be mono- or di-substituted, wherein the substituents are independently selected from methyl, hydroxy-methyl, bromine, and phenyl, wherein said phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; thienyl that can be mono-substituted with methyl, chlorine, or phenyl wherein said phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; benzothienyl; benzofuranyl; quinolinyl; or isoquinolinyl; or $R^3$ represents aryl that can be mono-, di-, tri-, or tetra-substituted, wherein the substituents are independently selected from the group consisting of:

hydroxy-$C_{1-5}$-alkyl; 2,3-dihydroxypropyl; di-(hydroxy-$C_{1-5}$-alkyl)-$C_{1-5}$-alkyl; —$CH_2$—$(CH_2)_k$—$NR^{31}R^{32}$; (azetidine-3-carboxylic acid)-1-yl-methyl; (azetidine-3-carboxylic acid $C_{1-5}$-alkylester)-1-yl-methyl; 2-[(azetidine-3-carboxylic acid)-1-yl]-ethyl; 2-[(azetidine-3-carboxylic acid $C_{1-5}$-alkylester)-1-yl]-ethyl; 3-[(azetidine-3-carboxylic acid)-1-yl]-propyl; 3-[(azetidine-3-carboxylic acid $C_{1-5}$-alkylester)-1-yl]-propyl; (pyrrolidine-3-carboxylic acid)-1-yl-methyl; (pyrrolidine-3-carboxylic acid $C_{1-5}$-alkylester)-1-yl-methyl; (pyrrolidine-2-carboxylic acid)-1-yl-methyl; (pyrrolidine-2-carboxylic acid $C_{1-5}$-alkylester)-1-yl-methyl; 2-[(pyrrolidine-3-carboxylic acid)-1-yl]-ethyl; 2-[(pyrrolidine-3-carboxylic acid $C_{1-5}$-alkylester)-1-yl]-ethyl; 2-[(pyrrolidine-2-carboxylic acid)-1-yl]-ethyl; 2-[(pyrrolidine-2-carboxylic acid $C_{1-5}$-alkylester)-1-yl]-ethyl; 3-[(pyrrolidine-3-carboxylic acid)-1-yl]-propyl; 3-[(pyrrolidine-3-carboxylic acid $C_{1-5}$-alkylester)-1-yl]-propyl; 3-[(pyrrolidine-2-carboxylic acid)-1-yl]-propyl; 3-[(pyrrolidine-2-carboxylic acid $C_{1-5}$-alkylester)-1-yl]-propyl; —$CH_2$—$(CH_2)_p$—$CONR^{31}R^{32}$—CO—$NHR^{31}$; 1-(3-carboxy-azetidinyl)-2-acetyl; 1-(2-carboxy-pyrrolidinyl)-2-acetyl; 1-(3-carboxy-pyrrolidinyl)-2-acetyl; 1-(3-carboxy-azetidinyl)-3-propionyl; 1-(2-carboxy-pyrrolidinyl)-3-propionyl; 1-(3-carboxy-pyrrolidinyl)-3-propionyl; —$(CH_2)_p$CH(OH)—$CH_2$—$NR^{31}R^{32}$; hydroxy-$C_{2-5}$-alkoxy; di-(hydroxy-$C_{1-5}$-alkyl)-$C_{1-5}$-alkoxy; 2,3-dihydroxypropoxy; 2-hydroxy-3-methoxy-propoxy; —$OCH_2$—$(CH_2)_m$—$NR^{31}R^{32}$; 2-pyrrolidin-1-yl-ethoxy; 3-pyrrolidin-1-yl-propoxy; 2-piperazin-1-yl-ethoxy; 2-[4-($C_{1-5}$-alkyl)-piperazin-1-yl]-ethoxy; 2-[4-(2-hydroxy-ethyl)-piperazin-1-yl]-ethoxy; 3-piperazin-1-yl-propoxy; 3-[4-($C_{1-5}$-alkyl)-piperazin-1-yl]-propoxy; 3-[4-(2-hydroxy-ethyl)-piperazin-1-yl]-propoxy; 2-morpholin-4-yl-ethoxy; 3-morpholin-4-yl-propoxy; 2-[(azetidine-3-carboxylic acid)-1-yl]-ethoxy; 2-[(azetidine-3-carboxylic acid $C_{1-5}$-alkylester)-1-yl]-ethoxy; 2-[(pyrrolidine-3-carboxylic acid)-1-yl]-ethoxy; 2-[(pyrrolidine-3-carboxylic acid $C_{1-5}$-alkylester)-1-yl]-ethoxy; 2-[(pyrrolidine-2-carboxylic acid)-1-yl]-ethoxy; 2-[(pyrrolidine-2-carboxylic acid $C_{1-5}$-alkylester)-1-yl]-ethoxy; 2-[(2-hydroxy-pyrrolidine)-1-yl]-ethoxy; 2-[(3-hydroxy-pyrrolidine)-1-yl]-ethoxy; 3-[(azetidine-3-carboxylic acid)-1-yl]-propoxy; 3-[(azetidine-3-carboxylic acid $C_{1-5}$-alkylester)-1-yl]-propoxy; 3-[(pyrrolidine-3-carboxylic acid)-1-yl]-propoxy; 3-[(pyrrolidine-3-carboxylic acid $C_{1-5}$-alkylester)-1-yl]-propoxy; 3-[(pyrrolidine-2-carboxylic acid)-1-yl]-propoxy; 3-[(pyrrolidine-2-carboxylic acid $C_{1-5}$-alkylester)-1-yl]-propoxy; 3-[(2-hydroxy-pyrrolidine)-1-yl]-propoxy; 3-[(3-hydroxy-pyrrolidine)-1-yl]-propoxy; 2-amino-3-hydroxy-2-hydroxymethyl-propoxy; $-O-CH_2-CONR^{31}R^{32}$; 1-(3-carboxy-azetidinyl)-1-oxo-2-ethoxy; 1-(pyrrolidine-2-carboxylic acid)-1-yl-1-oxo-2-ethoxy; 1-(pyrrolidine-3-carboxylic acid)-1-yl-1-oxo-2-ethoxy; 3-carbamoyl-propoxy; 3-($C_{1-5}$-alkylcarbamoyl)propoxy; 3-(2-hydroxyethylcarbamoyl)propoxy; $-OCH_2-CH(OH)-CH_2-NR^{31}R^{32}$; 3-[(azetidine-3-carboxylic acid)-1-yl]-2-hydroxypropoxy; 3-[(azetidine-3-carboxylic acid $C_{1-5}$-alkylester)-1-yl]-2-hydroxypropoxy; 2-hydroxy-3-[(pyrrolidine-3-carboxylic acid)-1-yl]-propoxy; 2-hydroxy-3-[(pyrrolidine-3-carboxylic acid $C_{1-5}$-alkylester)-1-yl]-propoxy; 2-hydroxy-3-[(pyrrolidine-2-carboxylic acid)-1-yl]-propoxy; 2-hydroxy-3-[(pyrrolidine-2-carboxylic acid $C_{1-5}$-alkylester)-1-yl]-propoxy; 2-hydroxy-3-[(2-hydroxy-pyrrolidine)-1-yl]-propoxy; 2-hydroxy-3-[(3-hydroxy-pyrrolidine)-1-yl]-propoxy; 2-hydroxy-3-pyrrolidin-1-yl-propoxy; 2-hydroxy-3-piperazin-1-yl-propoxy; 2-hydroxy-3-[4-($C_{1-5}$-alkyl)-piperazin-1-yl]-propoxy; 2-hydroxy-3-[4-(2-hydroxy-ethyl)-piperazin-1-yl]-propoxy; 2-hydroxy-3-morpholin-4-yl-propoxy; $-NR^{31}R^{32}$; $-NHCO-R^{31}$; $-CH_2-(CH_2)_k-NHSO_2R^{33}$; $-(CH_2)_pCH(OH)-CH_2-NHSO_2R^{33}$; $-OCH_2-(CH_2)_m-NHSO_2R^{33}$; $-OCH_2-CH(OH)-CH_2-NHSO_2R^{33}$; $-CH_2-(CH_2)_k-NHCOR^{34}$; $-(CH_2)_pCH(OH)-CH_2-NHCOR^{34}$; $-OCH_2-(CH_2)_m-NHCOR^{34}$; $-OCH_2-CH(OH)-CH_2-NHCOR^{34}$; $-SO_2NHR^{31}$; phenyl, wherein said phenyl ring can further be mono-, di-, or tri-substituted, wherein the substituents are independently selected from halogen, alkyl, alkoxy, $-CF_3$, $-OCF_3$, hydroxy, cyano, alkoxy-carbonyl, alkyl-carbonyl, carboxyl, and methylene-dioxy; pyridyl, wherein said pyridyl ring can further be mono- or di-substituted, wherein the substituents are independently selected from alkyl, alkoxy, halogen, hydroxy, and $-CF_3$; furanyl, wherein said furanyl ring can further be mono- or di-substituted, wherein the substituents are independently selected from alkyl, alkoxy, and halogen; thienyl, wherein said thienyl ring can further be mono- or di-substituted, wherein the substituents are independently selected from alkyl, alkoxy, and halogen; oxadiazolyl, wherein said oxadiazolyl ring can further be mono-substituted with alkyl or phenyl, wherein the phenyl ring can further be mono-, di-, or tri-substituted, wherein the substituents are independently selected from halogen, alkyl, alkoxy, $-CF_3$, $-OCF_3$, hydroxy, cyano, alkoxy-carbonyl, alkyl-carbonyl, carboxyl, and methylene-dioxy; isoxazolyl, wherein said isoxazolyl ring can further be mono- or di-substituted, wherein the substituents are independently selected from alkyl, phenyl and pyridyl; halogen; alkyl; alkoxy; $-CF_3$; $-OCF_3$; hydroxy; cyano; alkoxy-carbonyl; alkyl-carbonyl; carboxyl; monoalkyl-amino; dialkyl-amino; pyrrolidino; morpholino; thiomorpholino; piperidino; N-benzyl-N-alkyl-amino; N-pyridyl-N-methyl-amino; (dialkyl-amino)-alkoxy; phenyl-alkoxy, wherein the phenyl ring can further be mono-, di-, or tri-substituted, wherein the substituents are independently selected from halogen, alkyl, alkoxy, $-CF_3$, $-OCF_3$, hydroxy, cyano, alkoxy-carbonyl, alkyl-carbonyl, carboxyl, and methylene-dioxy; phenyl-amino-carbonyl, wherein the phenyl ring can further be mono-, di-, or tri-substituted, wherein the substituents are independently selected from halogen, alkyl, alkoxy, $-CF_3$, $-OCF_3$, hydroxy, cyano, alkoxy-carbonyl, alkyl-carbonyl, carboxyl, and methylene-dioxy; phenyl-alkyl-amino-carbonyl, wherein the phenyl ring can further be mono-, di-, or tri-substituted, wherein the substituents are independently selected from halogen, alkyl, alkoxy, $-CF_3$, $-OCF_3$, hydroxy, cyano, alkoxy-carbonyl, alkyl-carbonyl, carboxyl, and methylene-dioxy; alkyl-amino-carbonyl; dialkyl-amino-carbonyl; pyridyl-amino-carbonyl; phenyl-carbonyl-amino, wherein the phenyl ring can further be mono-, di-, or tri-substituted, wherein the substituents are independently selected from halogen, alkyl, alkoxy, $-CF_3$, $-OCF_3$, hydroxy, cyano, alkoxy-carbonyl, alkyl-carbonyl, carboxyl, and methylene-dioxy; phenyl-alkyl-carbonyl-amino, wherein the phenyl ring can further be mono-, di-, or tri-substituted, wherein the substituents are independently selected from halogen, alkyl, alkoxy, $-CF_3$, $-OCF_3$, hydroxy, cyano, alkoxy-carbonyl, alkyl-carbonyl, carboxyl, and methylene-dioxy; alkyl-carbonyl-amino; and pyridyl-carbonyl-amino;

or $R^3$ represents the following group:

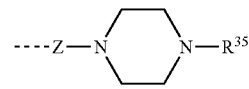

wherein Z represents phenyl or pyridyl;
$R^{31}$ represents hydrogen, methyl, ethyl, 1-propyl, 2-propyl, 2-hydroxyethyl, 2-hydroxy-1-hydroxymethyl-ethyl, 2,3-dihydroxypropyl, 2-$C_{1-5}$-alkoxyethyl, 3-hydroxypropyl, 3-$C_{1-5}$-alkoxypropyl, 2-aminoethyl, 2-($C_{1-5}$-alkylamino)ethyl, 2-(di-($C_{1-5}$-alkyl)amino)ethyl, carboxymethyl, 1-($C_{1-5}$-alkylcarboxy)methyl, 2-carboxyethyl, or 2-($C_{1-5}$-alkylcarboxy)ethyl;
$R^{32}$ represents hydrogen, methyl, or ethyl;
$R^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;
$R^{34}$ represents hydroxymethyl, hydroxyethyl, aminomethyl, methylaminomethyl, dimethylaminomethyl, aminoethyl, 2-methylamino-ethyl, or 2-dimethylamino-ethyl;
k represents the integer 1, 2, or 3;
m represents the integer 1 or 2;
p represents 0, 1, or 2;
$R^{35}$ represents alkyl; alkyl-carbonyl; alkoxy-carbonyl; cycloalkyl-carbonyl; aryl, wherein the aryl-ring can be mono-, di-, tri-, or tetra-substituted wherein the substituents are independently selected from halogen, alkyl, alkoxy, $-CF_3$, $-OCF_3$, hydroxy, alkoxy-carbonyl, and carboxyl; aryl-carbonyl, wherein the aryl-ring can be mono-, di-, tri-, or tetra-substituted wherein the substituents are independently selected from halogen, alkyl, alkoxy, $-CF_3$, $-OCF_3$, hydroxy, alkoxy-carbonyl, and carboxyl; aryl-alkyl, wherein the aryl-ring can be mono-, di-, tri-, or tetra-substituted wherein the substituents are independently selected from halogen, alkyl, alkoxy, $-CF_3$, $-OCF_3$, hydroxy, alkoxy-carbonyl, and carboxyl; pyridyl, wherein the pyridyl-ring can be mono-, di-, or tri-substituted wherein the substituents are independently selected from halogen, alkyl, alkoxy, $-CF_3$, $-OCF_3$, hydroxy, alkoxy-carbonyl, and carboxyl; pyridyl-alkyl, wherein the pyridyl-ring can be mono-, di-, or tri-substituted wherein the substituents are independently selected from halogen, alkyl, alkoxy, $-CF_3$, $-OCF_3$, hydroxy, alkoxy-carbonyl, and carboxyl; pyrimidinyl, wherein the pyrimidinyl-ring can be mono-, or di-substituted wherein the substituents are independently selected from halogen, alkyl, alkoxy, and $-CF_3$; furanyl-carbonyl; furanyl-alkyl, wherein the furanyl-ring can be mono-, or di-substituted wherein the substituents are independently selected from methyl, hydroxy-methyl, and bromine; thienyl-alkyl that can be mono-substituted with methyl or chlorine; benzothienyl-alkyl; benzofuranyl-alkyl; imidazolyl-alkyl; or thiazolyl-alkyl; and $R^4$ represents aryl —CH═CH—, wherein aryl can be mono-, di-, tri-, or tetra-substituted, wherein the substituents are independently selected from halogen, alkyl, alkoxy, —$CF_3$, —$OCF_3$, hydroxy, and cyano; pyridyl —CH═CH—, wherein pyridyl can be mono-, di-, or tri-substituted, wherein the substituents are independently selected from halogen, alkyl, alkoxy, —$CF_3$, —$OCF_3$, hydroxy, and cyano; pyrimidinyl —CH═CH—; furanyl —CH═CH—; or thienyl —CH═CH—.

In another especially preferred embodiment, the present invention relates to a compound of formula I, wherein X represents —$CH_2$— or a bond;

n represents the integer 1;

$R^1$ represents alkyl; cycloalkyl (preferably cyclopropyl); hydroxy-ethyl; benzo[1,3]dioxolyl; phenyl that can be mono-substituted with halogen, alkyl, alkoxy, —$CF_3$, or alkyl-carbonyl, or phenyl that is di- or tri-substituted, wherein the substituents are independently selected from alkyl (especially methyl) and halogen; pyridyl that can be mono-substituted with halogen, alkyl, or —$CF_3$; furanyl that can be mono-substituted with methyl, hydroxy-methyl, or bromine, or furanyl that is di-substituted with alkyl (especially methyl); thienyl that can be mono-substituted with methyl or chlorine; pyrimidinyl; isoquinolinyl; benzhydryl; imidazolyl optionally mono-substituted with alkyl (especially methyl); or thiazolyl; or X represents —C(═O)— and $R^1$ represents hydrogen;

$R^2$ represents indolyl; imidazolyl optionally mono-substituted with alkyl (especially methyl); phenyl that can be mono-substituted with halogen, alkyl, hydroxy, or cyano, or phenyl that is di-substituted with halogen; pyridyl; benzothienyl; thiazolyl; or thienyl;

$R^3$ represents indolyl; pyridyl that can be mono-substituted with alkoxy, alkoxy-alkoxy, —$NR^{31}R^{32}$, morpholino, piperidino, oxo-piperidinyl, oxo-pyrrolidinyl, pyridyl, or phenyl; or phenyl which is mono-substituted with phenyl, pyridyl, alkyl, alkoxy, dialkyl-amino, morpholino, N-benzyl-N-alkyl-amino, (dialkyl-amino)-alkoxy, phenyl-alkoxy, or tetrahydro-isoquinolinyl;

or $R^3$ represents the following group:

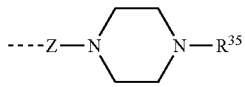

wherein Z represents phenyl or pyridyl;

$R^{31}$ represents 2-$C_{1-5}$-alkoxyethyl, phenyl, pyridyl, phenyl-alkyl, hydroxyalkyl-carbonyl, alkyl-carbonyl, cycloalkyl-carbonyl, or phenyl-carbonyl;

$R^{32}$ represents hydrogen or methyl;

$R^{35}$ represents alkyl, alkyl-carbonyl, phenyl, pyridyl, or pyrimidinyl; and $R^4$ represents phenyl —CH═CH— (the configuration at the double bond being preferably trans), wherein phenyl can be mono-, di-, or tri-substituted, wherein the substituents are independently selected from halogen, alkyl, alkoxy (especially methoxy), and —$CF_3$; or phenyl —$CH_2$—$CH_2$—, wherein phenyl is di-substituted with —$CF_3$.

Preferred compounds of formula I are:

N—[(S)-1-benzyl-2-(4-benzyl-piperazin-1-yl)-2-oxo-ethyl]-N-(4-pentyl-benzyl)-3-(4-trifluoromethyl-phenyl)-acrylamide, N—[(S)-1-benzyl-2-(4-benzyl-piperazin-1-yl)-2-oxo-ethyl]-N-(4-pentyl-benzyl)-3-(3-trifluoromethyl-phenyl)-acrylamide, N—[(S)-1-benzyl-2-(4-benzyl-piperazin-1-yl)-2-oxo-ethyl]-N-(4-pentyl-benzyl)-3-(2-trifluoromethyl-phenyl)-acrylamide, N—[(S)-1-benzyl-2-(4-benzyl-piperazin-1-yl)-2-oxo-ethyl]-3-(4-methoxy-phenyl)-N-(4-pentyl-benzyl)-acrylamide, N—[(S)-1-benzyl-2-(4-benzyl-piperazin-1-yl)-2-oxo-ethyl]-3-(3-methoxy-phenyl)-N-(4-pentyl-benzyl)-acrylamide, and N—[(S)-1-benzyl-2-(4-benzyl-piperazin-1-yl)-2-oxo-ethyl]-3-(3,5-bis-trifluoromethyl-phenyl)-N-(4-pentyl-benzyl)-propionamide.

Further preferred compounds of formula I are:

N—[(S)-1-Benzyl-2-(4-benzyl-piperazin-1-yl)-2-oxo-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-pyridin-4-yl-benzyl)-3-(4-trifluoromethyl-phenyl)-acrylamide, N—[(S)-1-Benzyl-2-(4-benzyl-piperazin-1-yl)-2-oxo-ethyl]-N-(4-pyridin-3-yl-benzyl)-3-(4-trifluoromethyl-phenyl)-acrylamide, N—[(S)-1-Benzyl-2-(4-benzyl-piperazin-1-yl)-2-oxo-ethyl]-N-[4-(4-pyridin-2-yl-piperazin-1-yl)-benzyl]-3-(4-trifluoromethyl-phenyl)-acrylamide, N—[(S)-1-Benzyl-2-(4-benzyl-piperazin-1-yl)-2-oxo-ethyl]-N-(4-benzyloxy-benzyl)-3-(4-trifluoromethyl-phenyl)-acrylamide, N—[(S)-1-Benzyl-2-(4-benzyl-piperazin-1-yl)-2-oxo-ethyl]-N-[4-(4-pyrimidin-2-yl-piperazin-1-yl)-benzyl]-3-(4-trifluoromethyl-phenyl)-acrylamide, N-[4-(4-Acetyl-piperazin-1-yl)-benzyl]-N—[(S)-1-benzyl-2-(4-benzyl-piperazin-1-yl)-2-oxo-ethyl]-3-(4-trifluoromethyl-phenyl)-acrylamide, N—[(S)-1-Benzyl-2-(4-benzyl-piperazin-1-yl)-2-oxo-ethyl]-N-[6-(4-pyrimidin-2-yl-piperazin-1-yl)-pyridin-3-ylmethyl]-3-(4-trifluoromethyl-phenyl)-acrylamide, N—[(S)-1-Benzyl-2-(4-furan-2-ylmethyl-piperazin-1-yl)-2-oxo-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-ethoxy-benzyl)-3-(4-trifluoromethyl-phenyl)-acrylamide, N—[(S)-1-Benzyl-2-(4-benzyl-piperazin-1-yl)-2-oxo-ethyl]-N-(4-ethoxy-benzyl)-3-(4-trifluoromethyl-phenyl)-acrylamide, N-[(S)-1-Benzyl-2-oxo-2-(4-thiophen-2-ylmethyl-piperazin-1-yl)-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(4-trifluoromethyl-phenyl)-acrylamide, N—{(S)-1-Benzyl-2-[4-(4-methyl-benzyl)-piperazin-1-yl]-2-oxo-ethyl}-N-(4-pyridin-2-yl-benzyl)-3-(4-trifluoromethyl-phenyl)-acrylamide, N—{(S)-1-Benzyl-2-[4-(4-ethyl-benzyl)-piperazin-1-yl]-2-oxo-ethyl}-N-(4-pyridin-2-yl-benzyl)-3-(4-trifluoromethyl-phenyl)-acrylamide, N—{(S)-1-Benzyl-2-[4-(3H-imidazol-4-ylmethyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-[2,4']bipyridinyl-5-ylmethyl-3-(4-trifluoromethyl-phenyl)-acrylamide, N—{(S)-1-Benzyl-2-[4-(4-isopropyl-benzyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-oxo-2-(4-thiazol-2-ylmethyl-piperazin-1-yl)-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-pyridin-2-yl-benzyl)-3-p-tolyl-acrylamide, N—[(S)-1-Benzyl-2-oxo-2-(4-pyridin-3-ylmethyl-piperazin-1-yl)-ethyl]-N-(4-pyridin-2-yl-benzyl)-3-(4-trifluoromethyl-phenyl)-acrylamide, N—[(S)-1-Benzyl-2-oxo-2-(4-thiophen-3-ylmethyl-piperazin-1-yl)-ethyl]-N-(4-pyridin-2-yl-benzyl)-3-(4-trifluoromethyl-phenyl)-acrylamide, N—{(S)-1-Benzyl-2-[4-(2,3-difluoro-4-methyl-benzyl)-piperazin-1-yl]-2-oxo-ethyl}-N-(4-pyridin-2-yl-benzyl)-3-(4-trifluoromethyl-phenyl)-acrylamide, N—{(S)-1-Benzyl-2-[4-(3,4-dimethyl-benzyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-oxo-2-(4-pyrimidin-5-ylmethyl-piperazin-1-yl)-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-ethoxy-benzyl)-3-(4-methoxy-phenyl)-acrylamide, N—[(S)-1-Benzyl-2-oxo-2-(4-pyridin-2-ylmethyl-piperazin-1-yl)-ethyl]-N-(4-pyridin-2-yl-benzyl)-3-(4-trifluoromethyl-phenyl)-acrylamide, N—{(S)-1-Benzyl-2-[4-(3-methyl-benzyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-p-tolyl-acrylamide, N—{(S)-1-Benzyl-2-oxo-2-[4-(4-trifluoromethyl-benzyl)-piperazin-1-yl]-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-3-(4-bromo-phenyl)-N-(4-pyridin-2-yl-benzyl)-acrylamide, N—[(S)-1-Benzyl-2-(4-benzyl-piperazin-1-yl)-2-oxo-ethyl]-3-(4-bromo-phenyl)-N-(4-ethyl-benzyl)-acrylamide, N—[(S)-1-Benzyl-2-(4-benzyl-piperazin-1-yl)-2-oxo-ethyl]-N-(4-ethyl-benzyl)-3-(3-fluoro-4-methoxy-phenyl)-acrylamide, N—[(S)-1-Benzyl-2-(4-benzyl-piperazin-1-yl)-2-oxo-ethyl]-N-(4-pyridin-2-yl-benzyl)-3-(6-trifluoromethyl-pyridin-3-yl)-acrylamide, N—[(S)-1-Benzyl-2-(4-benzyl-piperazin-1-yl)-2-oxo-ethyl]-N-(4-ethyl-benzyl)-3-(4-methoxy-2,3-dimethyl-phenyl)-acrylamide, N—[(S)-1-Benzyl-2-(4-benzyl-piperazin-1-yl)-2-oxo-ethyl]-N-[2,3']bipyridinyl-5-ylmethyl-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(4-methoxy-3-methyl-phenyl)-acrylamide, N—[(S)-1-Benzyl-2-(4-benzyl-piperazin-1-yl)-2-oxo-ethyl]-N-[4-(3-dimethylamino-propoxy)-benzyl]-3-(4-trifluoromethyl-phenyl)-acrylamide, N—{(S)-1-Benzyl-2-[4-(6-methoxy-pyridin-3-ylmethyl)-piperazin-1-yl]-2-oxo-ethyl}-N-(4-pentyl-benzyl)-3-(4-trifluoromethyl-phenyl)-acrylamide, N—[(S)-1-Benzyl-2-(4-benzyl-piperazin-1-yl)-2-oxo-ethyl]-3-(3,5-dimethoxy-phenyl)-N-(4-ethyl-benzyl)-acrylamide, N—[(S)-1-Benzyl-2-(4-benzyl-piperazin-1-yl)-2-oxo-ethyl]-3-(3-fluoro-4-methoxy-phenyl)-N-(4-pyridin-2-yl-benzyl)-acrylamide, N—[(S)-1-Benzyl-2-(4-benzyl-piperazin-1-yl)-2-oxo-ethyl]-N-[4-(3,4-dihydro-1H-isoquinolin-2-yl)-benzyl]-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(3-fluoro-4-trifluoromethyl-phenyl)-acrylamide, N—[(S)-1-Benzyl-2-(4-benzyl-piperazin-1-yl)-2-oxo-ethyl]-N-pyridin-3-ylmethyl-3-(4-trifluoromethyl-phenyl)-acrylamide, N—[(S)-1-Benzyl-2-(4-benzyl-piperazin-1-yl)-2-oxo-ethyl]-N-[4-(3-dimethylamino-propoxy)-benzyl]-3-(4-methoxy-phenyl)-acrylamide, N-Benzyl-N—[(S)-1-benzyl-2-(4-benzyl-piperazin-1-yl)-2-oxo-ethyl]-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(2-fluoro-4-trifluoromethyl-phenyl)-acrylamide, N-[2-(4-Benzyl-piperazin-1-yl)-(S)-1-(4-chloro-benzyl)-2-oxo-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-morpholin-4-yl-benzyl)-3-(4-trifluoromethyl-phenyl)-acrylamide, N—[(S)-1-Benzyl-2-oxo-2-(4-pyridin-4-ylmethyl-piperazin-1-yl)-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-[6-(4-pyridin-2-yl-piperazin-1-yl)-pyridin-3-ylmethyl]-3-(4-trifluoromethyl-phenyl)-acrylamide, N—{(S)-1-Benzyl-2-[4-(1H-imidazol-2-ylmethyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(4-methoxy-phenyl)-acrylamide, N-[2-(4-Benzyl-piperazin-1-yl)-2-oxo-(S)-1-pyridin-2-ylmethyl-ethyl]-N-(4-pyridin-2-yl-benzyl)-3-(4-trifluoromethyl-phenyl)-acrylamide, N—{(S)-1-Benzyl-2-[4-(6-methyl-pyridin-2-ylmethyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(6-morpholin-4-yl-pyridin-3-ylmethyl)-3-(4-trifluoromethyl-phenyl)-acrylamide, N—[(S)-1-Benzyl-2-(4-benzyl-piperazin-1-yl)-2-oxo-ethyl]-N-[6-(2-oxo-pyrrolidin-1-yl)-pyridin-3-ylmethyl]-3-(4-trifluoromethyl-phenyl)-acrylamide, N—[(S)-1-Benzyl-2-(4-benzyl-piperazin-1-yl)-2-oxo-ethyl]-N-(6-phenyl-pyridin-3-ylmethyl)-3-(4-trifluoromethyl-phenyl)-acrylamide, N-[6-(4-Acetyl-piperazin-1-yl)-pyridin-3-ylmethyl]-N—[(S)-1-benzyl-2-(4-benzyl-piperazin-1-yl)-2-oxo-ethyl]-3-(4-trifluoromethyl-phenyl)-acrylamide, N—[(S)-1-Benzyl-2-(4-benzyl-piperazin-1-yl)-2-oxo-ethyl]-N-[4-(4-phenyl-piperazin-1-yl)-benzyl]-3-(4-trifluoromethyl-phenyl)-acrylamide, N—[(S)-1-Benzyl-2-(4-benzyl-piperazin-1-yl)-2-oxo-ethyl]-N-thiophen-3-ylmethyl-3-(4-trifluoromethyl-phenyl)-acrylamide, N—{(S)-1-Benzyl-2-[4-(3,5-dimethyl-benzyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-3-(4-fluoro-phenyl)-N-(4-pyridin-2-yl-benzyl)-acrylamide, N—[(S)-1-Benzyl-2-(4-benzyl-piperazin-1-yl)-2-oxo-ethyl]-N-(4-ethyl-benzyl)-3-(4-fluoro-phenyl)-acrylamide, N—[(S)-1-Benzyl-2-(4-benzyl-piperazin-1-yl)-2-oxo-ethyl]-N-[6-(2-hydroxy-acetylamino)-pyridin-3-ylmethyl]-3-(4-trifluoromethyl-phenyl)-acrylamide, N-[2-(4-Benzyl-piperazin-1-yl)-2-oxo-(S)-1-thiazol-4-ylmethyl-ethyl]-N-(4-pyridin-2-yl-benzyl)-3-(4-trifluoromethyl-phenyl)-acrylamide, N—[(S)-1-Benzyl-2-(4-methyl-piperazin-1-yl)-2-oxo-ethyl]-N-(4-pentyl-benzyl)-3-(4-trifluoromethyl-phenyl)-acrylamide, N—[(S)-1-Benzyl-2-(4-benzyl-piperazin-1-yl)-2-oxo-ethyl]-N-[6-(2-methoxy-ethoxy)-pyridin-3-ylmethyl]-3-(4-trifluoromethyl-phenyl)-acrylamide, N—[(S)-1-Benzyl-2-(4-benzyl-piperazin-1-yl)-2-oxo-ethyl]-N-[4-(4-ethyl-piperazin-1-yl)-benzyl]-3-(4-trifluoromethyl-phenyl)-acrylamide, N—[(S)-1-Benzyl-2-(4-benzyl-piperazin-1-yl)-2-oxo-ethyl]-N-(6-methoxy-pyridin-3-ylmethyl)-3-(4-trifluoromethyl-phenyl)-acrylamide, N—[(S)-1-Benzyl-2-(4-benzyl-piperazin-1-yl)-2-oxo-ethyl]-N-thiazol-2-ylmethyl-3-(4-trifluoromethyl-phenyl)-acrylamide, N—{(S)-1-Benzyl-2-[4-(2,3-dimethyl-benzyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-oxo-2-(4-thiophen-2-ylmethyl-piperazin-1-yl)-ethyl]-N-pyridin-3-ylmethyl-3-(4-trifluoromethyl-phenyl)-acrylamide, N—[(S)-1-Benzyl-2-(4-benzyl-piperazin-1-yl)-2-oxo-ethyl]-N-pyridin-4-ylmethyl-3-(4-trifluoromethyl-phenyl)-acrylamide, N—[(S)-1-Benzyl-2-(4-furan-2-ylmethyl-piperazin-1-yl)-2-oxo-ethyl]-N-pyridin-3-ylmethyl-3-(4-trifluoromethyl-phenyl)-acrylamide, N—{(S)-1-Benzyl-2-[4-(2,4-dimethyl-benzyl)-piperazin-1-yl]-2-oxo-ethyl}-N-(4-pyridin-2-yl-benzyl)-3-(4-trifluoromethyl-phenyl)-acrylamide, N-[2-(4-Benzyl-piperazin-1-yl)-2-oxo-1-thiazol-2-ylmethyl-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-[6-(2-methoxy-ethylamino)-pyridin-3-ylmethyl]-3-(4-trifluoromethyl-phenyl)-acrylamide, N—[(S)-1-Benzyl-2-(4-benzyl-piperazin-1-yl)-2-oxo-ethyl]-N-(6-ethoxy-pyridin-3-ylmethyl)-3-(4-trifluoromethyl-phenyl)-acrylamide, N—[(S)-1-Benzyl-2-(4-benzyl-piperazin-1-yl)-2-oxo-ethyl]-N-{6-[(2-hydroxy-ethyl)-methyl-amino]-pyridin-3-ylmethyl}-3-(4-trifluoromethyl-phenyl)-acrylamide, and N—[(S)-1-Benzyl-2-(4-benzyl-piperazin-1-yl)-2-oxo-ethyl]-3-(2-fluoro-4-trifluoromethyl-phenyl)-N-(4-pyridin-2-yl-benzyl)-acrylamide.

The compounds of the formula I are useful for the treatment and/or prevention of the diseases mentioned herein, especially malaria.

In one embodiment, the invention relates to a method for the treatment and/or prevention of the diseases mentioned herein, especially malaria, said method comprising administering to a subject a pharmaceutically active amount of a compound of formula I.

A further aspect of the present invention relates to pharmaceutical compositions comprising a compound of formula I and a pharmaceutically acceptable carrier material. These pharmaceutical compositions may be used for the treatment or prevention of the above-mentioned diseases. The pharmaceutical compositions can be used for enteral, parenteral, or topical administration. They can be administered, for example, perorally, e.g. in the form of tablets, coated tablets, dragées, hard and soft gelatine capsules, solutions, emulsions or suspensions, nasal, e.g. in the form of sprays, rectally, e.g. in the form of suppositories, parenterally, e.g. in the form of injection solutions or infusion solutions, or topically, e.g. in the form of ointments, creams or oils.

The invention also relates to the use of a compound of formula I for the preparation of pharmaceutical compositions for the treatment and/or prevention of the above-mentioned diseases.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy,* 20th Edition, Philadelphia College of Pharmacy and Science) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula I or the above-mentioned pharmaceutical compositions may also be used in combination with one or more other therapeutically useful substances e.g. with other antimalarials like quinolines (quinine, chloroquine, amodiaquine, mefloquine, primaquine, tafenoquine), peroxide antimalarials (artemisinin, artemether, artesunate), pyrimethamine-sulfadoxine antimalarials (e.g. Fansidar), hydroxynaphtoquinones (e.g. atovaquone), acroline-type antimalarials (e.g. pyronaridine) and other antiprotozoal agents like ethylstibamine, hydroxystilbamidine, pentamidine, stilbamidine, quinapyramine, puromycine, propamidine, nifurtimox, melarsoprol, nimorazole, nifuroxime, aminitrozole and the like.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

The compounds of the formula I of the present invention may be prepared according to the procedures described herein, especially as described in the experimental part.

In general, all chemical transformations can be performed according to well-known standard methodologies as described in the literature or as described in the procedures below.

Preparation of Compounds of Formula I:

Scheme 1:

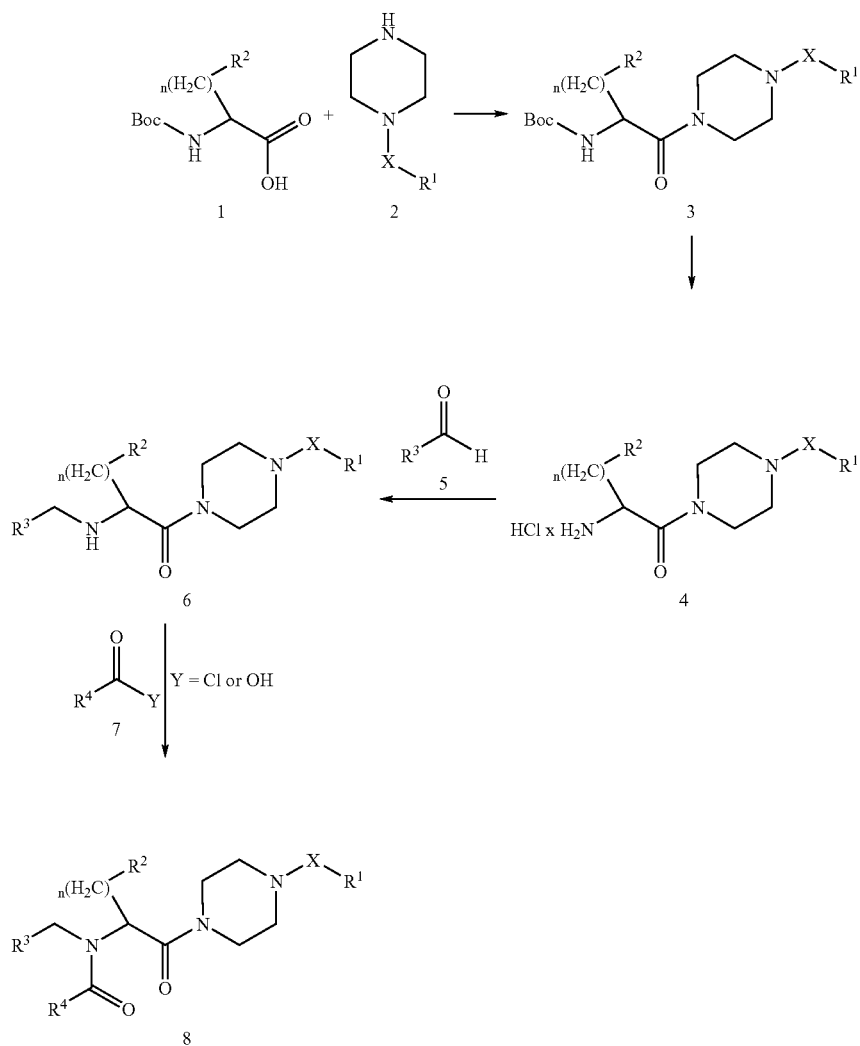

The Boc-protected aminoacid 1 can be coupled with an N-4-substituted piperazine 2 by the help of a coupling/activating reagent such as EDC or TBTU in a solvent such as DCM, DMF or acetonitrile at rt in the presence of a base such as Hünig's base, triethylamine or N-methylmorpholine to give the intermediate 3. Boc-deprotection is usually achieved by reacting 3 with HCl in dioxane to give the HCl-salt of the amine intermediate 4 which can be refluxed with an aldehyde derivative 5 (under reductive amination conditions via the imine; not depicted) in methanol in the presence of a base such as triethylamine to form an unstable imine intermediate which is reduced at rt with sodium borohydride to give the secondary amine intermediate 6. Compound 6 can be acylated by either an acid chloride 7 (Y=Cl) in a suitable solvent like DCM or acetonitrile in the presence of a base such as Hünig's base, or a carboxylic acid 7 (Y=OH) by the help of a coupling/activating reagent such as EDC or TBTU in a solvent such as DCM, DMF or acetonitrile at rt in the presence of a base such as Hünig's base, triethylamine or N-methylmorpholine to give the final compounds 8 of formula I.

The procedure for the preparation of compounds of formula I depicted in scheme 2 starts by a reductive amination of the aminoacid methyl ester 9 with an aldehyde derivative 5 (under conditions similar to those described above) to give the secondary amine intermediate 10 which can be acylated by either an acid chloride 7 (Y=Cl) in a suitable solvent like DCM or acetonitrile in the presence of a base such as Hünig's base, or a carboxylic acid 7 (Y=OH) by the help of a coupling/activating reagent such as EDC or TBTU in a solvent such as DCM, DMF or acetonitrile at rt in the presence of a base such as Hünig's base, triethylamine or N-methylmorpholine to give the intermediate 11. Hydrolysis of the methylester group by a base such as sodium hydroxide in a solvent such as methanol at rt leads to the intermediate carboxylic acid 12. The acid 12 can either be reacted in an acylation reaction under conditions as described above with an N-4-substituted piperazine derivative 2 to give the final compounds 8 of formula I, or compound 12 can be reacted with 1-Boc-piperazine 13 in an acylation reaction under conditions as described above to give intermediate

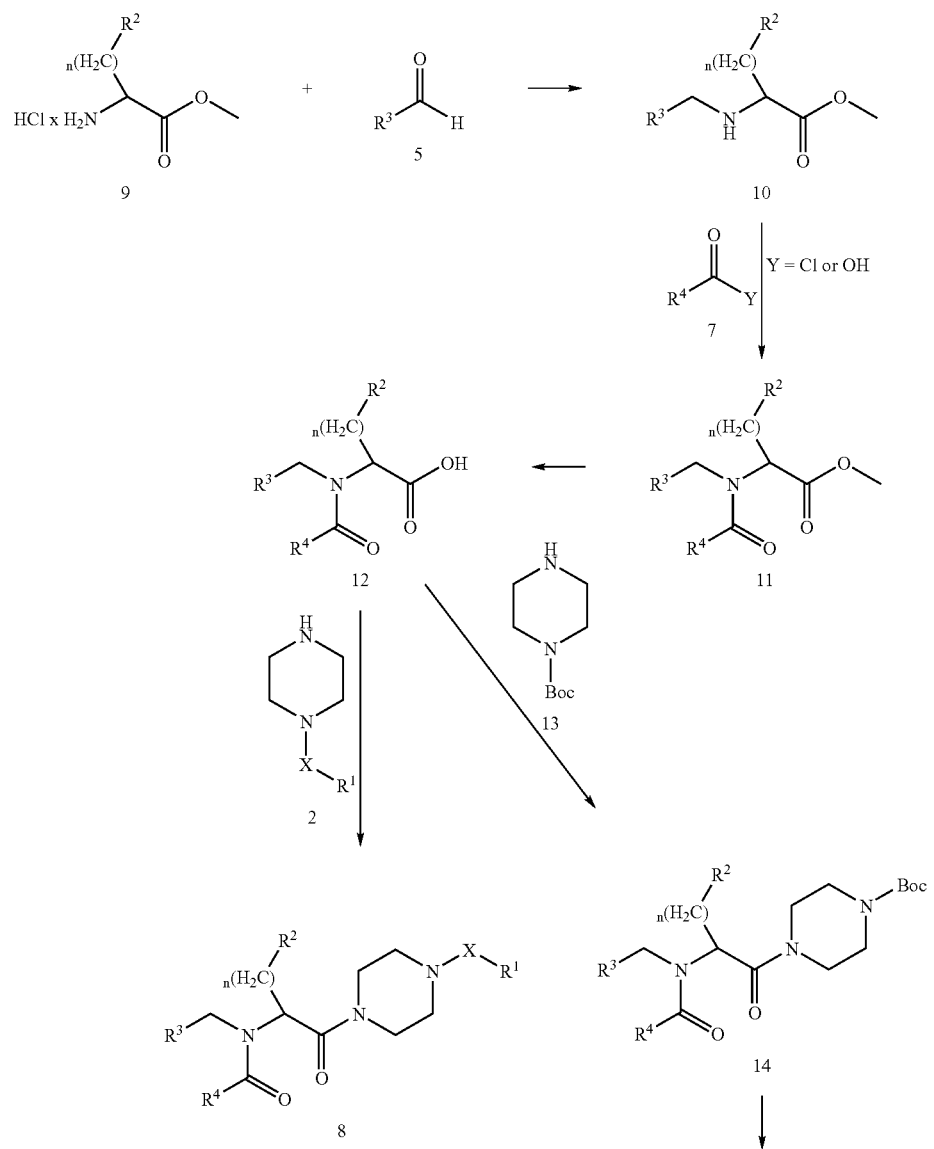

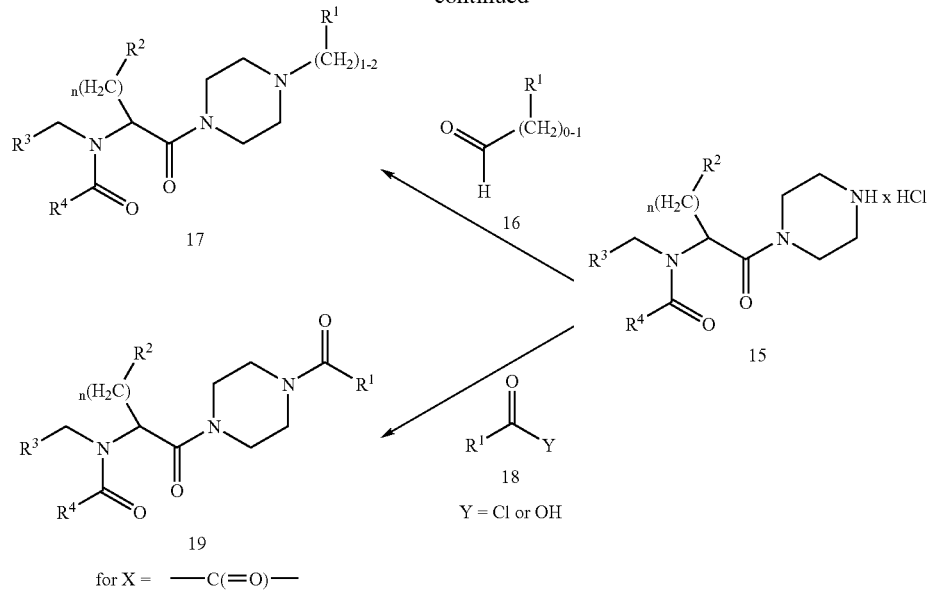

14 which is deprotected under standard conditions with HCl in dioxane to give the amine precursor 15 which is either reacted under reductive amination conditions with an aldehyde derivative 16 in a solvent such as DCM or acetonitrile in the presence of sodium triacetoxyborohydride as the reducing agent to give the final compounds 17 of formula I, or the amine 15 can be acylated with reagent 18 under conditions as described above (depending on the nature of Y) to give the final compounds 19 of formula I.

The following examples illustrate the invention but do not limit the scope thereof. All temperatures are stated in ° C.

Abbreviations (as Used Herein):

aq. aqueous
Boc tert.-butyloxycarbonyl
Bu Butyl
DCM Dichloromethane
DIPEA Diisopropylethylamine
DMF Dimethylformamide
DMSO Dimethylsulfoxide
EDC N-(3-Dimethylaminopropyl)-N'-ethyl-carbodiimid
ELSD Evaporative light-scattering detection
Et Ethyl
EtOAc Ethyl acetate
EtOH Ethanol
Ex Example
Fmoc Fluorenylmethoxycarbonyl
h hour(s)
HPLC High Performance Liquid Chromatography
HV High Vacuum
LC-MS Liquid Chromatography-Mass Spectroscopy
Me Methyl
MeOH Methanol
min minute(s)
MS Mass Spectroscopy
PBS Phosphate buffered saline
prep. preparative
PyBOP Benzotriazole-1-yl-oxy-tris-pyrrolidino-phosphonium hexafluorophosphate
quant. quantitative
rt room temperature
sat. saturated
SK-CC02-A 2-(Dimethylamino)-ferrocen-1-yl-palladium (II)-chloride Dinorbornylphosphine Complex (Fluka 44696)
TBTU O-Benzotriazol-1-yl-N,N,N',N'-tetramethyluronium tetrafluoroborate
TEA Triethylamine
TFA Trifluoroacetic acid
TLC Thin Layer Chromatography
$t_R$ retention time (given in minutes)
UV ultra violet
V is visible

GENERAL PROCEDURES AND EXAMPLES

HPLC Conditions

Analytic: Zorbax 59 SB Aqua column, 4.6×50 mm from Agilent Technologies.
Eluents: A: acetonitrile; B: $H_2O$+0.5% TFA. Gradient: 90% B→5% B over 2 min.
Flow: 1 mL/min. Detection: UV/Vis+MS.
Preparative: Zorbax SB Aqua column, 20×500 mm from Agilent Technologies.
Eluent: A: Acetonitrile; B: $H_2O$+0.05% ammonium hydroxide (25% aq.). Gradient:
80% B→10% B over 6 min. Flow: 40 mL/min. Detection: UV+MS, or UV+ELSD.
Chiral, analytic: Regis Whelk column, 4.6×250 mm, 10 μm. Eluent A: EtOH+0.05% $Et_3N$. Eluent B: hexane. Isocratic conditions, usually 60% B, over 40 min, 1 mL/min. The isocratic mixture may vary, depending on the compounds.
Chiral, preparative: As analytical conditions, but on a Regis Whelk 01 column, 50×250 mm and a flow of 100 mL/min.

Example 1

Step 1

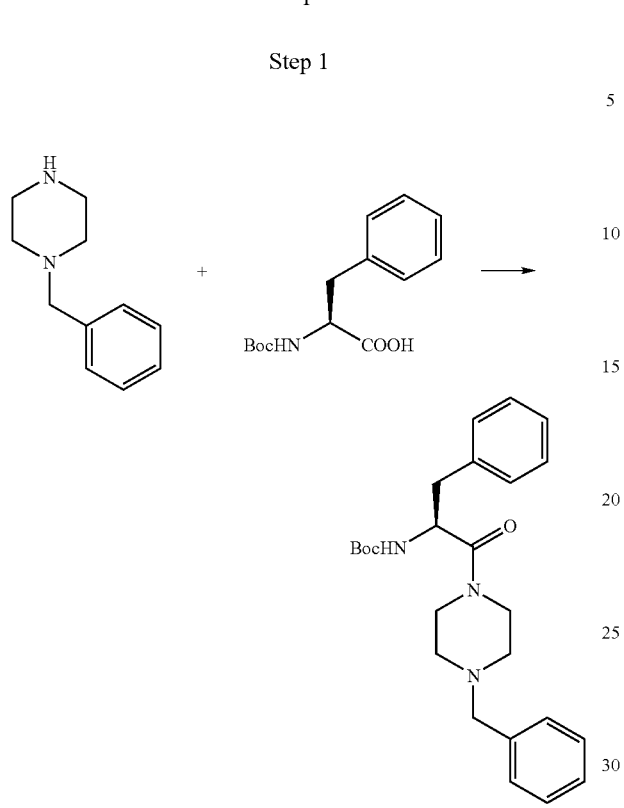

(S)-2-tert-Butoxycarbonylamino-3-phenyl-propionic acid (3 g, 11.3 mmol) was dissolved in DMF (100 mL), and PyBOP (5.9 g, 11.3 mmol) and Hünig's base (3.36 g, 25.99 mmol) were added, followed by 1-benzyl-piperazine (2 g, 11.3 mmol). Stirring at rt was continued for 8 h, followed by the addition of EtOAc (400 mL). The mixture was washed with 1 N aq. HCl (300 mL), sat. aq. sodium hydrogencarbonate solution (300 mL) and brine (300 mL). The organic layer was dried over magnesium sulfate, filtered and concentrated under reduced pressure to give 4.375 g (91%) of [(S)-1-benzyl-2-(4-benzyl-piperazin-1-yl)-2-oxo-ethyl]-carbamic acid tert-butyl ester. LC-MS: $t_R$=0.80 min; $[M+H]^+$=424.34.

Step 2

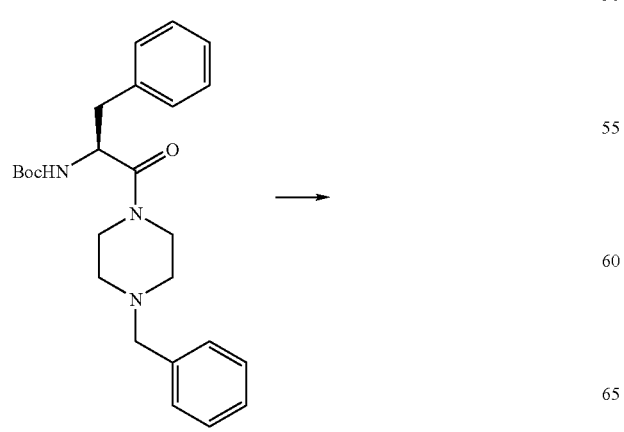

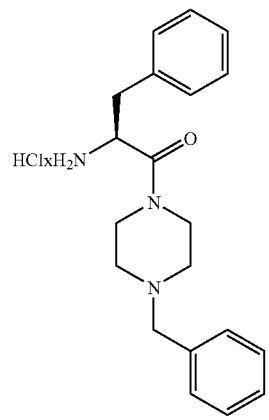

[(S)-1-Benzyl-2-(4-benzyl-piperazin-1-yl)-2-oxo-ethyl]-carbamic acid tert-butyl ester (2.5 g, 5.9 mmol) was dissolved in dioxane (20 mL), followed by the addition of 4 M HCl in dioxane (30 mL). The mixture was stirred at rt for 1 h, the solvent removed under reduced pressure and the residue dried under HV to give 2.2 g (quant. yield) of N—[(S)-1-benzyl-2-(4-benzyl-piperazin-1-yl)-2-oxo-ethyl]-N-(4-pentyl-benzyl)-3-(4-trifluoromethyl-phenyl)-acrylamide hydrochloride. LC-MS: $t_R$=0.56 min; $[M+H]^+$=324.26.

Step 3

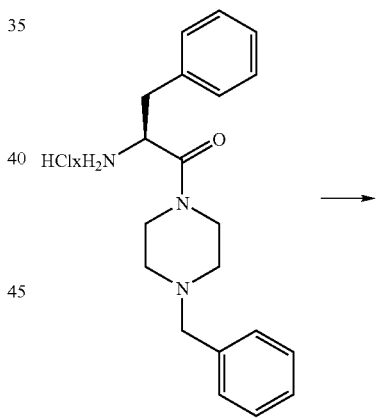

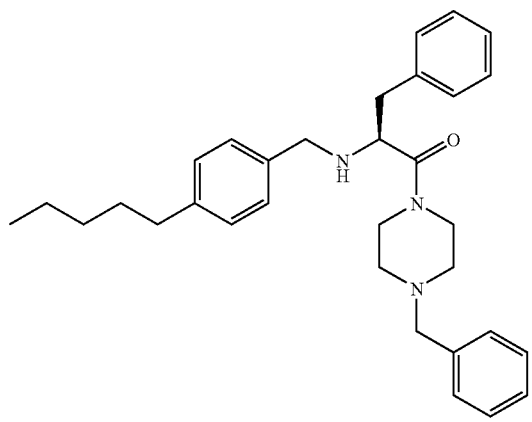

N—[(S)-1-Benzyl-2-(4-benzyl-piperazin-1-yl)-2-oxo-ethyl]-N-(4-pentyl-benzyl)-3-(4-trifluoromethyl-phenyl)-acrylamide hydrochloride (2 g, 5.55 mmol) was dissolved in methanol (50 mL), followed by the addition of triethylamine (0.562 g, 5.55 mmol) and 4-n-pentylbenzaldehyde (1.076 g, 6.10 mmol). The mixture was heated to reflux for 5 h, cooled to rt and sodium borohydride (0.6 g, 15.8 mmol) was added in several portions over a period of 60 min. Stirring at rt was continued for 12 h, followed by the addition of water (2 mL). The mixture was concentrated under reduced pressure, to the residue was added water (100 mL) and the product was extracted with EtOAc (3×100 mL). The combined organic layers were washed with brine (100 mL), dried over magnesium sulfate, filtered and concentrated under reduced pressure. The crude material was purified by column chromatography (silicagel, heptane/EtOAc=1/1) to give 906 mg (32%) of 1-(4-benzyl-piperazin-1-yl)-(S)-2-(4-pentyl-benzylamino)-3-phenyl-propan-1-one. LC-MS: $t_R$=0.77 min; [M+H]$^+$=484.44.

Step 4

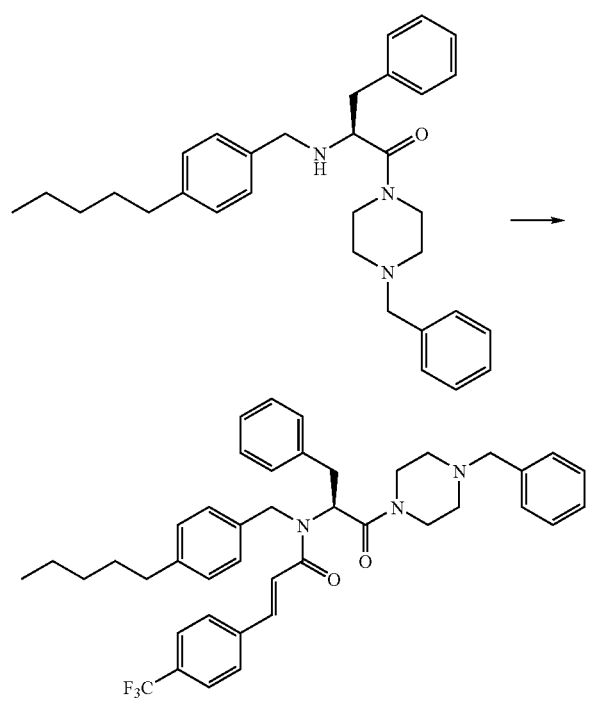

In an inert atmosphere, trans-4-trifluoromethyl-cinnamic acid (21.4 mg, 0.099 mmol) was dissolved in 2 mL dichloromethane followed by the addition of 1-chloro-N,N-2-trimethylpropenyl amine (16.4 μl, 0.122 mmol). Stirring was continued at rt for 1 h. This solution was then added to a solution of 1-(4-benzyl-piperazin-1-yl)-(S)-2-(4-pentyl-benzylamino)-3-phenyl-propan-1-one (43.5 mg, 0.09 mmol) in dichloromethane (1 mL) and Hünig's base (39 μl). The resulting mixture was stirred for 1 h at rt, followed by the addition of water (3 mL). The layers were separated. The aq. layer was extracted with dichloromethane (2×2 mL) and the combined organic layers were dried over magnesium sulfate, filtered and concentrated under reduced pressure. The crude product was purified by prep. TLC (silicagel, heptane/EtOAc=1/1) to give 36.1 mg (58%) of N—[(S)-1-benzyl-2-(4-benzyl-piperazin-1-yl)-2-oxo-ethyl]-N-(4-pentyl-benzyl)-3-(4-trifluoromethyl-phenyl)-acrylamide. LC-MS: $t_R$=1.02 min; [M+H]$^+$=682.48.

According to the procedures described above the following examples could be prepared:

Example 2

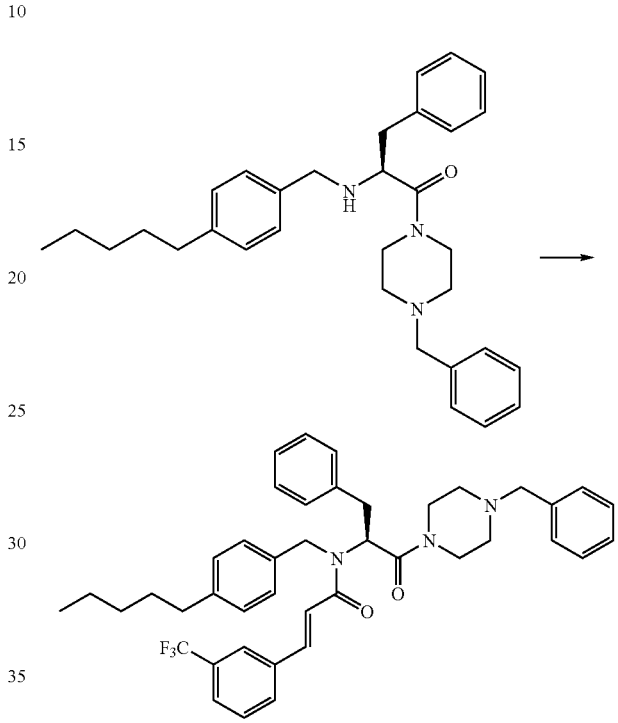

Acylation of 1-(4-benzyl-piperazin-1-yl)-(S)-2-(4-pentyl-benzylamino)-3-phenyl-propan-1-one (43.5 mg, 0.09 mmol) according to the procedure described for the preparation of Example 1 with trans-3-trifluoromethyl-cinnamic acid (21.4 mg, 0.099 mmol) gave 42.9 mg (69%) of N—[(S)-1-benzyl-2-(4-benzyl-piperazin-1-yl)-2-oxo-ethyl]-N-(4-pentyl-benzyl)-3-(3-trifluoromethyl-phenyl)-acrylamide. LC-MS: $t_R$=1.02 min; [M+H]$^+$=682.48.

Example 3

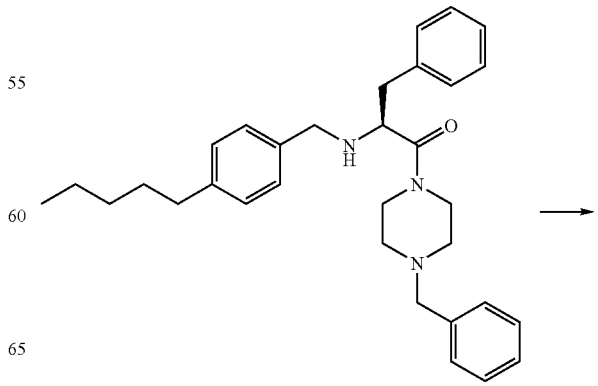

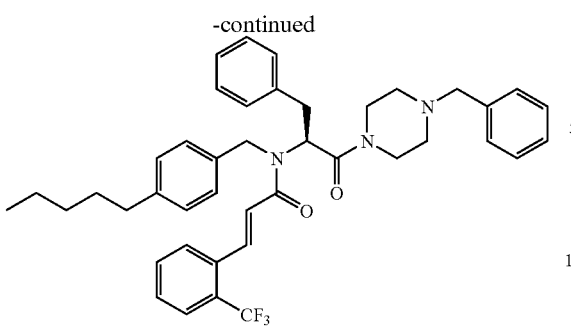

Acylation of 1-(4-benzyl-piperazin-1-yl)-(S)-2-(4-pentyl-benzylamino)-3-phenyl-propan-1-one (43.5 mg, 0.09 mmol) according to the procedure described for the preparation of Example 1 with trans-2-trifluoromethyl-cinnamic acid (21.4 mg, 0.099 mmol) gave 37.6 mg (60%) of N—[(S)-1-benzyl-2-(4-benzyl-piperazin-1-yl)-2-oxo-ethyl]-N-(4-pentyl-benzyl)-3-(2-trifluoromethyl-phenyl)-acrylamide. LC-MS: $t_R$=1.04 min; [M+H]$^+$=682.49.

Example 4

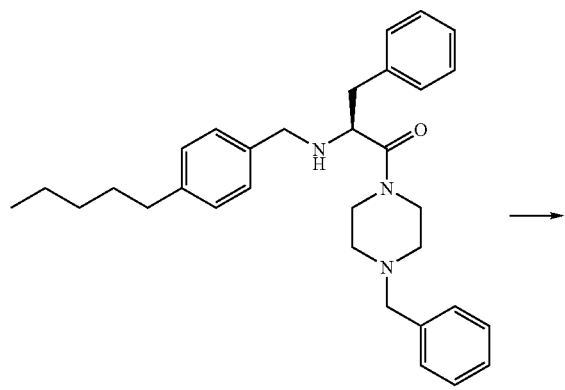

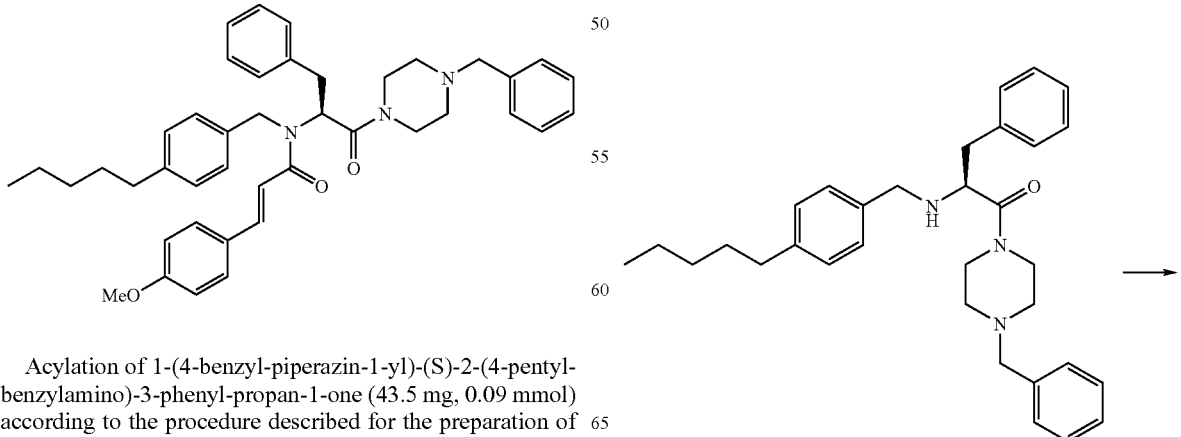

Acylation of 1-(4-benzyl-piperazin-1-yl)-(S)-2-(4-pentyl-benzylamino)-3-phenyl-propan-1-one (43.5 mg, 0.09 mmol) according to the procedure described for the preparation of Example 1 with trans-4-methoxy-cinnamic acid (17.6 mg, 0.099 mmol) gave 27.7 mg (48%) of N—[(S)-1-benzyl-2-(4-benzyl-piperazin-1-yl)-2-oxo-ethyl]-3-(4-methoxy-phenyl)-N-(4-pentyl-benzyl)-acrylamide. LC-MS: $t_R$=1.00 min; [M+H]$^+$=644.50.

Example 5

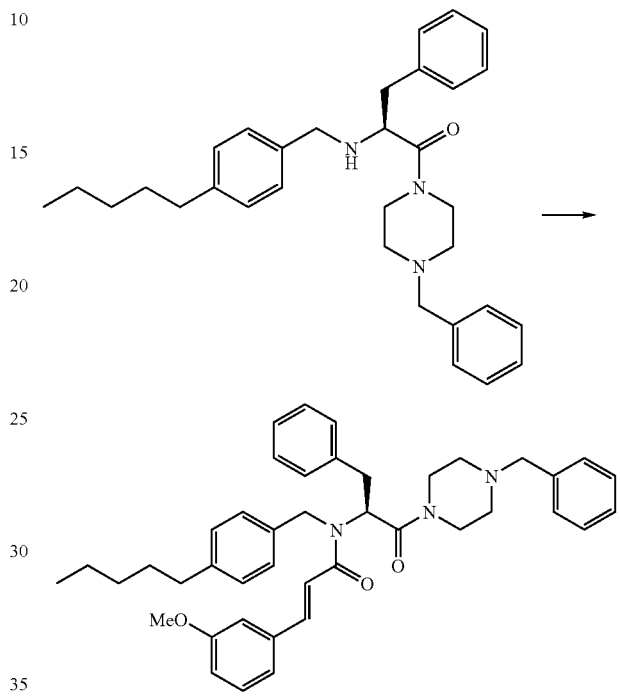

Acylation of 1-(4-benzyl-piperazin-1-yl)-(S)-2-(4-pentyl-benzylamino)-3-phenyl-propan-1-one (43.5 mg, 0.09 mmol) according to the procedure described for the preparation of Example 1 with trans-3-methoxy-cinnamic acid (17.6 mg, 0.099 mmol) gave 31.3 mg (54%) of N—[(S)-1-benzyl-2-(4-benzyl-piperazin-1-yl)-2-oxo-ethyl]-3-(3-methoxy-phenyl)-N-(4-pentyl-benzyl)-acrylamide. LC-MS: $t_R$=1.01 min; [M+H]$^+$=644.50.

Example 6

-continued

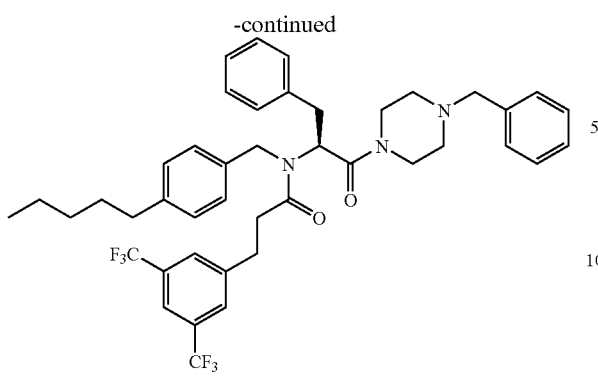

Acylation of 1-(4-benzyl-piperazin-1-yl)-(S)-2-(4-pentyl-benzylamino)-3-phenyl-propan-1-one (43.5 mg, 0.09 mmol) according to the procedure described for the preparation of Example 1 with 3,5-bis-trifluoromethyl-hydrocinnamic acid (28.33 mg, 0.099 mmol) gave 55.5 mg (82%) of N—[(S)-1-benzyl-2-(4-benzyl-piperazin-1-yl)-2-oxo-ethyl]-3-(3,5-bis-trifluoromethyl-phenyl)-N-(4-pentyl-benzyl)-propionamide. LC-MS: $t_R$=1.05 min; $[M+H]^+$=752.45.

Example 7

Step 1

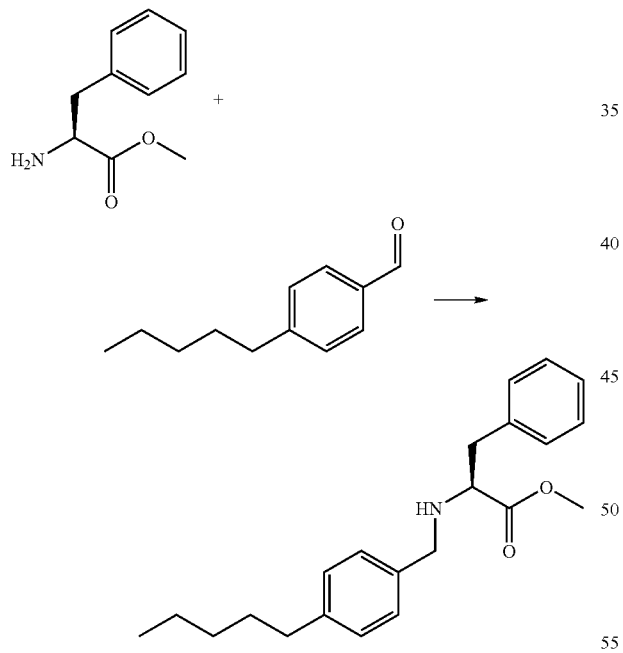

In an inert atmosphere L-phenylalanine methylester hydrochloride (5 g, 23.2 mmol) was dissolved in MeOH (100 mL) followed by the addition of TEA (3.2 mL, 23.2 mmol) and 4-n-pentylbenzaldehyde (4.0 g, 23.2 mmol). The mixture was refluxed for 4 h, cooled to rt, followed by the addition of sodium borohydride (1.3 g, 34.8 mmol) in portions. Stirring was continued for 20 min, then sat. sodium hydrogen carbonate (aq.) (100 mL) was added and the product was extracted with EtOAc (2×100 mL). The combined organic layers were washed with brine (150 mL), dried over magnesium sulfate, filtered and the solvent was evaporated to give 7.35 g (93%) of 2-(4-pentyl-benzylamino)-(S)-3-phenyl-propionic acid methyl ester as a slightly yellow oil. LC-MS: $t_R$=0.89 min; $[M+H]^+$=340.31.

Step 2

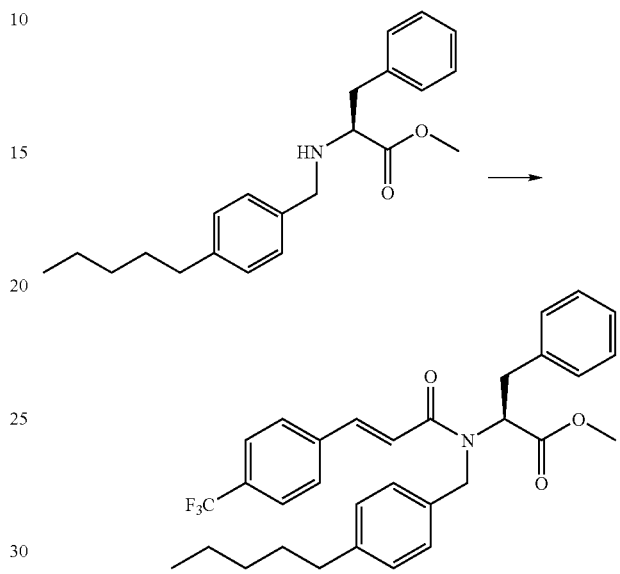

In an inert atmosphere trans-4-(trifluoromethyl)-cinnamic acid (6.7 g, 31.2 mmol) was dissolved in DCM (150 mL) and 1-chloro-N,N,2-trimethylpropenylamine (4.7 g, 35.5 mmol) was slowly added via syringe. Stirring was continued for 1 h followed by the addition of DIPEA (10.7 mL, 62.6 mmol) and 2-(4-pentyl-benzylamino)-(S)-3-phenyl-propionic acid methyl ester (7.0 g, 20.8 mmol). Stirring was continued for 45 min. Water (250 mL) was added and the product was extracted with DCM (3×150 mL). The combined organic layers were dried over magnesium sulfate, filtered and the solvent was evaporated under reduced pressure to give the crude product which was purified by column chromatography (silicagel, EtOAc/heptane=¼) to give 6.71 g (59%) of 2-{(4-pentyl-benzyl)-[3-(4-trifluoromethyl-phenyl)-acryloyl]-amino}-(S)-3-phenyl-propionic acid methyl ester. LC-MS: $t_R$=1.21 min; $[M+H]^+$=538.38.

Step 3

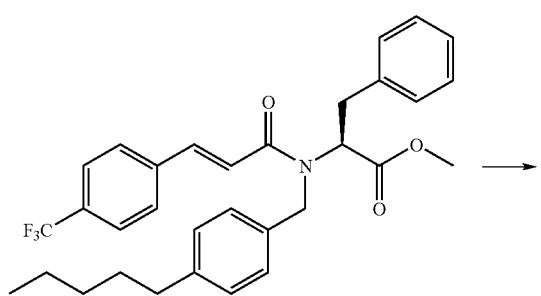

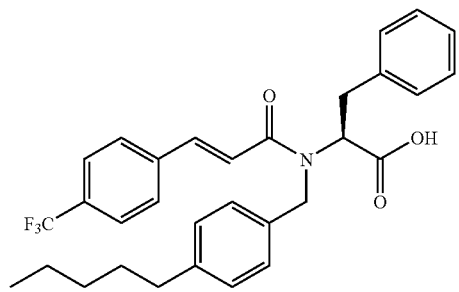

2-{(4-pentyl-benzyl)-[3-(4-trifluoromethyl-phenyl)-acryloyl]-amino}-(S)-3-phenyl-propionic acid methyl ester (6.6 g, 12.3 mmol) was dissolved in MeOH (150 mL) and 1M NaOH$_{aq}$. (25 mL) was added. Stirring was continued for 1 h. A solution of 10% citric acid was added till the pH=6, followed by removal of the MeOH under reduced pressure and the addition of NaCl (solid) to saturate the solution. The product was extracted with EtOAc (2×150 mL). The combined organic layers were dried over magnesium sulfate, filtered and the solvent was evaporated under reduced pressure to give 6.55 g (quant. yield) of 2-{(4-pentyl-benzyl)-[3-(4-trifluoromethyl-phenyl)-acryloyl]-amino}-(S)-3-phenyl-propionic acid. LC-MS: $t_R$=1.16 min; [M+H]$^+$=524.38.

Step 4

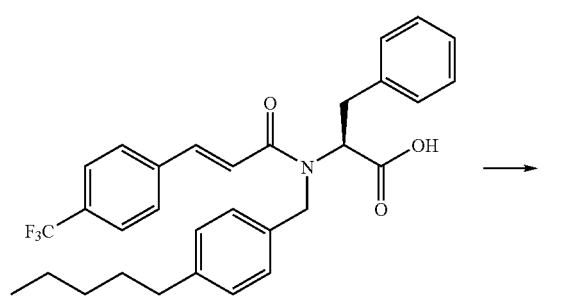

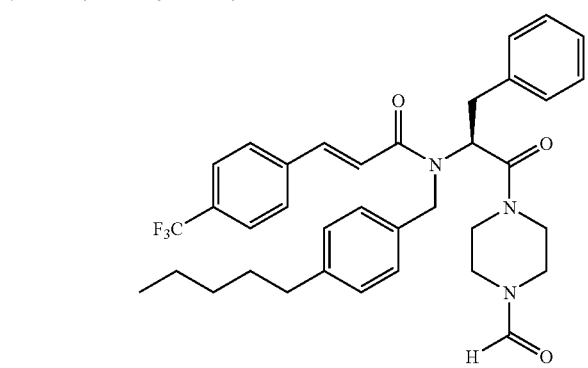

2-{(4-pentyl-benzyl)-[3-(4-trifluoromethyl-phenyl)-acryloyl]-amino}-(S)-3-phenyl-propionic acid (50 mg, 0.095 mmol) was dissolved in acetonitrile (1.0 ml), TBTU (37 mg, 0.115 mmol), DIPEA (37 mg, 0.29 mmol) and 1-formylpiperazine (12.23 mg, 0.105 mmol) was added and the mixture was stirred for 16 h at rt, filtered and directly purified by prep. HPLC to give 32 mg of N—[(S)-1-benzyl-2-(4-formyl-piperazin-1-yl)-2-oxo-ethyl]-N-(4-pentyl-benzyl)-3-(4-trifluoromethyl-phenyl)-acrylamide. LC-MS: $t_R$=1.17 min; [M+H]$^+$=620.50.

Example 8

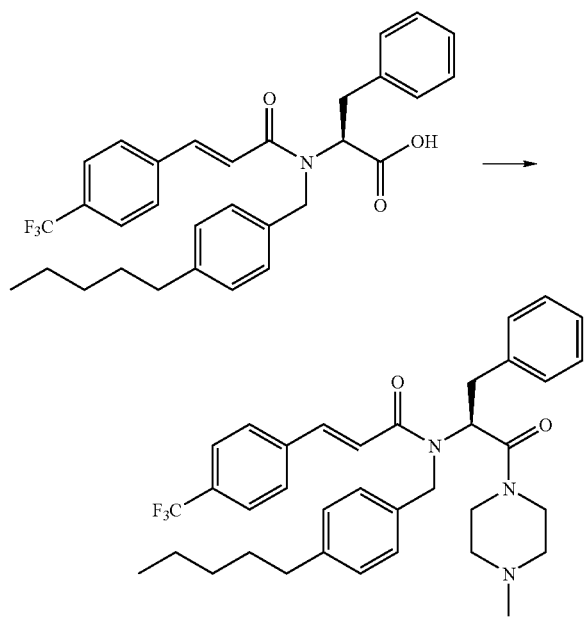

2-{(4-pentyl-benzyl)-[3-(4-trifluoromethyl-phenyl)-acryloyl]-amino}-(S)-3-phenyl-propionic acid (50 mg, 0.095 mmol) was dissolved in acetonitrile (1.0 mL), TBTU (37 mg, 0.115 mmol), DIPEA (37 mg, 0.29 mmol) and 1-methylpiperazine (10.6 mg, 0.105 mmol) was added and the mixture was stirred for 16 h at rt, filtered and directly purified by prep. HPLC to give 28 mg of N—[(S)-1-benzyl-2-(4-methyl-piperazin-1-yl)-2-oxo-ethyl]-N-(4-pentyl-benzyl)-3-(4-trifluoromethyl-phenyl)-acrylamide. LC-MS: $t_R$=1.00 min; [M+H]$^+$=606.38.

Examples 9 to 11 were prepared according to the procedures described for the preparation of Examples 7 to 8:

Example 9

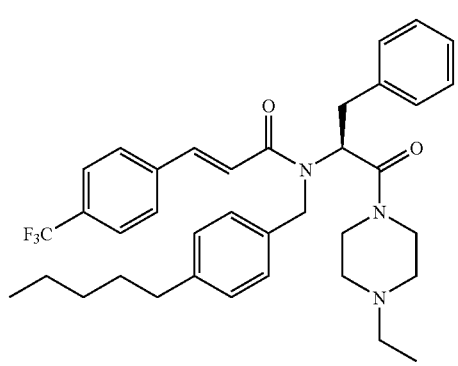

LC-MS:
$t_R$ = 1.01
[M + H]$^+$ = 620.55

Example 10

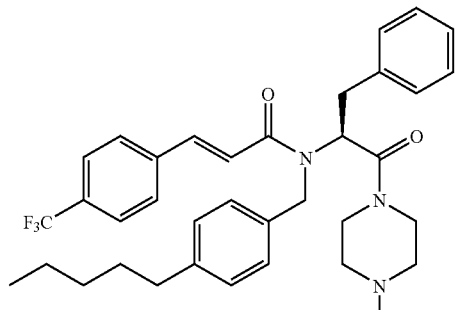

LC-MS:
$t_R = 0.99$
$[M + H]^+ = 636.48$

Example 11

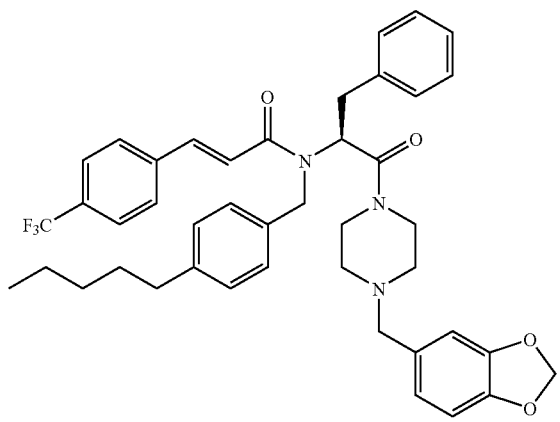

LC-MS:
$t_R = 1.06$
$[M + H]^+ = 726.43$

Example 12

Step 1

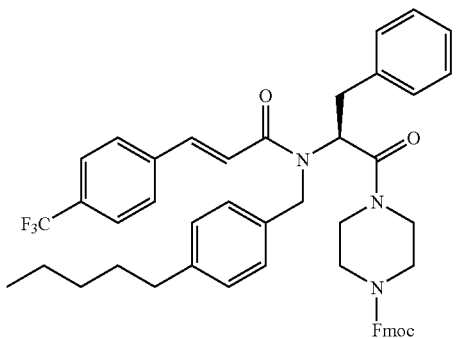

2-{(4-pentyl-benzyl)-[3-(4-trifluoromethyl-phenyl)-acryloyl]-amino}-(S)-3-phenyl-propionic acid (1.5 g, 2.86 mmol) and TBTU (1.1 g, 3.43 mmol) was dissolved in acetonitrile (30 mL) and DIPEA (1.5 mL, 8.6 mmol) and stirred at rt for 5 min, followed by the addition of Fmoc-piperazine hydrobromide (1.22 g, 3.15 mmol). The reaction mixture was stirred at rt for 16 h and concentrated under reduced pressure. The residue was dissolved in EtOAc (150 ml) and washed with brine (100 ml), dried over magnesium sulfate, filtered and concentrated under reduced pressure. The crude product was purified by column chromatography (silicagel, EtOAc/heptane=3/7) to give 1.75 g (75%) of 4-(2-{(4-pentyl-benzyl)-[3-(4-trifluoromethyl-phenyl)-acryloyl]-amino}-(S)-3-phenyl-propionyl)-piperazine-1-carboxylic acid 9H-fluoren-9-ylmethyl ester. LC-MS: $t_R$=1.25 min; $[M+H]^+$=814.5.

Step 2

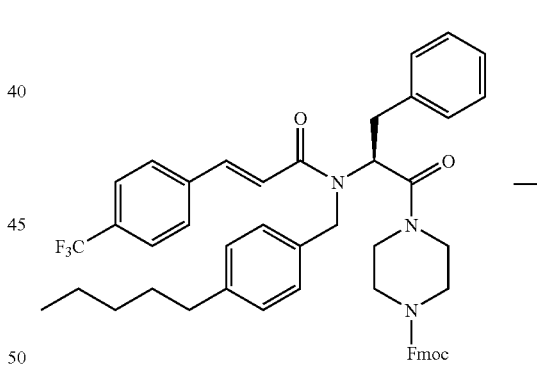

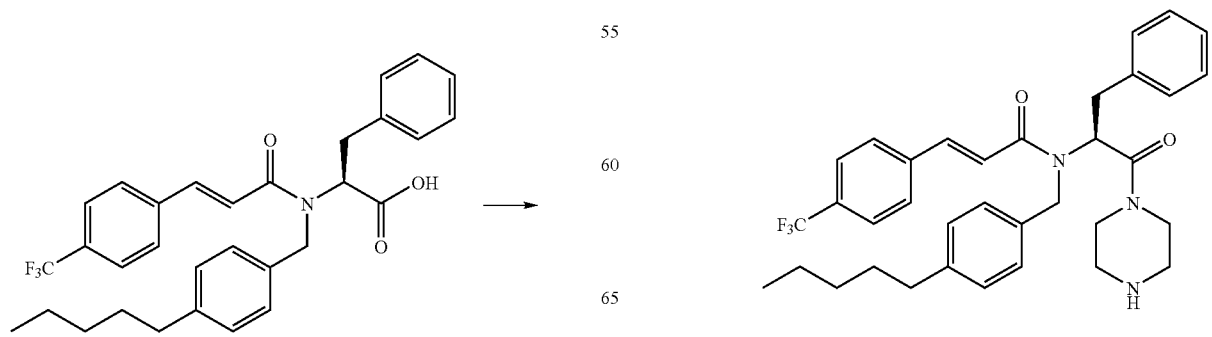

4-(2-{(4-pentyl-benzyl)-[3-(4-trifluoromethyl-phenyl)-acryloyl]-amino}-(S)-3-phenyl-propionyl)-piperazine-1-carboxylic acid 9H-fluoren-9-ylmethyl ester (1.75 g, 2.15 mmol) was dissolved in DMF (47.5 mL) and piperidine (2.5 mL) was added. Stirring was continued at rt for 30 min. EtOAc (150 mL) was added and the mixture was washed with water (2×150 mL). The organic layer was dried over magnesium sulfate, filtered and concentrated in vacuo. The residue was purified by column chromatography (silicagel, MeOH/DCM=1/99) to give 1.05 g (82.5%) of N—((S)-1-Benzyl-2-oxo-2-piperazin-1-yl-ethyl)-N-(4-pentyl-benzyl)-3-(4-trifluoromethyl-phenyl)-acrylamide. LC-MS: $t_R$=0.97 min; [M+H]$^+$=592.19.

Step 3

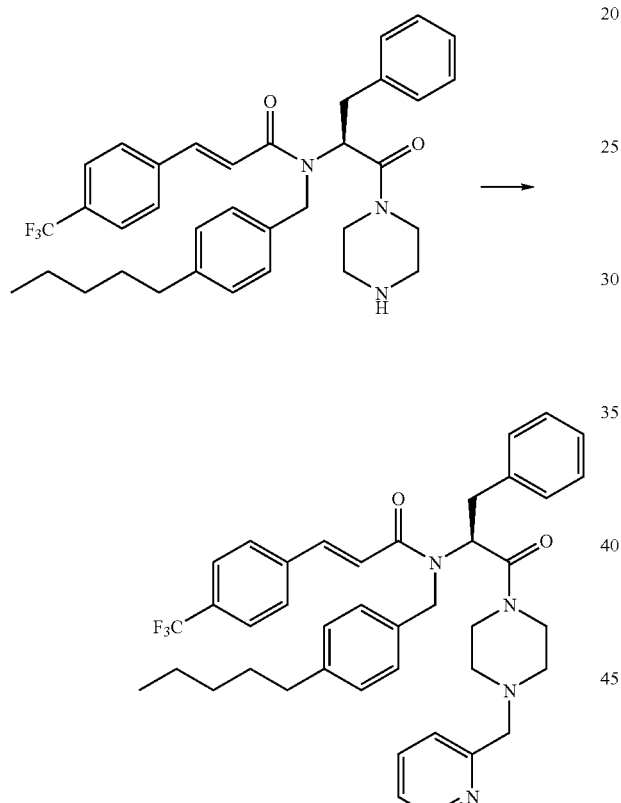

N—((S)-1-Benzyl-2-oxo-2-piperazin-1-yl-ethyl)-N-(4-pentyl-benzyl)-3-(4-trifluoromethyl-phenyl)-acrylamide (50 mg, 0.084 mmol) was dissolved in acetonitrile (1 mL) and pyridine-2-carbaldehyde (10 mg, 0.092 mmol) and sodium triacetoxyborohydride (26.7 mg, 0.126 mmol) was added. The mixture was stirred at rt for 16 h, filtered and directly purified by prep. HPLC to give 29 mg of N—[(S)-1-Benzyl-2-oxo-2-(4-pyridin-2-ylmethyl-piperazin-1-yl)-ethyl]-N-(4-pentyl-benzyl)-3-(4-trifluoromethyl-phenyl)-acrylamide. LC-MS: $t_R$=1.02 min; [M+H]$^+$=683.58.

Examples 13 to 28 were prepared according to the procedures described for the preparation of Example 12:

Example 13

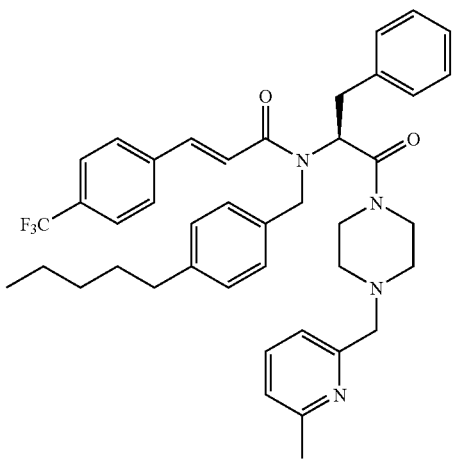

LC-MS:
$t_R$ = 1.04
[M + H]$^+$ = 697.54

Example 14

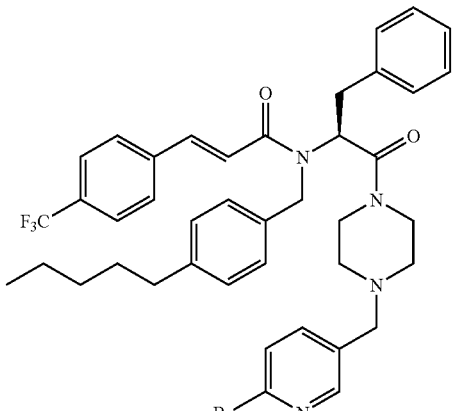

LC-MS:
$t_R$ = 1.05
[M + H]$^+$ = 761.39

Example 15

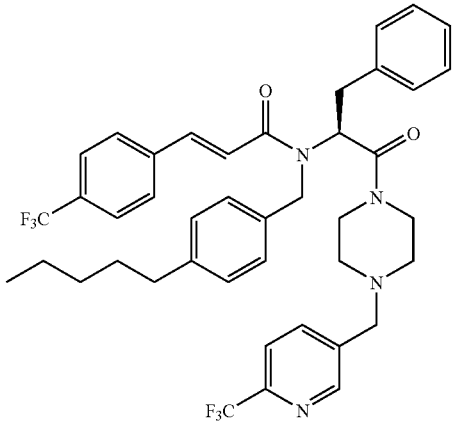

LC-MS:
$t_R$ = 1.07
[M + H]$^+$ = 751.53

Example 16
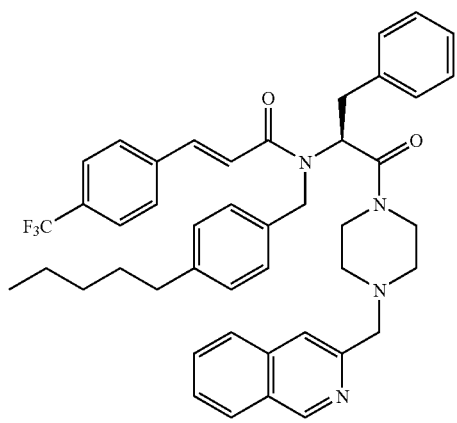
LC-MS:
t$_R$ = 1.04
[M + H]$^+$ = 733.47
Example 17
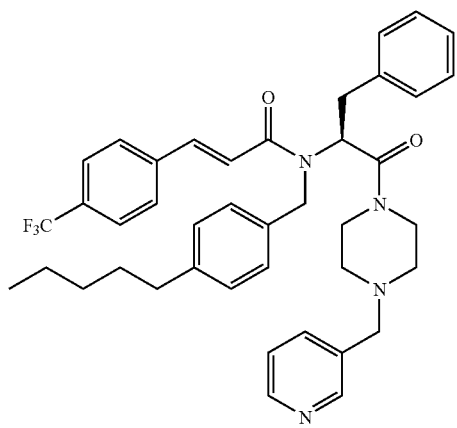
LC-MS:
t$_R$ = 1.04
[M + H]$^+$ = 713.53
Example 18
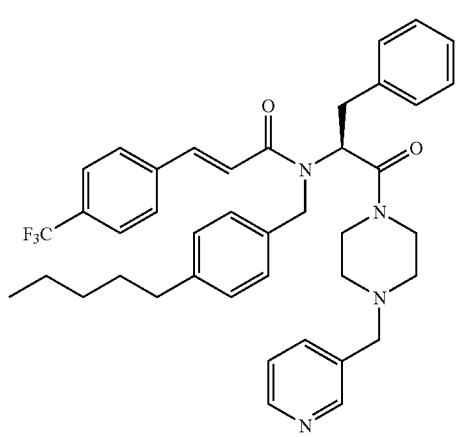
LC-MS:
t$_R$ = 1.04
[M + H]$^+$ = 717.46
Example 19
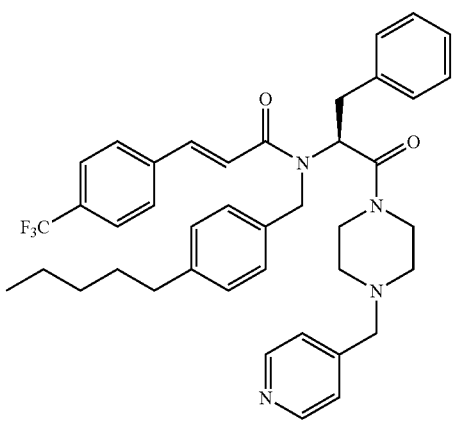
LC-MS:
t$_R$ = 1.01
[M + H]$^+$ = 683.41
Example 20
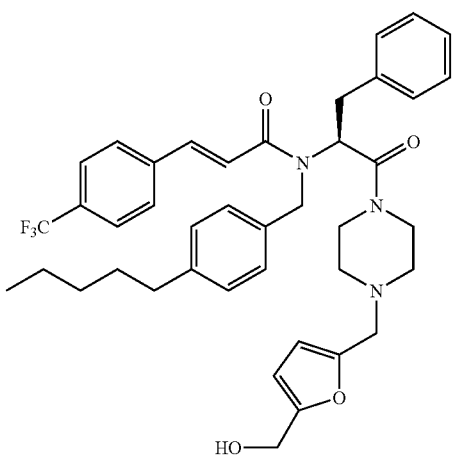
LC-MS:
t$_R$ = 1.00
[M + H]$^+$ = 702.69
Example 21
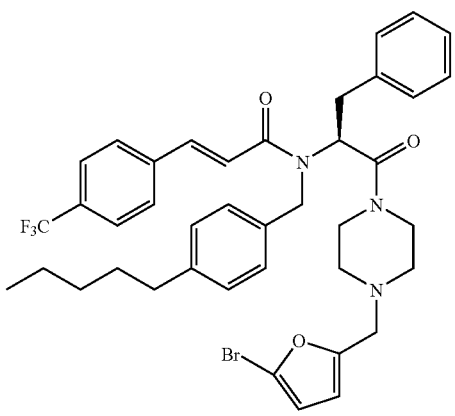
LC-MS:
t$_R$ = 1.06
[M + H]$^+$ = 750.37

| 45 | 46 |
|---|---|
| Example 22 | Example 25 |
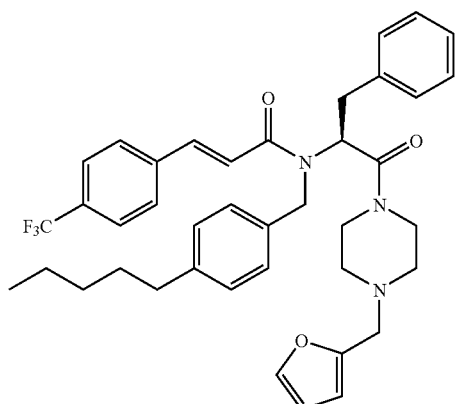
LC-MS:
$t_R = 1.04$
$[M + H]^+ = 672.47$
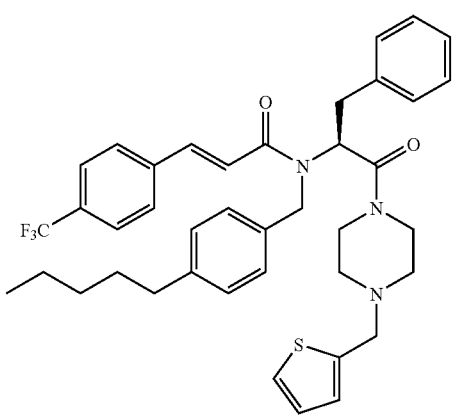
LC-MS:
$t_R = 1.05$
$[M + H]^+ = 688.49$
Example 23
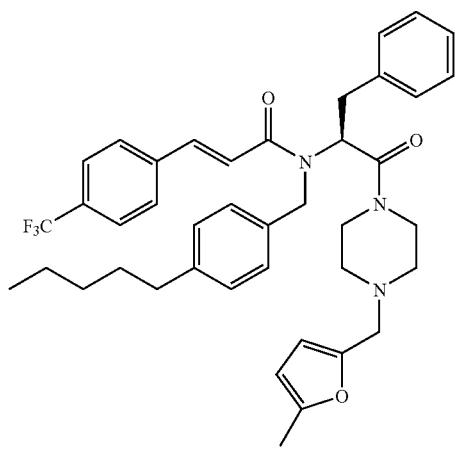
LC-MS:
$t_R = 1.05$
$[M + H]^+ = 686.58$
Example 26
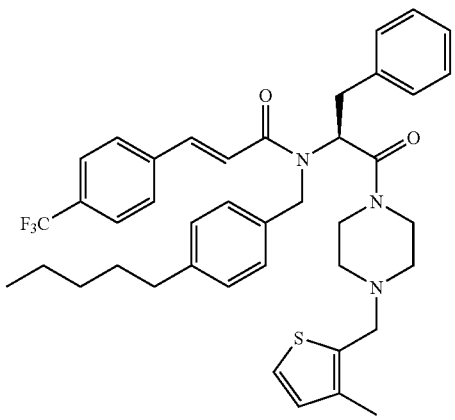
LC-MS:
$t_R = 1.06$
$[M + H]^+ = 702.50$
Example 24
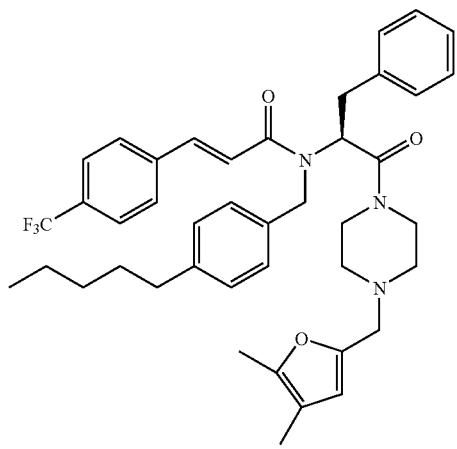
LC-MS:
$t_R = 1.07$
$[M + H]^+ = 700.58$
Example 27
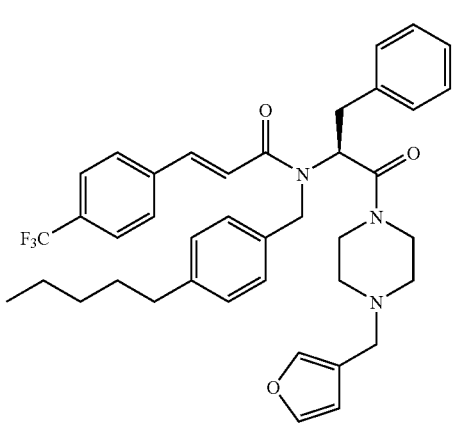
LC-MS:
$t_R = 1.03$
$[M + H]^+ = 672.51$

Example 28

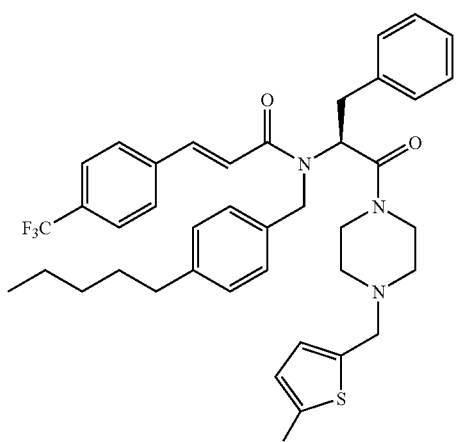

LC-MS:
$t_R = 1.07$
$[M + H]^+ = 722.37$

Example 29

Step 1

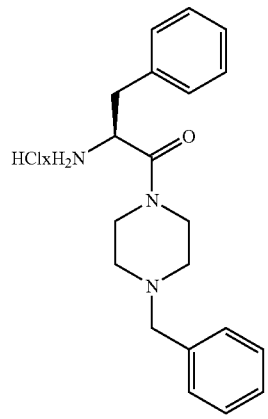

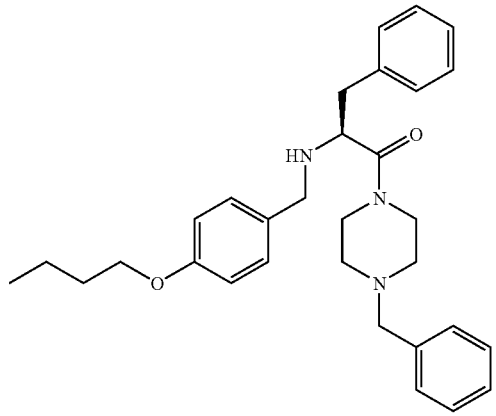

2-Amino-1-(4-benzyl-piperazin-1-yl)-(S)-3-phenyl-propan-1-one hydrochloride (500 mg, 1.26 mmol) were dissolved in MeOH (5 mL), DIPEA (359 mg, 2.77 mmol) and 4-n-butoxybenzaldehyde (226 mg, 1.26 mmol) was added and the mixture was heated to reflux for 2 h, cooled again to rt followed by slow addition of sodium borohydride (48 mg, 1.26 mmol) in portions. Stirring was continued for 15 min. Water (1 mL) was added and the solvents were removed under reduced pressure. The residue was taken up in diethylether (5 mL), washed with 10% aq. citric acid (5 mL) and water (5 mL), dried over magnesium sulfate, filtered and concentrated in vacuo to give 411 mg (67%) of 1-(4-benzyl-piperazin-1-yl)-2-(4-butoxy-benzylamino)-(S)-3-phenyl-propan-1-one. LC-MS: $t_R$=0.74 min; [M+H]$^+$=486.43.

Step 2

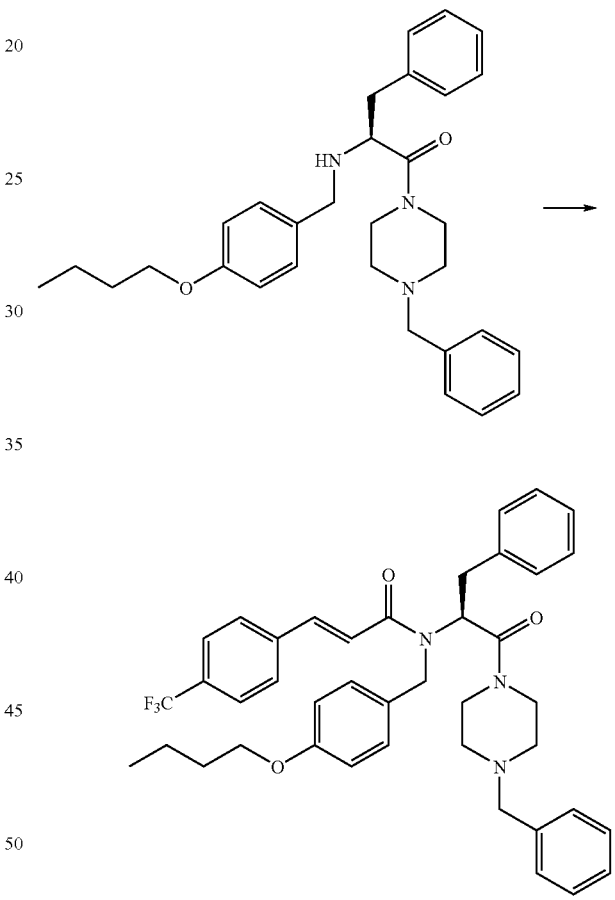

In an inert atmosphere, trans-4-(trifluoromethyl)cinnamic acid (28 mg, 0.13 mmol) was dissolved in DCM (0.5 mL) followed by the addition of 1-chloro-N,N,2-trimethylpropenylamine (19.4 mg, 0.145 mmol). The mixture was stirred at rt for 30 min followed by the addition of DIPEA (34 mg, 0.26 mmol) and 1-(4-benzyl-piperazin-1-yl)-2-(4-butoxy-benzylamino)-(S)-3-phenyl-propan-1-one (63 mg, 0.13 mmol). Stirring was continued for 30 min. The mixture was concentrated in vacuo and the residue was directly purified by prep. HPLC to give 51 mg (57%) of N—[(S)-1-benzyl-2-(4-benzyl-piperazin-1-yl)-2-oxo-ethyl]-N-(4-butoxy-benzyl)-3-(4-trifluoromethyl-phenyl)-acrylamide. LC-MS: $t_R$=1.02 min; [M+H]$^+$=684.49.

The following Examples 30 to 46 were prepared by applying the same 2 step sequence using different aldehydes and either trans-4-(trifluoromethyl)cinnamic acid or trans-4-(methoxy)cinnamic acid.
Example 30
Example 31
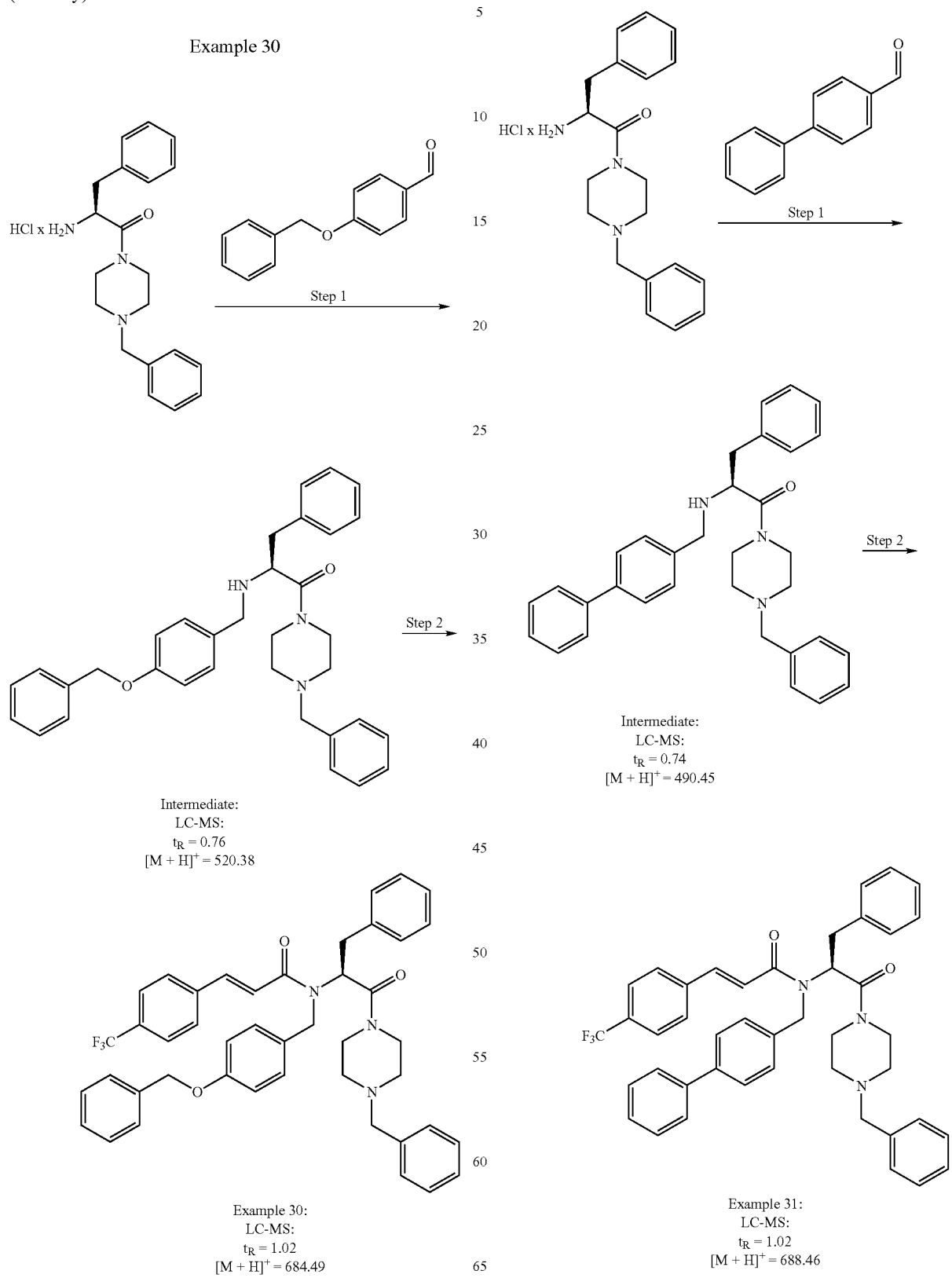
Intermediate:
LC-MS:
$t_R = 0.76$
$[M + H]^+ = 520.38$
Intermediate:
LC-MS:
$t_R = 0.74$
$[M + H]^+ = 490.45$
Example 30:
LC-MS:
$t_R = 1.02$
$[M + H]^+ = 684.49$
Example 31:
LC-MS:
$t_R = 1.02$
$[M + H]^+ = 688.46$

51
Example 32
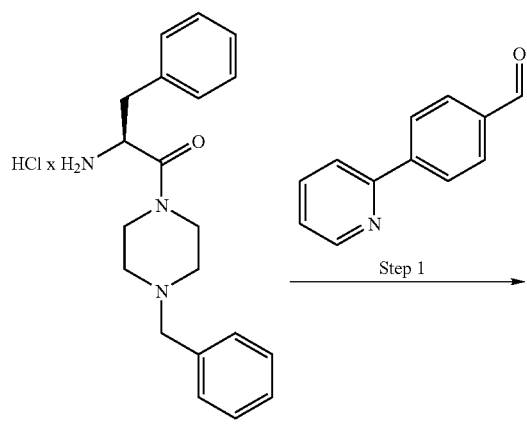
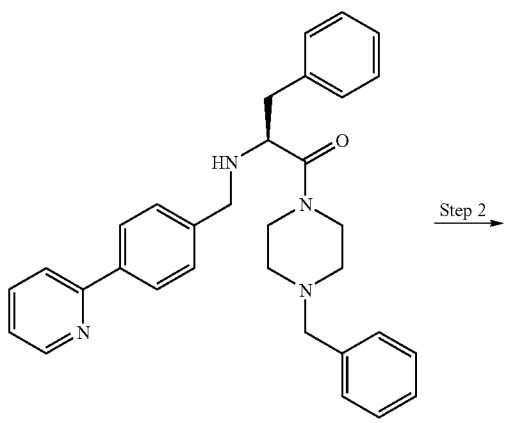
Intermediate:
LC-MS:
$t_R = 0.62$
$[M + H]^+ = 491.50$
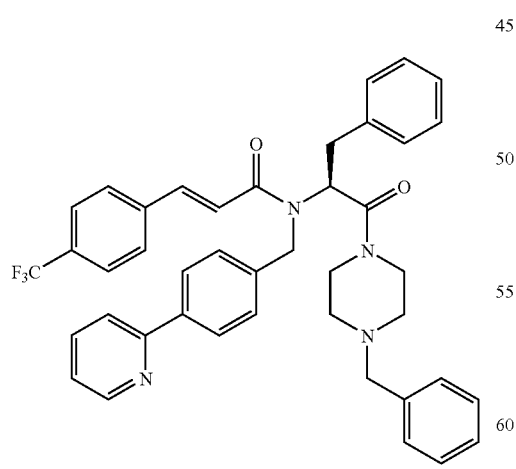
Example 32:
LC-MS:
$t_R = 0.90$
$[M + H]^+ = 689.48$
52
Example 33
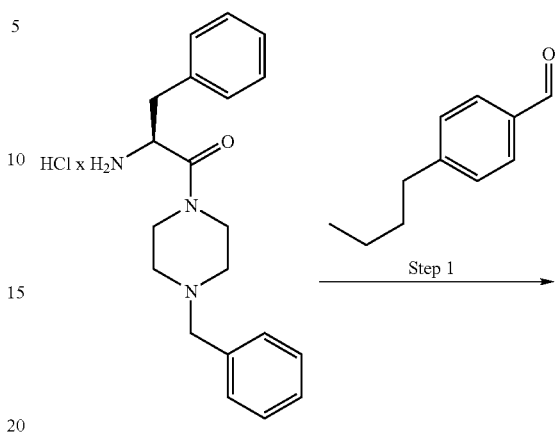
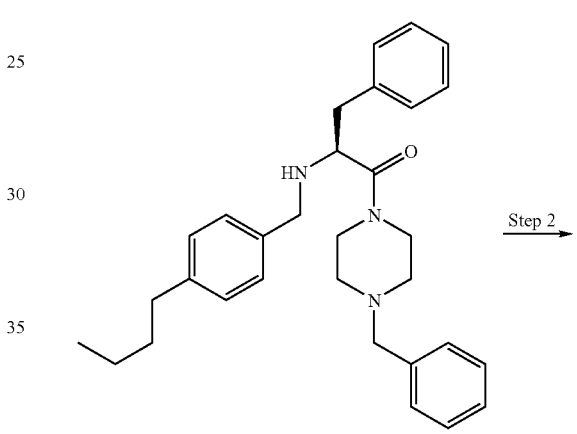
Intermediate:
LC-MS:
$t_R = 0.76$
$[M + H]^+ = 470.38$
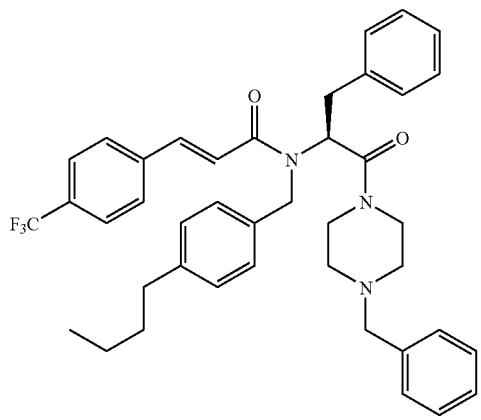
Example 33:
LC-MS:
$t_R = 1.04$
$[M + H]^+ = 668.52$

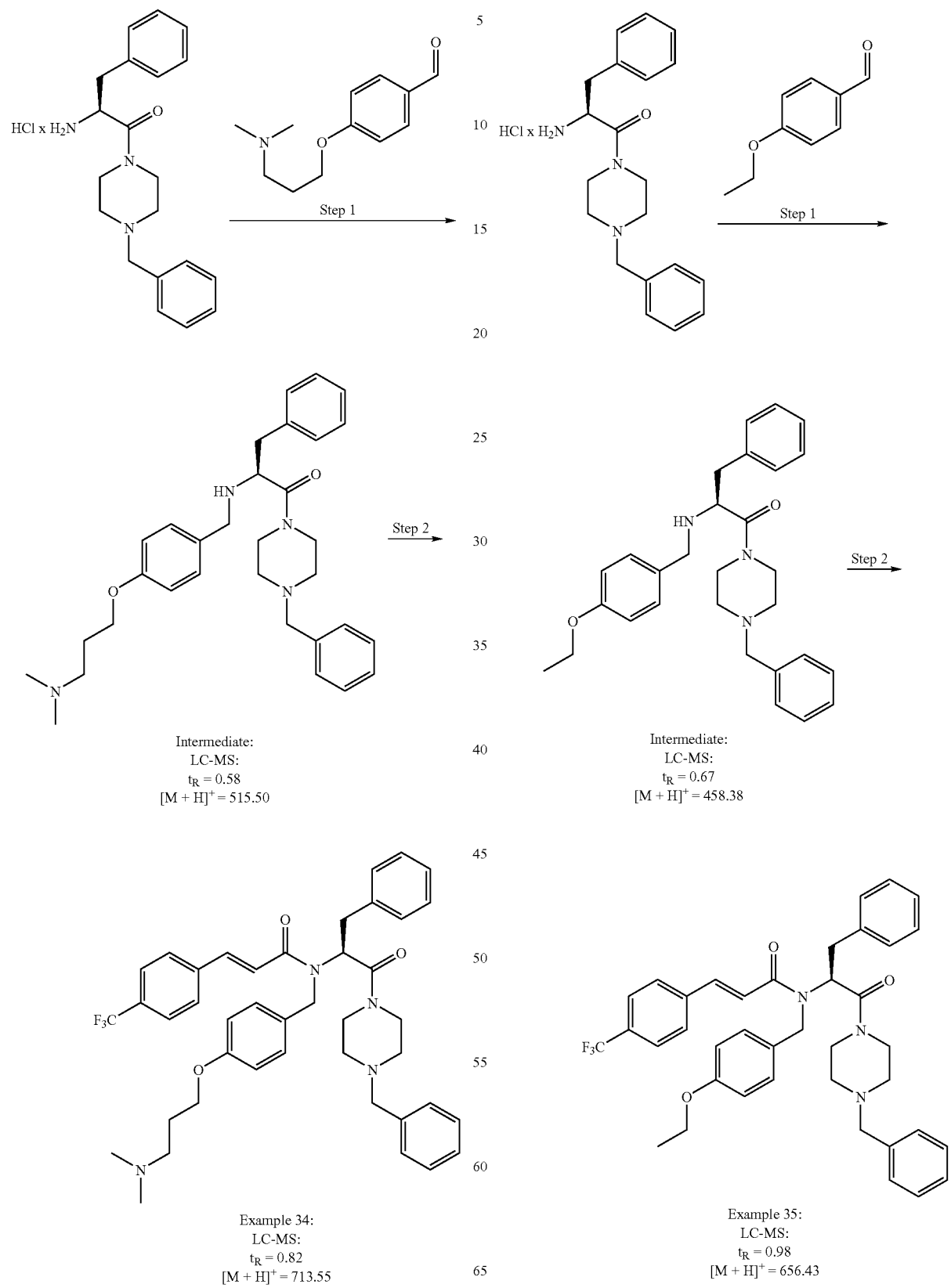

Example 36
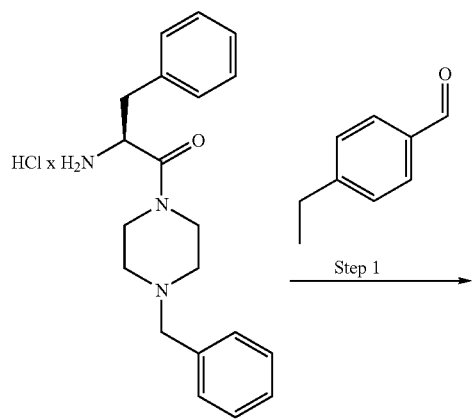
Intermediate:
LC-MS:
$t_R = 0.69$
$[M + H]^+ = 442.40$
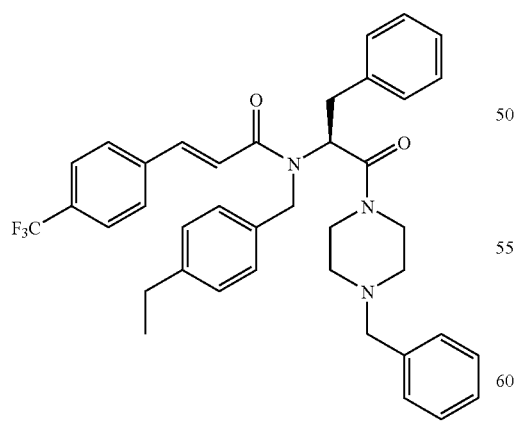
Example 36:
LC-MS:
$t_R = 1.00$
$[M + H]^+ = 640.51$
Example 37
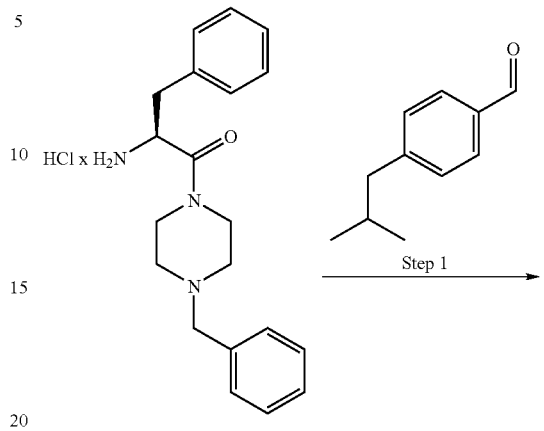
Intermediate:
LC-MS:
$t_R = 0.75$
$[M + H]^+ = 470.43$
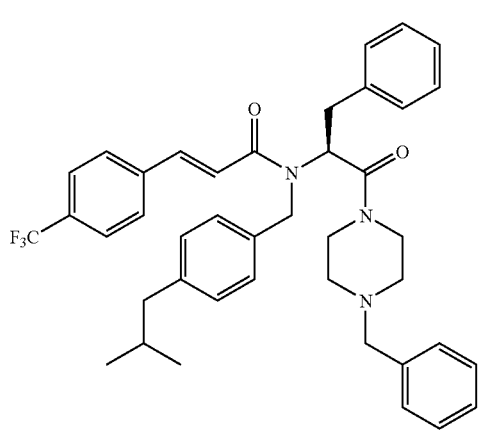
Example 37:
LC-MS:
$t_R = 1.04$
$[M + H]^+ = 668.52$ Examples 38 to 43
Example 38:
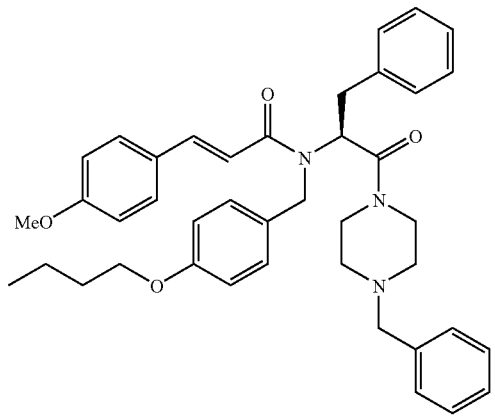
LC-MS:
$t_R = 0.99$
$[M + H]^+ = 646.47$
Example 39:
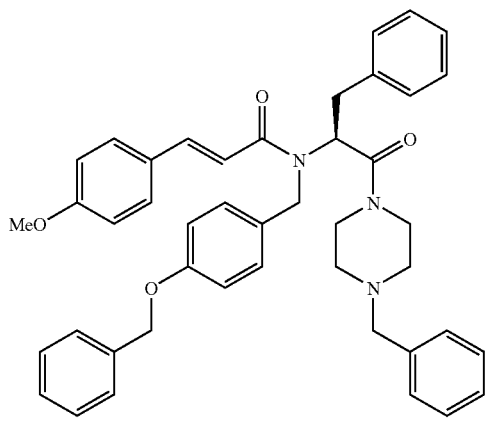
LC-MS:
$t_R = 0.99$
$[M + H]^+ = 680.50$
Example 40:
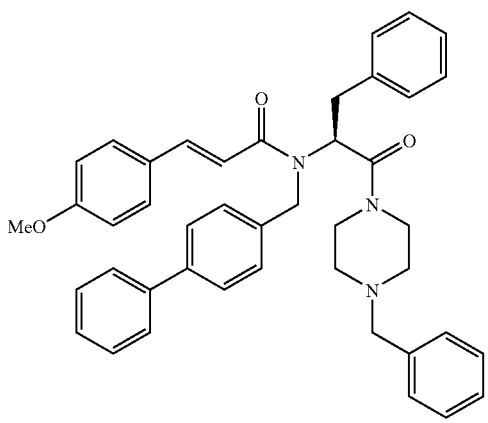
LC-MS:
$t_R = 0.98$
$[M + H]^+ = 650.40$
Example 41:
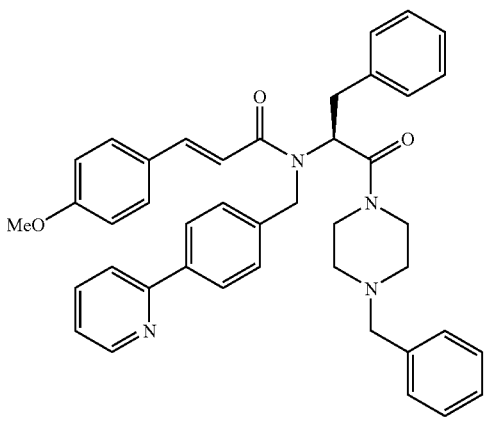
LC-MS:
$t_R = 0.84$
$[M + H]^+ = 651.52$
Example 42:
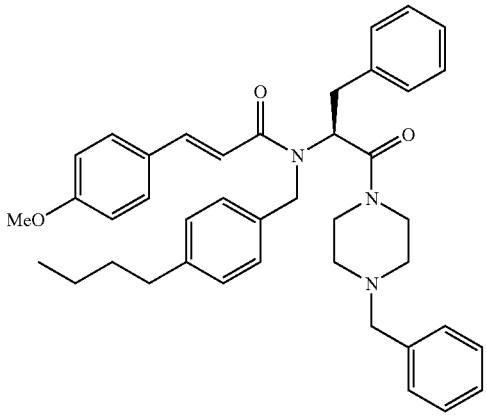
LC-MS:
$t_R = 1.01$
$[M + H]^+ = 630.50$
Example 43:
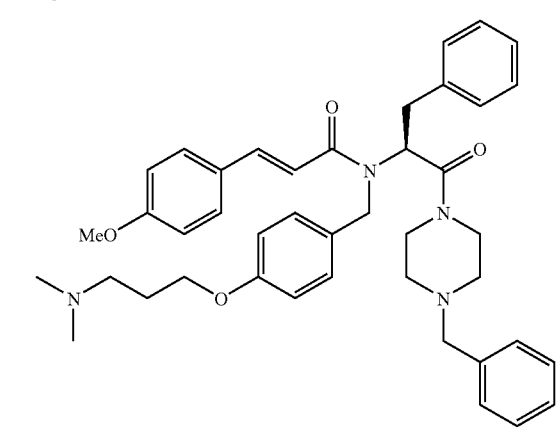
LC-MS:
$t_R = 0.78$
$[M + H]^+ = 675.50$

Examples 44 to 46

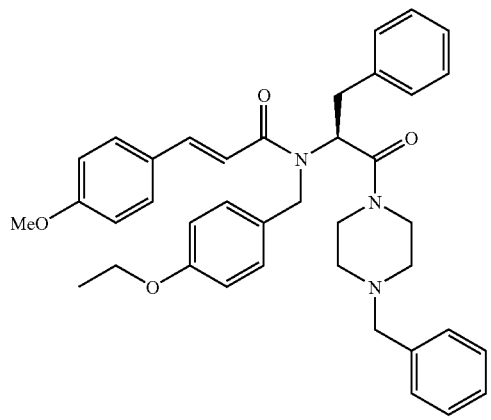

Example 44:
LC-MS:
$t_R = 0.95$
$[M + H]^+ = 618.38$

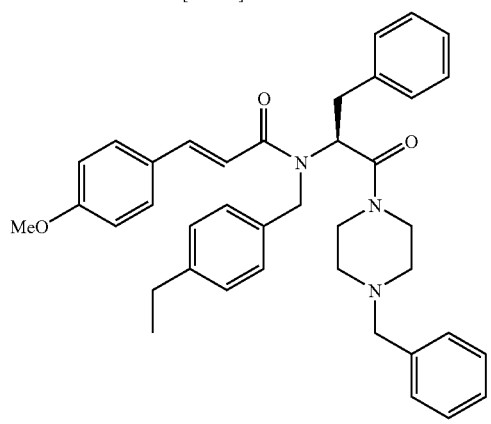

Example 45:
LC-MS:
$t_R = 0.97$
$[M + H]^+ = 602.37$

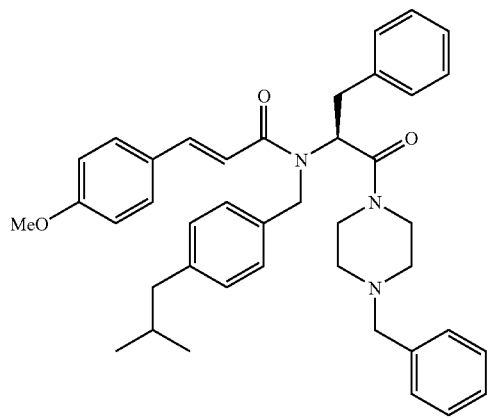

Example 46:
LC-MS:
$t_R = 1.01$
$[M + H]^+ = 630.51$

Example 47

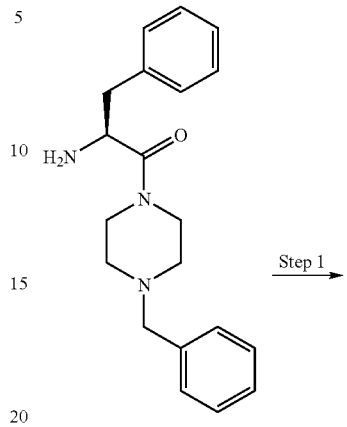

Step 1 →

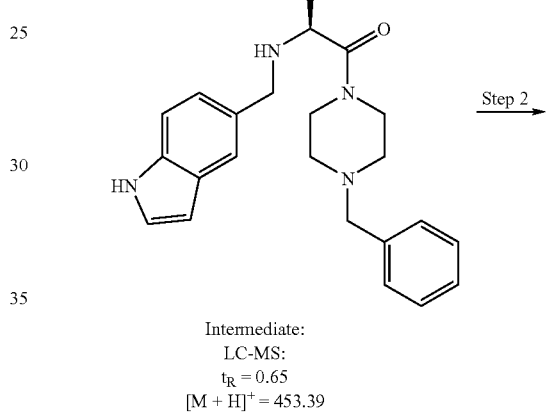

Intermediate:
LC-MS:
$t_R = 0.65$
$[M + H]^+ = 453.39$

Step 2 →

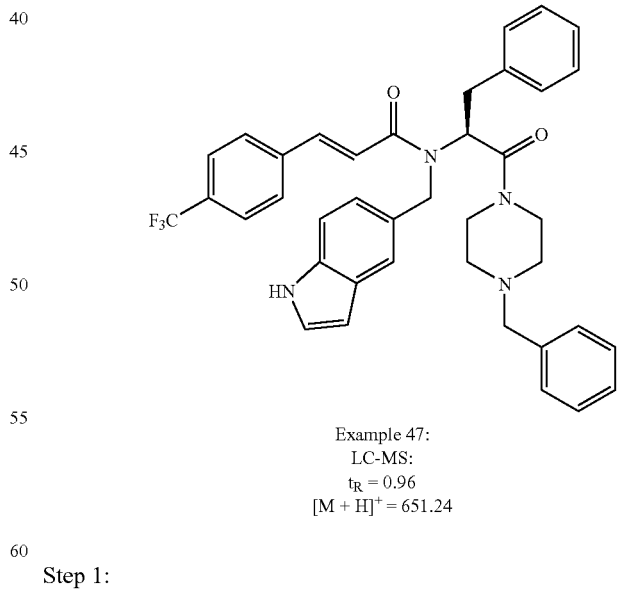

Example 47:
LC-MS:
$t_R = 0.96$
$[M + H]^+ = 651.24$

Step 1:

In an inert atmosphere, indole-5-carboxaldehyde (108 mg, 0.75 mmol) and 2-amino-1-(4-benzyl-piperazin-1-yl)-(S)-3-phenyl-propan-1-one (162 mg, 0.50 mmol) were dissolved in dry MeOH (4.0 mL) and refluxed for 4 h. The reaction mixture was cooled to rt followed by slow addition of sodium borohydride (28 mg, 0.75 mmol). Stirring was continued for 1 h. Water (1 mL) was added to the reaction mixture followed by evaporation of the solvent under reduced pressure. The residue was dissolved in EtOAc (10 mL) and washed with sat. sodium hydrogencarbonate solution (10 mL) and brine (10 mL). The organic layer was dried over magnesium sulfate, filtered and concentrated in vacuo to give 200 mg (80%) of 1-(4-benzyl-piperazin-1-yl)-2-[(1H-indol-5-ylmethyl)-amino]-(S)-3-phenyl-propan-1-one. LC-MS: $t_R$=0.65 min; [M+H]$^+$=453.39.

Step 2:

In an inert atmosphere, trans-4-(trifluoromethyl)cinnamic acid (34 mg, 0.156 mmol) was dissolved in DCM (3 mL) and 1-chloro-N,N,2-trimethylpropenylamine (24 mg, 0.182 mmol) was added at rt. The reaction mixture was stirred for 30 min followed by the addition of 1-(4-benzyl-piperazin-1-yl)-2-[(1H-indol-5-ylmethyl)-amino]-(S)-3-phenyl-propan-1-one (59 mg, 0.13 mmol). Stirring was continued at rt for 3 h. The solvents were evaporated under reduced pressure and the residue was directly purified by prep. HPLC to give 33 mg (39%) of N—[(S)-1-benzyl-2-(4-benzyl-piperazin-1-yl)-2-oxo-ethyl]-N-(1H-indol-5-ylmethyl)-3-(4-trifluoromethyl-phenyl)-acrylamide. LC-MS: $t_R$=0.96 min; [M+H]$^+$=651.24.

Example 48

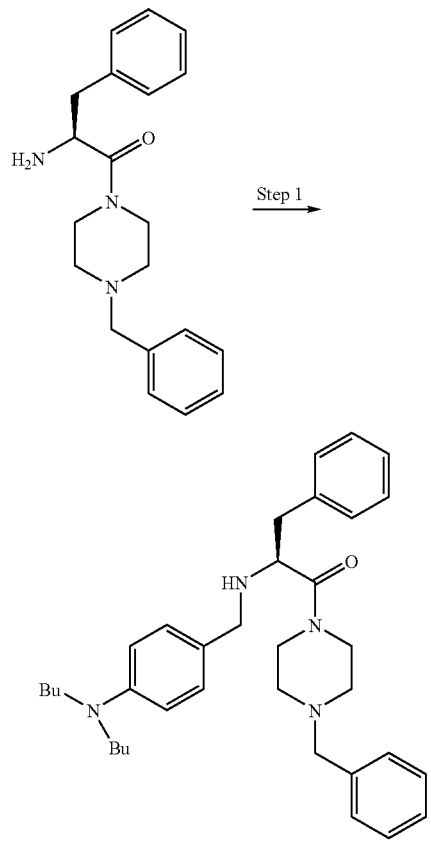

Intermediate:
LC-MS:
$t_R$ = 0.75
[M + H]$^+$ = 541.49

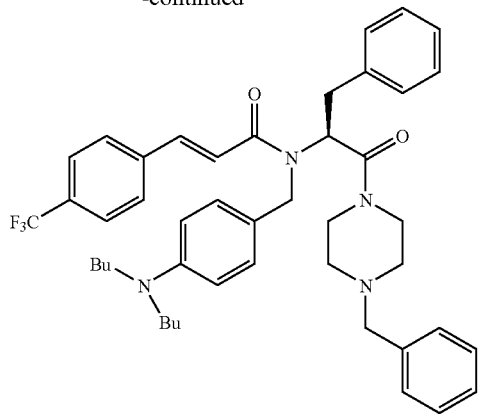

Example 48:
LC-MS:
$t_R$ = 0.89
[M + H]$^+$ = 739.71

The compound of Example 48 was prepared according to the procedures described for the preparation of Example 47, replacing indole-5-carboxaldehyde in step 1 by 4-n-dibutylaminobenzaldehyde.

Example 49

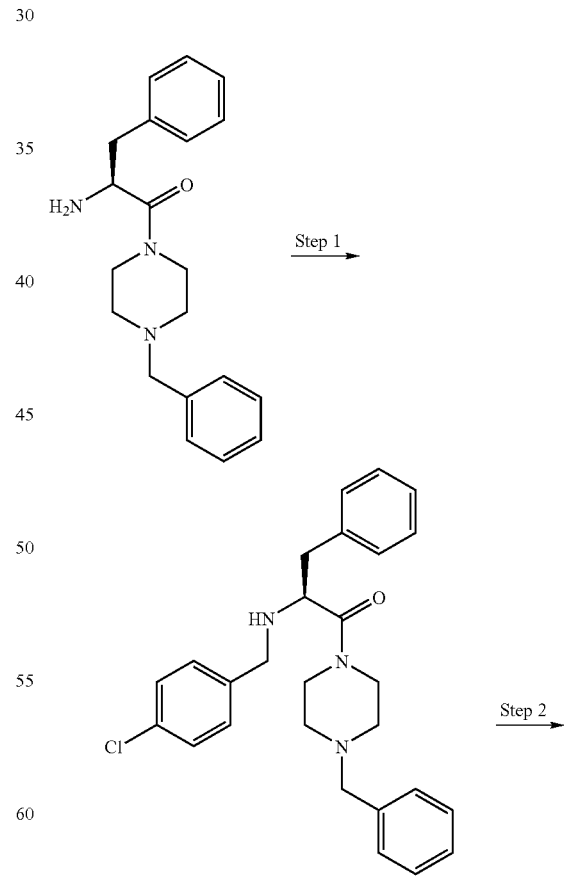

Intermediate 1:
LC-MS:
$t_R$ = 0.69
[M + H]$^+$ = 448.17

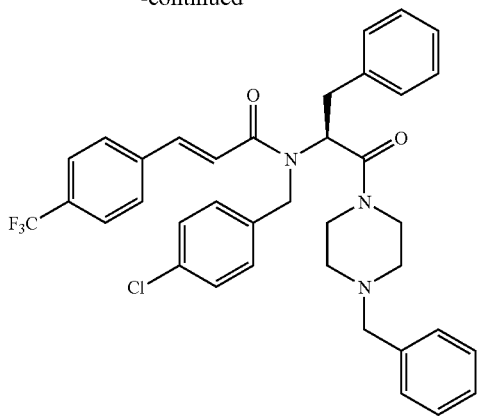

Intermediate 2:
LC-MS:
$t_R = 0.98$
$[M + H]^+ = 646.67$

↓ Step 3

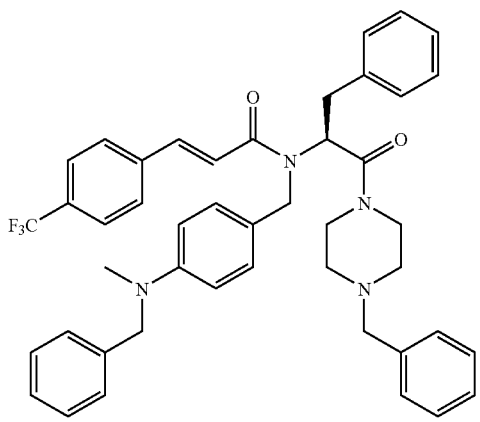

Example 49:
LC-MS:
$t_R = 0.97$
$[M + H]^+ = 772.6$

Step 1:

According to the procedures described above for the reductive amination step, 2-amino-1-(4-benzyl-piperazin-1-yl)-(S)-3-phenyl-propan-1-one (1.4 g, 3.53 mmol) was converted into 1-(4-benzyl-piperazin-1-yl)-2-(4-chloro-benzylamino)-(S)-3-phenyl-propan-1-one (1.56 g, 99%). LC-MS: $t_R$=0.69 min; [M+H]$^+$=448.17.

Step 2:

According to the procedures described above for the acylation with 1-chloro-N,N,2-trimethylpropenylamine as the activation reagent, 1-(4-benzyl-piperazin-1-yl)-2-(4-chloro-benzylamino)-(S)-3-phenyl-propan-1-one (1.43 g, 3.20 mmol) was converted into N—[(S)-1-benzyl-2-(4-benzyl-piperazin-1-yl)-2-oxo-ethyl]-N-(4-chloro-benzyl)-3-(4-trifluoromethyl-phenyl)-acrylamide (1.63 g, 79%). LC-MS: $t_R$=0.98 min; [M+H]$^+$=646.67.

Step 3:

1-(4-Benzyl-piperazin-1-yl)-2-(4-chloro-benzylamino)-(S)-3-phenyl-propan-1-one (830 mg, 1.21 mmol), 1-phenyl-piperazine (208 mg, 1.21 mmol) and sodium tert.-butoxide (301 mg, 3.04 mmol) were dissolved in dioxane (20 mL) and degassed for 5 min with N$_2$-gas. Stirring at rt was continued for 30 min. The reaction mixture was heated to 80° C. and SK-CC02-A (37 mg, 0.061 mmol) dissolved in dioxane (5 mL) was added via syringe. The mixture was heated to 110° C. for 2 h, cooled again to rt followed by the addition of water (100 mL). The product was extracted by EtOAc (2×100 mL). The combined organic layers were dried over magnesium sulfate, filtered and concentrated in vacuo. The crude material was purified by column chromatography (silicagel, heptane/EtOAc=1/1) to give 246 mg (26%) of N-[(S)-1-benzyl-2-(4-benzyl-piperazin-1-yl)-2-oxo-ethyl]-N-(4-chloro-benzyl)-3-(4-trifluoromethyl-phenyl)-acrylamide. LC-MS: $t_R$=0.98 min; [M+H]$^+$=772.71.

Examples 50 to 56 were prepared according to the procedures described for the preparation of Example 49:

Example 50

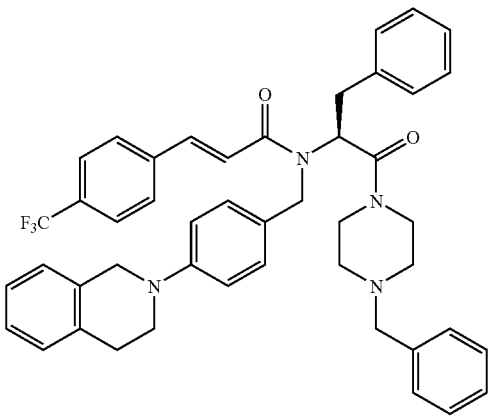

LC-MS:
$t_R = 0.99$
$[M + H]^+ = 731.85$

Example 51

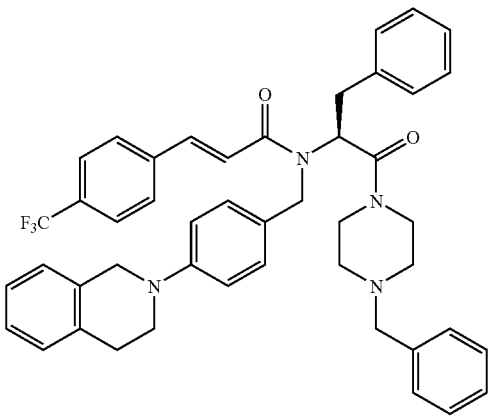

LC-MS:
$t_R = 0.99$
$[M + H]^+ = 743.59$

Example 52

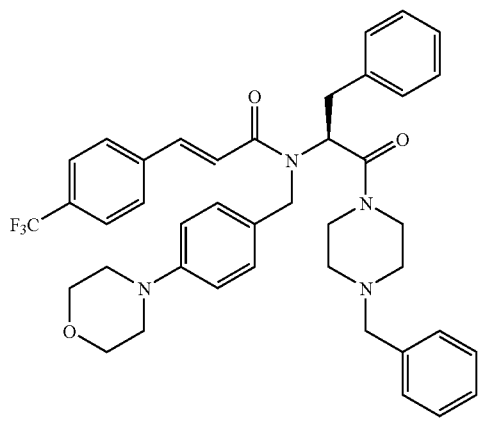

LC-MS:
$t_R = 0.92$
$[M + H]^+ = 697.56$

Example 53

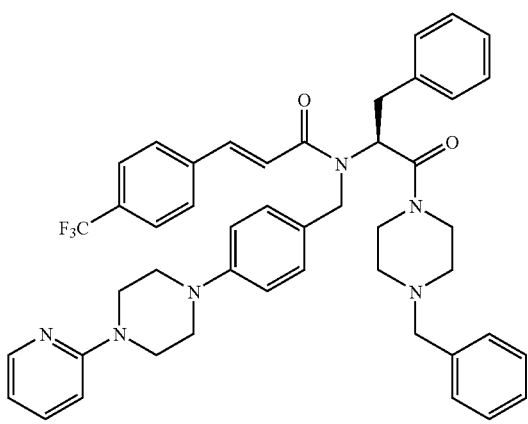

LC-MS:
$t_R = 0.81$
$[M + H]^+ = 773.59$

Example 54

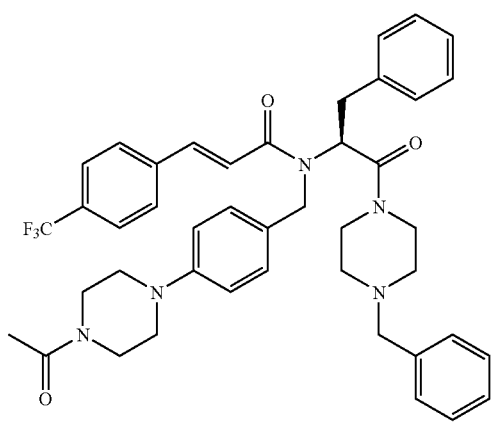

LC-MS:
$t_R = 0.92$
$[M + H]^+ = 738.34$

Example 55

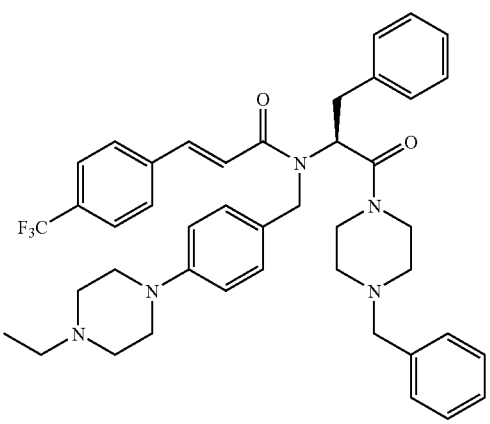

LC-MS:
$t_R = 0.82$
$[M + H]^+ = 724.39$

Example 56

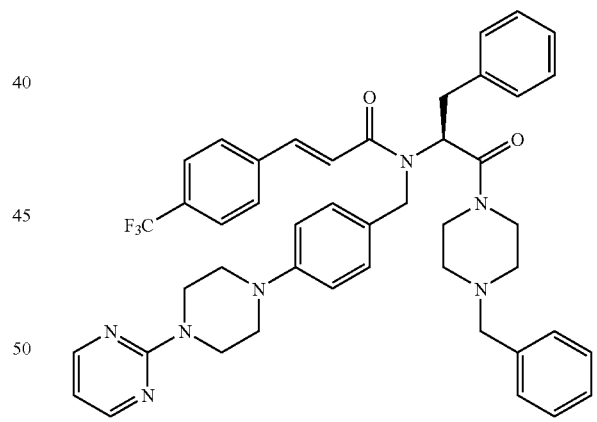

LC-MS:
$t_R = 0.97$
$[M + H]^+ = 774.38$

Examples 57 to 64 were prepared according to the procedures described above for the preparation of Example 1 by replacing Boc-L-phenylalanine by the respective Boc-L-aminoacid, except for Example 61 where the racemic Boc-protected aminoacid was used:

Example 57
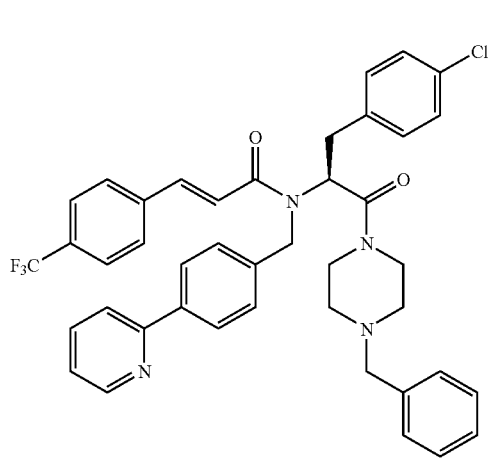
LC-MS:
$t_R = 0.90$
$[M + H]^+ = 723.43$
Example 58
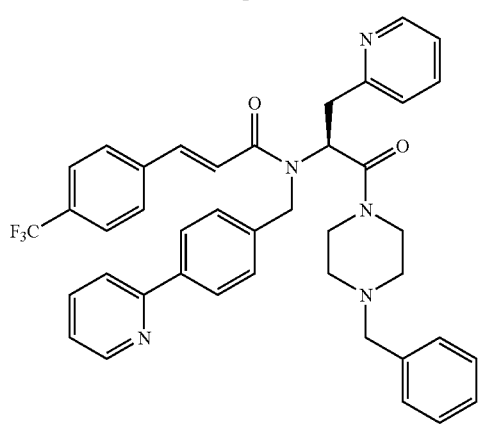
LC-MS:
$t_R = 0.77$
$[M + H]^+ = 690.47$
Example 59
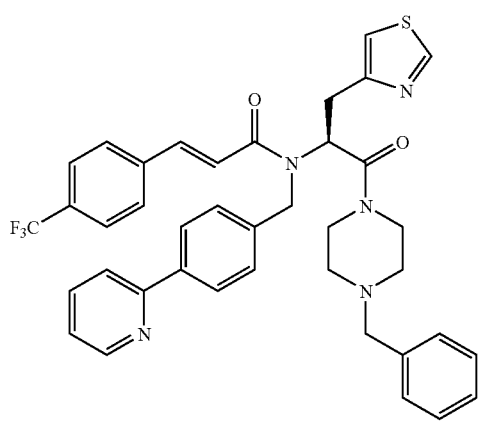
LC-MS:
$t_R = 0.83$
$[M + H]^+ = 696.41$
Example 60
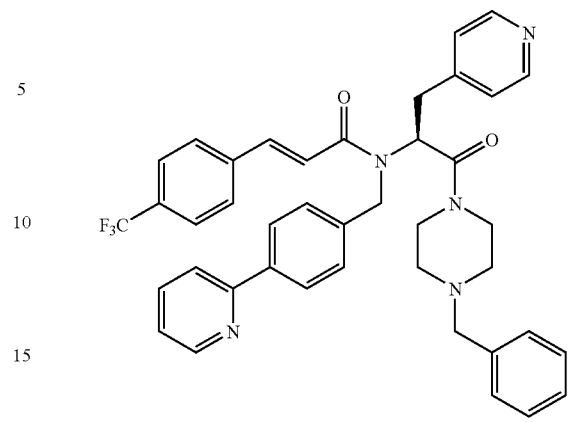
LC-MS:
$t_R = 0.75$
$[M + H]^+ = 690.3$
Example 61
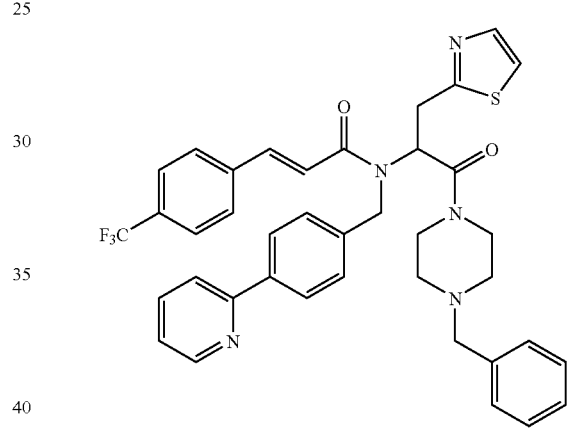
LC-MS:
$t_R = 0.84$
$[M + H]^+ = 696.30$
Example 62
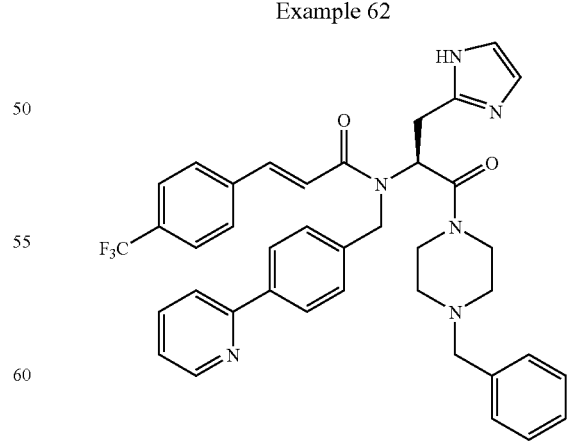
LC-MS:
$t_R = 0.73$
$[M + H]^+ = 679.7$

69
Example 63
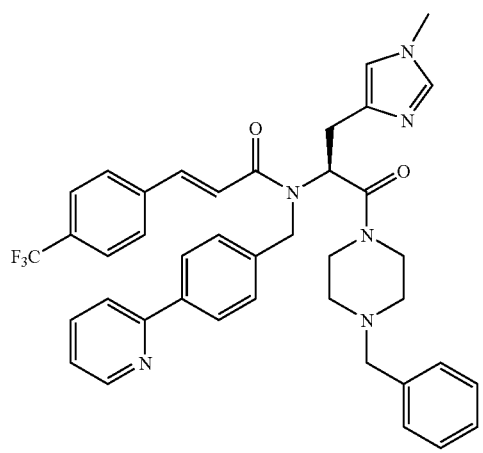
LC-MS:
$t_R = 0.74$
$[M + H]^+ = 693.70$
70
Example 64
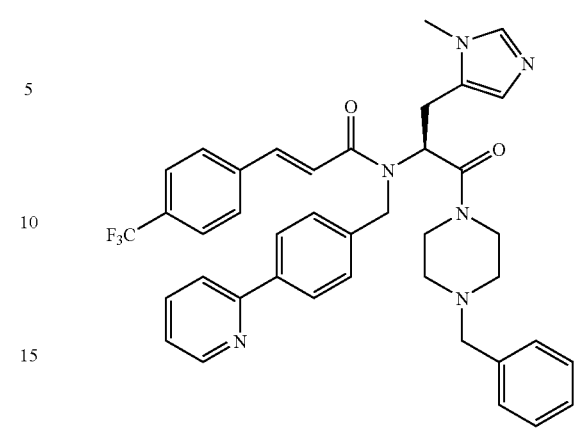
LC-MS:
$t_R = 0.74$
$[M + H]^+ = 693.70$
Examples 65 to 73 were prepared according to procedures described above:
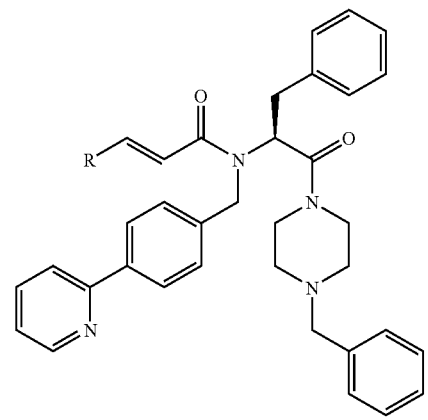
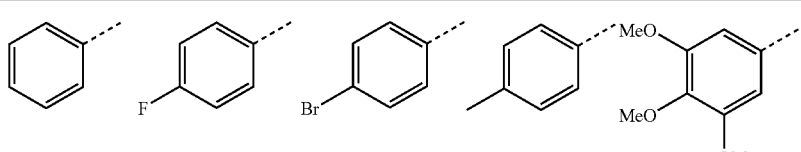
| LC-MS | | | | | |
|---|---|---|---|---|---|
| Ex-No.: | 65 | 66 | 67 | 68 | 69 |
| $t_R =$ | 0.81 | 0.82 | 0.84 | 0.83 | 0.81 |
| $[M + H]+ =$ | 621.57 | 639.59 | 701.44 | 635.57 | 711.55 |
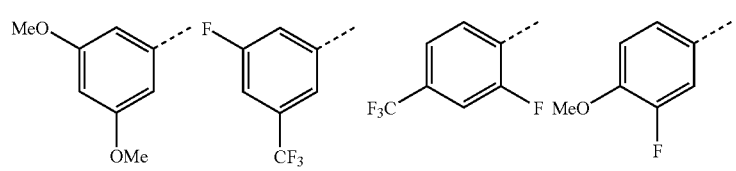
| LC-MS | | | | |
|---|---|---|---|---|
| Ex-No.: | 70 | 71 | 72 | 73 |
| $t_R =$ | 0.81 | 0.91 | 0.90 | 0.85 |
| $[M + H]+ =$ | 681.59 | 707.44 | 707.31 | 669.37 |

Example 74

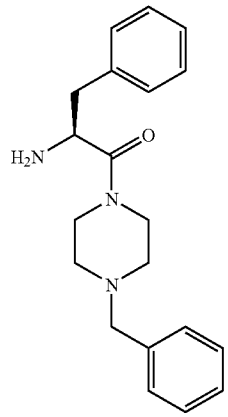

Step 1 →

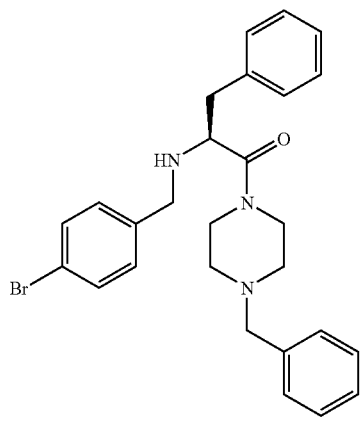

Intermediate 1:
LC-MS:
$t_R = 0.67$
$[M + H]^+ = 494.56$

Step 2 →

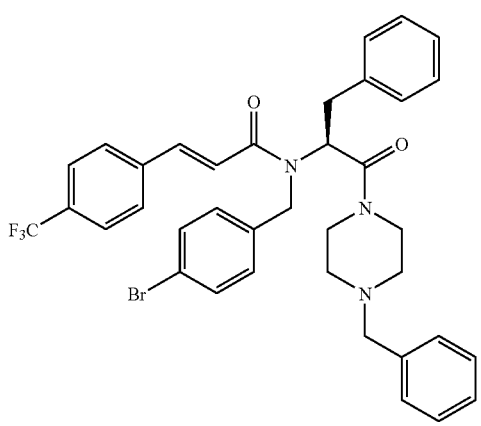

Intermediate 2:
LC-MS:
$t_R = 0.99$
$[M + H]^+ = 692.66$

Step 3 ↓

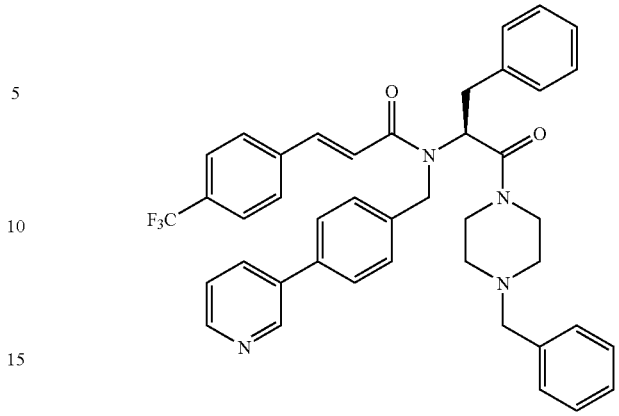

Example 74:
LC-MS:
$t_R = 0.85$
$[M + H]^+ = 689.68$

Step 1:

Was performed according to the description of Example 49, Step 1: 1-(4-Benzyl-piperazin-1-yl)-2-(4-bromo-benzylamino)-(S)-3-phenyl-propan-1-one (1.25 g, quant. yield, LC-MS: $t_R$=0.67 min; [M+H]$^+$=494.56) was obtained from 2-amino-1-(4-benzyl-piperazin-1-yl)-(S)-3-phenyl-propan-1-one (1.0 g, 2.55 mmol) and p-bromo-benzaldehyde (706 mg, 3.82 mmol).

Step 2:

Was performed according to the description of Example 49, Step 2: N—[(S)-1-Benzyl-2-(4-benzyl-piperazin-1-yl)-2-oxo-ethyl]-N-(4-bromo-benzyl)-3-(4-trifluoromethyl-phenyl)-acrylamide (0.80 g, 40%, LC-MS: $t_R$=0.99 min; [M+H]$^+$=692.66) was obtained from 1-(4-benzyl-piperazin-1-yl)-2-(4-bromo-benzylamino)-(S)-3-phenyl-propan-1-one (1.4 g, 2.84 mmol) and trans-4-(trifluoromethyl)cinnamic acid (1.33 g, 5.68 mmol).

Step 3:

In an inert atmosphere, N—[(S)-1-benzyl-2-(4-benzyl-piperazin-1-yl)-2-oxo-ethyl]-N-(4-bromo-benzyl)-3-(4-trifluoromethyl-phenyl)-acrylamide (60 mg, 0.087 mmol) was dissolved in toluene (0.5 mL) followed by the addition of 3-pyridineboronic acid (11 mg, 0.087 mmol), 2M potassium carbonate solution (0.5 mL) and iso-propanol (0.5 mL). The mixture was degassed with argon for 5 min and heated to 100° C. followed by the addition of tetrakis-(triphenylphosphine) palladium (3 mg, 0.003 mmol). The mixture was stirred for 3 h at 110° C., cooled to rt again and water (1 mL) was added. The product was extracted with EtOAc (3×3 mL). The combined organic layers were evaporated to dryness and the residue was purified by prep. HPLC to give 21 mg (35%) of N—[(S)-1-benzyl-2-(4-benzyl-piperazin-1-yl)-2-oxo-ethyl]-N-(4-pyridin-3-yl-benzyl)-3-(4-trifluoromethyl-phenyl)-acrylamide. LC-MS: $t_R$=0.85 min; [M+H]$^+$=689.68.

Example 75

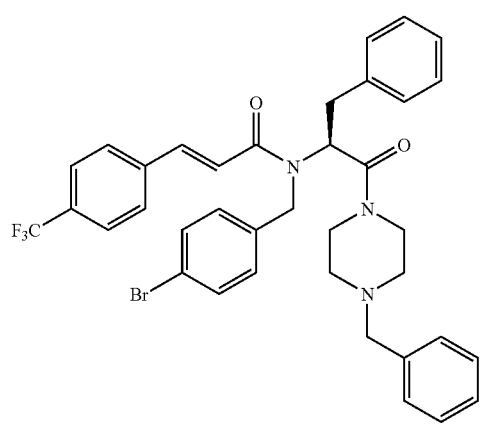

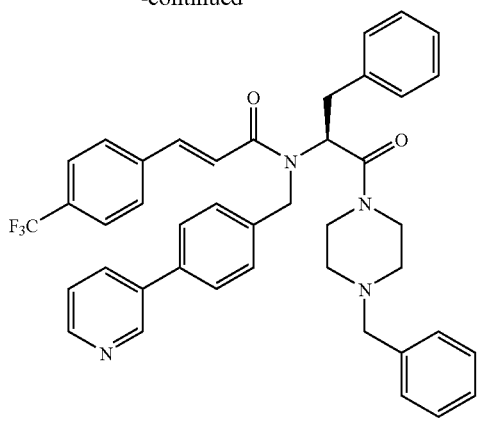

Example 75:
LC-MS:
$t_R$ = 0.83
[M + H]$^+$ = 689.7

According to the procedure described in Example 74, Step 3, N—[(S)-1-benzyl-2-(4-benzyl-piperazin-1-yl)-2-oxo-ethyl]-N-(4-pyridin-3-yl-benzyl)-3-(4-trifluoromethyl-phenyl)-acrylamide (13 mg, 20%, LC-MS: $t_R$=0.83 min; [M+H]$^+$=689.7) was obtained from N—[(S)-1-benzyl-2-(4-benzyl-piperazin-1-yl)-2-oxo-ethyl]-N-(4-bromo-benzyl)-3-(4-trifluoromethyl-phenyl)-acrylamide (60 mg, 0.087 mmol) and 4-pyridineboronic acid (11 mg, 0.087 mmol).

Examples 76 to 102 were obtained according to procedures described for the preparation of Example 1:

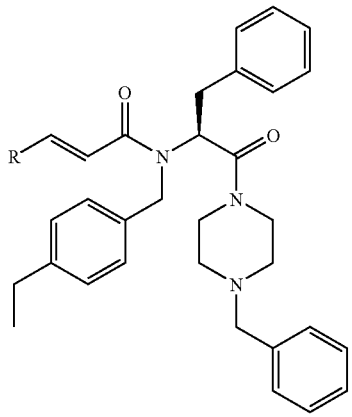

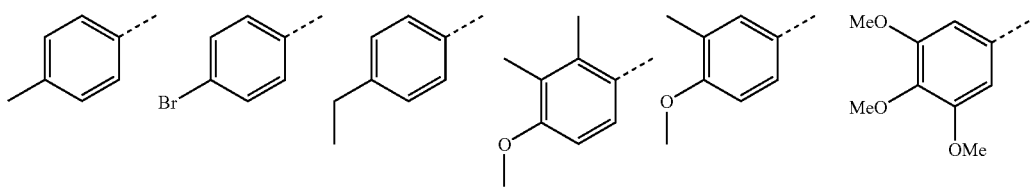

| LC-MS | | | | | | |
|---|---|---|---|---|---|---|
| Ex-No.: | 76 | 77 | 78 | 79 | 80 | 81 |
| $t_R$ = | 0.96 | 0.98 | 0.97 | 1.00 | 0.98 | 0.93 |
| [M + H]+ = | 586.49 | 652.41 | 620.3 | 630.35 | 616.38 | 666.55 |

-continued
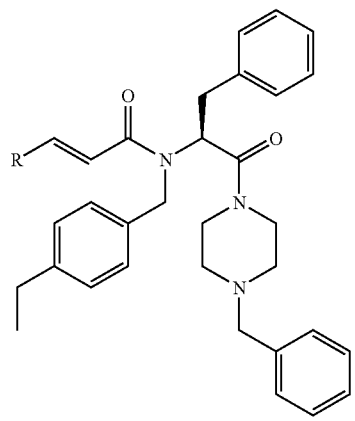
| | R | | | | | |
|---|---|---|---|---|---|---|
| LC-MS | 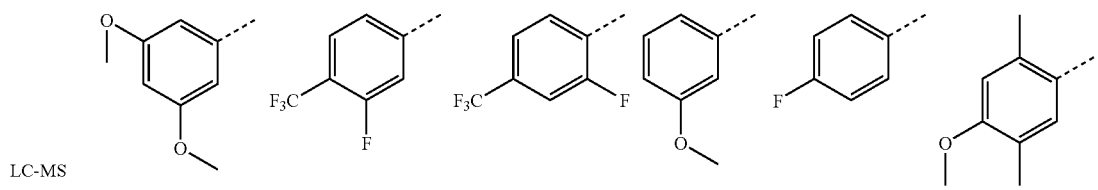 | | | | | |
| Ex-No.: | 82 | 83 | 84 | 85 | 86 | 87 |
| $t_R$ = | 0.95 | 1.00 | 1.02 | 0.95 | 0.96 | 1.00 |
| [M + H]+ = | 616.54 | 658.31 | 658.28 | 602.78 | 590.63 | 630.36 |
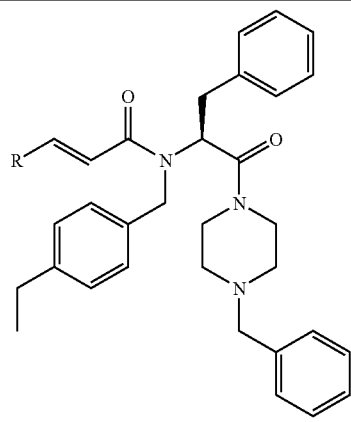
| | R | | | | | |
|---|---|---|---|---|---|---|
| LC-MS | 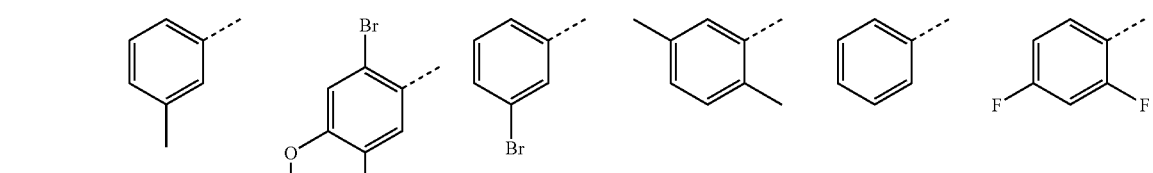 | | | | | |
| Ex-No.: | 88 | 89 | 90 | 91 | 92 | 93 |
| $t_R$ = | 0.97 | 0.97 | 0.97 | 0.98 | 0.96 | 0.95 |
| [M + H]+ = | 586.46 | 712.38 | 652.42 | 500.54 | 572.48 | 608.51 |

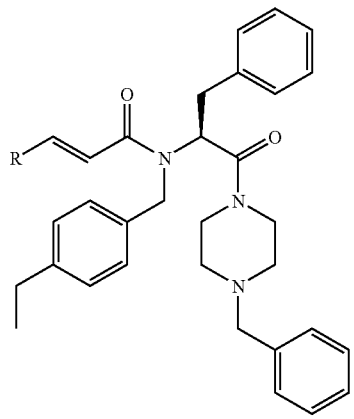
| | R | | | | | |
|---|---|---|---|---|---|---|
| LC-MS | Br—⌬—F | ⌬—F | —O—⌬—O— | F₃C—⌬—F (3,5) | F₃C—⌬—F | F—⌬—F |
| Ex-No.: | 94 | 95 | 96 | 97 | 98 | 99 |
| $t_R =$ | 0.99 | 0.95 | 0.96 | 1.01 | 1.00 | 0.96 |
| $[M + H]^+ =$ | 670.41 | 590.48 | 632.54 | 658.31 | 658.47 | 608.51 |
| | | | R | | |
|---|---|---|---|---|---|
| LC-MS | | | ⌬—Br | ⌬—CH₃ | ⌬—CF₃ |
| Ex-No.: | | | 100 | 101 | 102 |
| $t_R =$ | | | 0.98 | 0.97 | 0.98 |
| $[M + H]^+ =$ | | | 652.66 | 586.49 | 640.48 |
Example 103 was prepared according to the procedure described for Example 112:
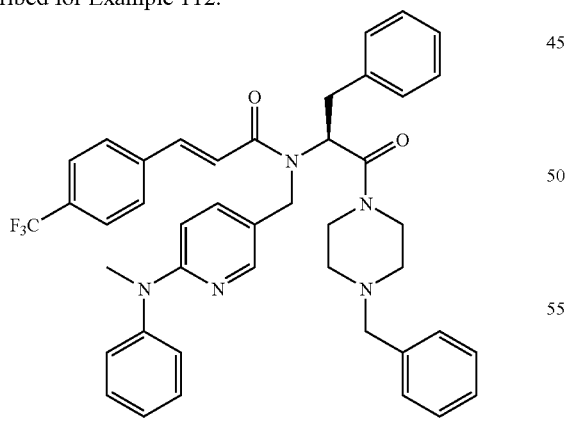
Example 103:
LC-MS:
$t_R = 0.87$
$[M + H]^+ = 718.34$
Examples 104 to 108 were obtained according to procedures described for the preparation of Example 1 using D-phenylalanine as the starting material:

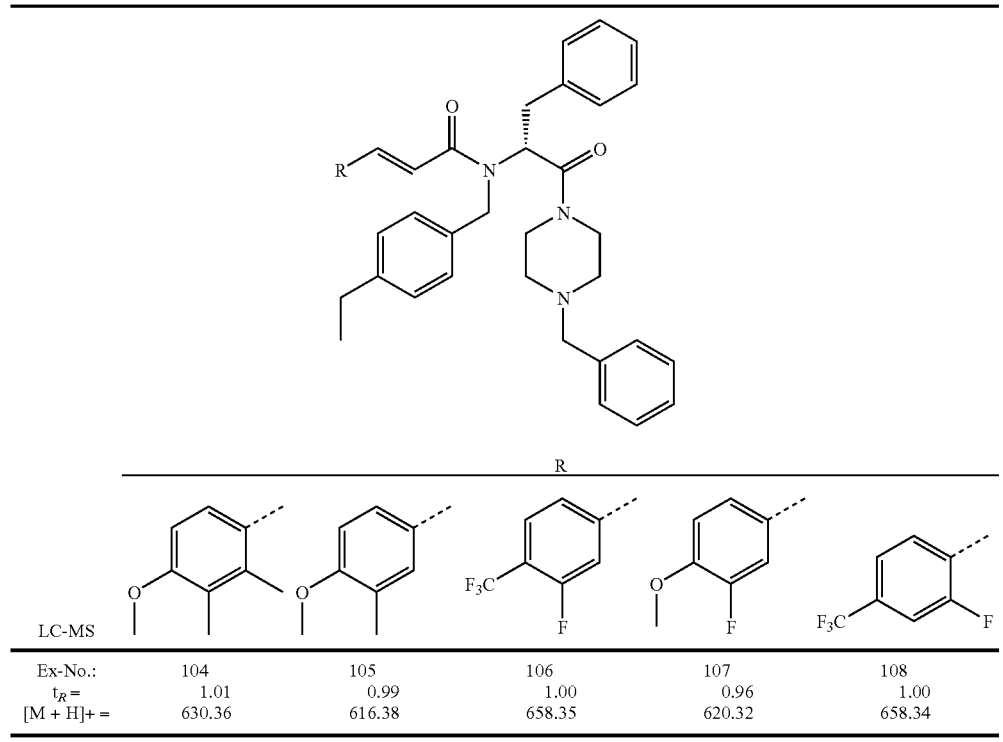

| | | | | | |
|---|---|---|---|---|---|
| LC-MS | | | | | |
| Ex-No.: | 104 | 105 | 106 | 107 | 108 |
| $t_R =$ | 1.01 | 0.99 | 1.00 | 0.96 | 1.00 |
| $[M + H]+ =$ | 630.36 | 616.38 | 658.35 | 620.32 | 658.34 |

Example 109

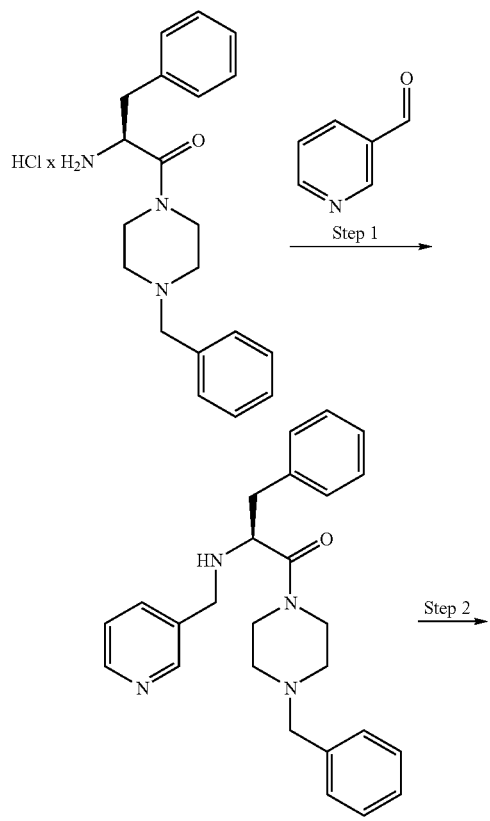

Intermediate:
LC-MS:
$t_R = 0.59$
$[M + H]^+ = 415.27$

-continued

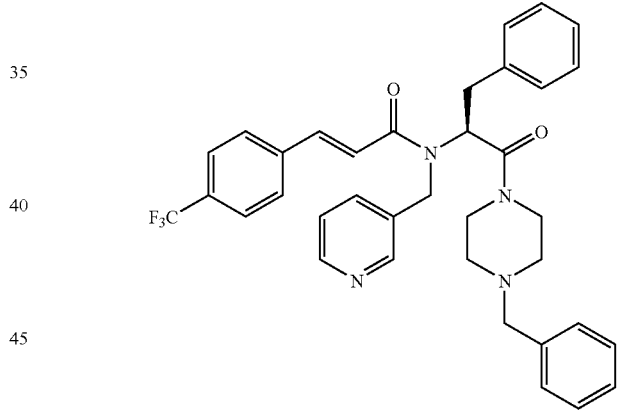

Example 109:
LC-MS:
$t_R = 0.80$
$[M + H]^+ = 613.61$

Step 1:

Was performed according to the description of Example 49, Step 1: 1-(4-Benzyl-piperazin-1-yl)-(S)-3-phenyl-2-[(pyridin-3-ylmethyl)-amino]-propan-1-one (200 mg, quant. yield, LC-MS: $t_R$=0.59 min; [M+H]$^+$=415.27) was obtained from 2-amino-1-(4-benzyl-piperazin-1-yl)-(S)-3-phenyl-propan-1-one (162 mg, 0.50 mmol) and pyridine-3-carbaldehyde (80 mg, 0.75 mmol).

Step 2:

Was performed according to the description of Example 49, Step 2: N—[(S)-1-Benzyl-2-(4-benzyl-piperazin-1-yl)-2-oxo-ethyl]-N-pyridin-3-ylmethyl-3-(4-trifluoromethyl-phenyl)-acrylamide (20 mg, 18%, LC-MS: $t_R$=0.80 min; [M+H]$^+$=613.61) was obtained from 1-(4-benzyl-piperazin- 1-yl)-(S)-3-phenyl-2-[(pyridin-3-ylmethyl)-amino]-propan-1-one (75 mg, 0.18 mmol) and trans-4-(trifluoromethyl)cinnamic acid (50 mg, 0.216 mmol).

Example 110 step 1: N—[(S)-1-Benzyl-2-(4-benzyl-piperazin-1-yl)-2-oxo-ethyl]-N-pyridin-2-ylmethyl-3-(4-trifluoromethyl-phenyl)-acrylamide. (39 mg, 45%, LC-MS: $t_R$=0.87 min; $[M+H]^+$=613.49.)

Example 111

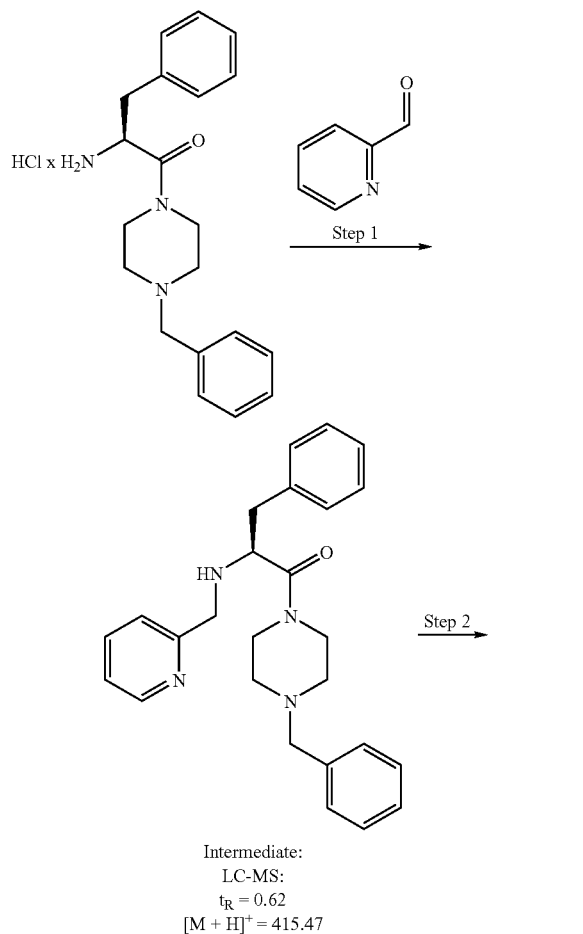

Intermediate:
LC-MS:
$t_R = 0.62$
$[M + H]^+ = 415.47$

Example 110:
LC-MS:
$t_R = 0.87$
$[M + H]^+ = 613.49$

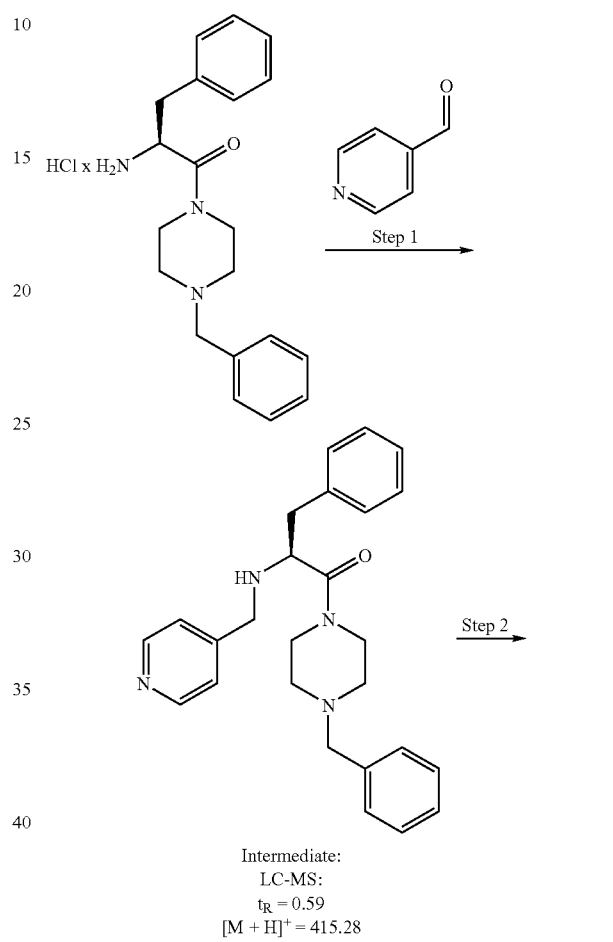

Intermediate:
LC-MS:
$t_R = 0.59$
$[M + H]^+ = 415.28$

Example 111:
LC-MS:
$t_R = 0.79$
$[M + H]^+ = 613.64$

Example 110 was prepared according to the procedures described for the preparation of Example 109 by using pyridine-2-carbaldehyde instead of pyridine-3-carbaldehyde in Example 111 was prepared according to the procedures described for the preparation of Example 109 by using pyridine-4-carbaldehyde instead of pyridine-3-carbaldehyde in step 1: N—[(S)-1-Benzyl-2-(4-benzyl-piperazin-1-yl)-2-oxo-ethyl]-N-pyridin-4-ylmethyl-3-(4-trifluoromethyl-phenyl)-acrylamide. (32 mg, 29%, LC-MS: $t_R$=0.79 min; [M+H]$^+$=613.64.)

Example 112

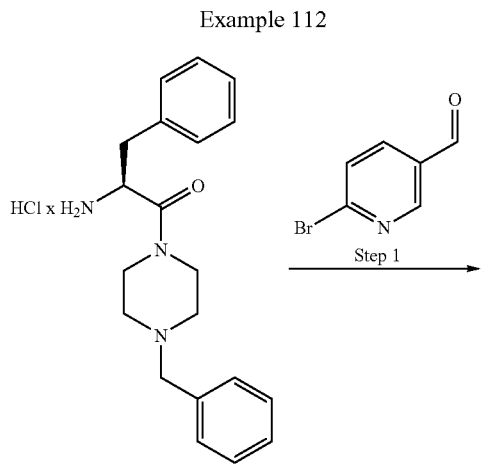

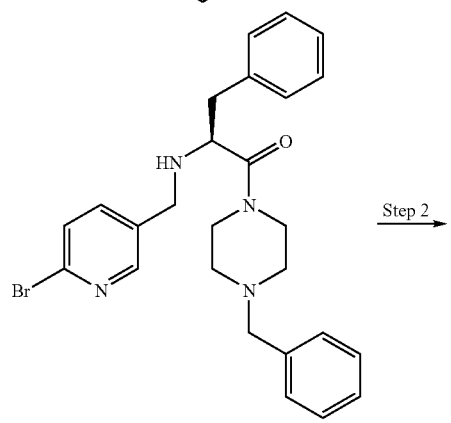

Intermediate:
LC-MS:
$t_R$ = 0.64
[M + H]$^+$ = 495.23

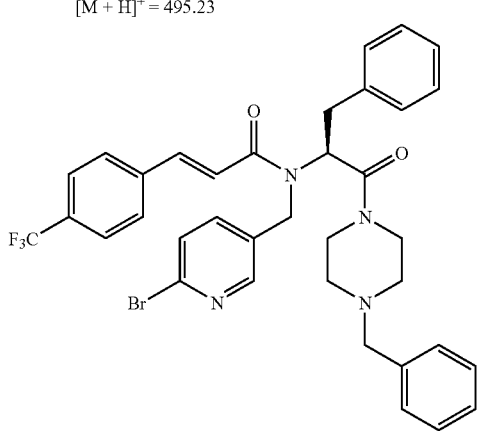

Intermediate 2:
LC-MS:
$t_R$ = 0.93
[M + H]$^+$ = 693.58

Step 3

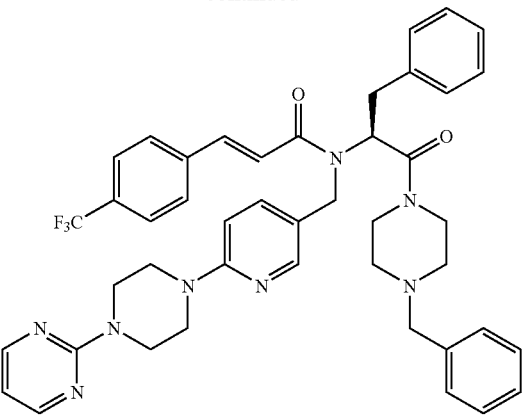

Example 112:
LC-MS:
$t_R$ = 0.85
[M + H]$^+$ = 775.36

Step 1:

Was performed according to the description of Example 49, Step 1: 1-(4-Benzyl-piperazin-1-yl)-2-[(6-bromo-pyridin-3-ylmethyl)-amino]-(S)-3-phenyl-propan-1-one (300 mg, quant. yield, LC-MS: $t_R$=0.64 min; [M+H]$^+$=495.23) was obtained from 2-amino-1-(4-benzyl-piperazin-1-yl)-(S)-3-phenyl-propan-1-one (210 mg, 0.65 mmol) and 6-bromo-pyridine-3-carbaldehyde (480 mg, 2.6 mmol).

Step 2:

Was performed according to the description of Example 49, Step 2: N—[(S)-1-Benzyl-2-(4-benzyl-piperazin-1-yl)-2-oxo-ethyl]-N-(6-bromo-pyridin-3-ylmethyl)-3-(4-trifluoromethyl-phenyl)-acrylamide (2.0 mg, quant. yield, LC-MS: $t_R$=0.93 min; [M+H]$^+$=693.58) was obtained from 1-(4-benzyl-piperazin-1-yl)-2-[(6-bromo-pyridin-3-ylmethyl)-amino]-(S)-3-phenyl-propan-1-one (1.37 g, 2.77 mmol) and trans-4-(trifluoromethyl)cinnamic acid (720 mg, 3.33 mmol).

Step 3:

In an inert atmosphere, 1-(4-benzyl-piperazin-1-yl)-2-[(6-bromo-pyridin-3-ylmethyl)-amino]-(S)-3-phenyl-propan-1-one (55 mg, 0.08 mmol) was dissolved in dioxane (1 mL) and 1-(2-pyrimidyl)piperazine (20 mg, 0.12 mmol) and sodium tert.-butoxide (11.5 mg, 0.12 mmol) were added. The reaction mixture was degassed with argon and heated to 105° C. followed by the addition of SK-CC02-A (Palladium-catalyst; 3 mg, 0.005 mmol) dissolved in dioxane (0.5 mL). Stirring was continued for 12 h. The reaction mixture was cooled to rt, water (1 mL) was added and the product was extracted with EtOAc (3×32 mL). The combined organic layers were concentrated under reduced pressure and the residue was purified by prep. HPLC to give 7 mg (11%) of N—[(S)-1-benzyl-2-(4-benzyl-piperazin-1-yl)-2-oxo-ethyl]-N-[6-(4-pyrimidin-2-yl-piperazin-1-yl)-pyridin-3-ylmethyl]-3-(4-trifluoromethyl-phenyl)-acrylamide. (LC-MS: $t_R$=0.85 min; [M+H]$^+$=775.36).

Examples 113 to 123 were prepared according to the procedure described for Example 112:
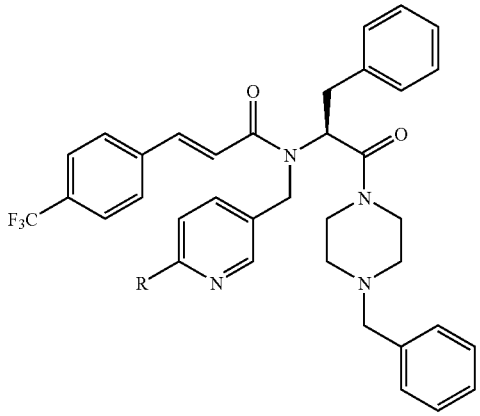
| | R | | | | | |
|---|---|---|---|---|---|---|
| LC-MS | 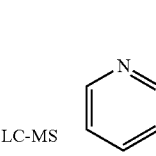 | 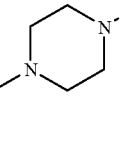 | 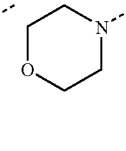 | 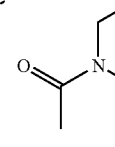 | 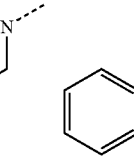 | 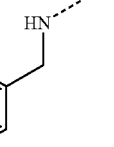 |
| Ex-No.: | 113 | 114 | 115 | 116 | 117 | 118 |
| $t_R =$ | 0.78 | 0.83 | 0.82 | 0.84 | 0.86 | 1.00 |
| $[M + H]+ =$ | 774.40 | 698.31 | 739.30 | 696.33 | 718.32 | 686.30 |
| | R | | | | |
|---|---|---|---|---|---|
| LC-MS | 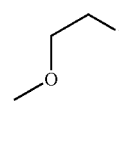 | 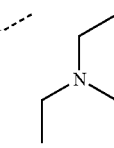 | 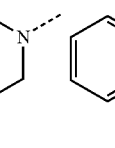 | 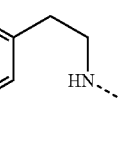 | 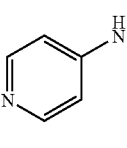 |
| Ex-No.: | 119 | 120 | 121 | 122 | 123 |
| $t_R =$ | 1.05 | 0.80 | 0.87 | 0.82 | 0.80 |
| $[M + H]+ =$ | 686.29 | 725.50 | 732.35 | 705.33 | 711.35 |
Example 124 was prepared according to the procedure described for Example 112:
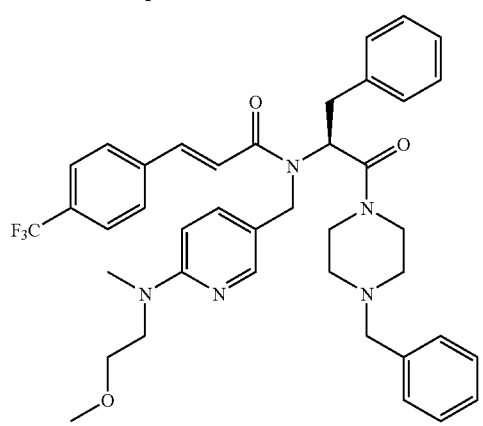
Example 124:
LC-MS:
$t_R = 1.00$
$[M + H]^+ = 686.30$
Example 125
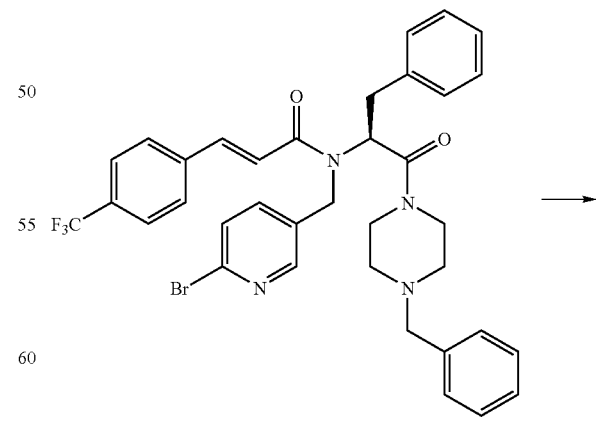
Intermediate:
LC-MS:
$t_R = 0.93$
$[M + H]^+ = 693.58$ Example 125
LC-MS:
$t_R = 0.84$
$[M + H]^+ = 690.17$ In an inert atmosphere, 1-(4-benzyl-piperazin-1-yl)-2-[(6-bromo-pyridin-3-ylmethyl)-amino]-(S)-3-phenyl-propan-1-one (50 mg, 0.072 mmol) was dissolved in toluene (0.5 mL). 4-Pyridineboronic acid (9.6 mg, 0.079 mmol), 2M potassium carbonate solution (0.5 mL) and isopropanol (0.5 ml) was added and the mixture was degassed with argon for 10 min, followed by the addition of tetrakis-(triphenylphosphine)palladium (2.5 mg, 0.002 mmol). The reaction mixture was heated to 100° C. for 12 h, cooled again to rt and water (1 mL) was added. The product was extracted with EtOAc (3×2 ml). The combined organic layers were concentrated under reduced pressure and the residue was purified by prep. HPLC to give 8.4 mg (17%) of N—[(S)-1-benzyl-2-(4-benzyl-piperazin-1-yl)-2-oxo-ethyl]-N-[2,4']bipyridinyl-5-ylmethyl-3-(4-trifluoromethyl-phenyl)-acrylamide. (LC-MS: $t_R$=0.84 min; $[M+H]^+$=690.17).

Examples 126 to 128 are prepared according to the procedure described for the preparation of Example 125:

Example 126

LC-MS:
$t_R = 0.85$
$[M + H]^+ = 690.72$

Example 127

LC-MS:
$t_R = 0.95$
$[M + H]^+ = 689.31$

Example 128

LC-MS:
$t_R = 0.87$
$[M + H]^+ = 690.75$

Example 129

Intermediate:
LC-MS:
$t_R = 0.93$
$[M + H]^+ = 693.58$

Example 135

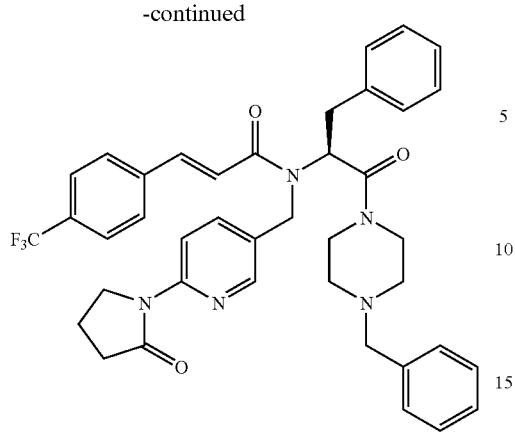

Example 129:
LC-MS:
$t_R = 1.02$
$[M + H]^+ = 688.46$

In an inert atmosphere, N—[(S)-1-benzyl-2-(4-benzyl-piperazin-1-yl)-2-oxo-ethyl]-N-(6-bromo-pyridin-3-ylmethyl)-3-(4-trifluoromethyl-phenyl)-acrylamide (70 mg, 0.101 mmol), 2-pyrrolidinon (10.3 mg, 0.121 mmol), potassium carbonate (27.9 mg, 0.202 mmol), copper(I)iodide (1 mg, 0.005 mmol) and N,N-dimethylenediamine (1 mg, 0.01 mmol) were dissolved in dioxane (1 mL). The reaction mixture was heated to 120° C. for 12 h, then filtered over a plug of silicagel with EtOAc, concentrated and purified by perp. HPLC to give 29 mg (52%) of N—[(S)-1-benzyl-2-(4-benzyl-piperazin-1-yl)-2-oxo-ethyl]-N-[6-(2-oxo-pyrrolidin-1-yl)-pyridin-3-ylmethyl]-3-(4-trifluoromethyl-phenyl)-acrylamide. (LC-MS: $t_R$=1.02 min; $[M+H]^+$=688.46).

Examples 130 to 134 were prepared according to the procedure described for the preparation of Example 129:

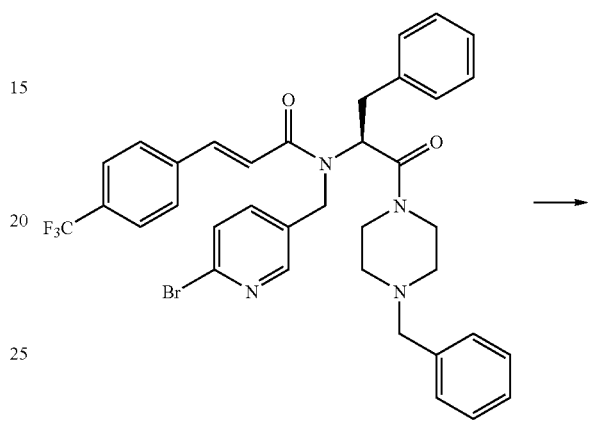

Intermediate:
LC-MS:
$t_R = 0.93$
$[M + H]^+ = 693.58$

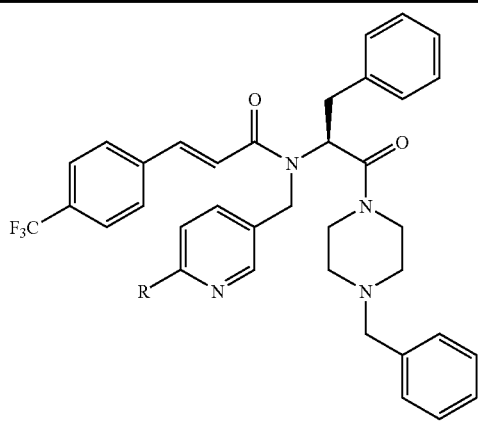

| LC-MS | R | | | | |
|---|---|---|---|---|---|
| | HO⤳C(O)NH— | PhC(O)N(CH₃)— attached via benzamide | cyclopropyl-C(O)NH— | 2-oxo-piperidin-1-yl | CH₃C(O)NH— |
| Ex-No.: | 130 | 131 | 132 | 133 | 134 |
| $t_R =$ | 0.95 | 1.04 | 1.02 | 1.01 | 0.97 |
| $[M + H]+ =$ | 686.18 | 745.92 | 696.25 | 710.27 | 670.24 |

Example 135:
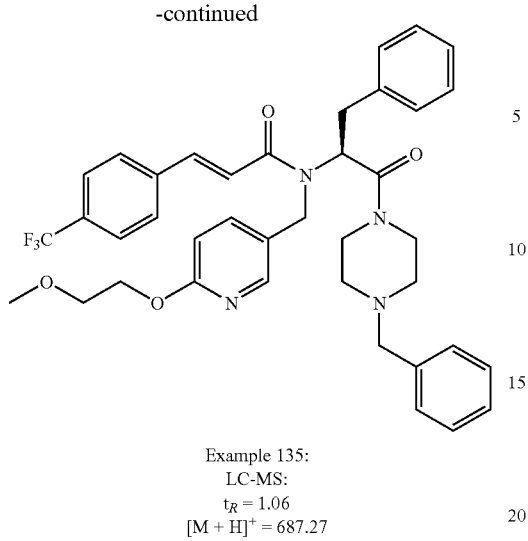
LC-MS:
$t_R = 1.06$
$[M + H]^+ = 687.27$

In an inert atmosphere, N—[(S)-1-benzyl-2-(4-benzyl-piperazin-1-yl)-2-oxo-ethyl]-N-(6-bromo-pyridin-3-ylmethyl)-3-(4-trifluoromethyl-phenyl)-acrylamide (80 mg, 0.116 mmol), was dissolved in dry toluene (3 mL) followed by the addition of 2-methoxy-ethanol (11.4 mg, 0.15 mmol), tris-(dibenzylideneaceton)-dipalladium (2.1 mg, 0.002 mmol), xanthphos (4 mg, 0.007 mmol) and sodium tert.-butoxide (16.7 mg, 0.174 mmol). The mixture was heated to 50° C. and stirring continued for 90 min. The reaction mixture was cooled to rt, brine (5 mL) was added and the product was extracted with EtOAc (3×4 ml). The combined organic layers were concentrated under reduced pressure and the residue was purified by prep. HPLC to give 38 mg (47%) of N—[(S)-1-benzyl-2-(4-benzyl-piperazin-1-yl)-2-oxo-ethyl]-N-[6-(2-methoxy-ethoxy)-pyridin-3-ylmethyl]-3-(4-trifluoromethyl-phenyl)-acrylamide. (LC-MS: $t_R$=1.06 min; $[M+H]^+$=687.27).

Examples 136 to 138 were prepared according to the procedure described for the preparation of Example 135:

Example 136

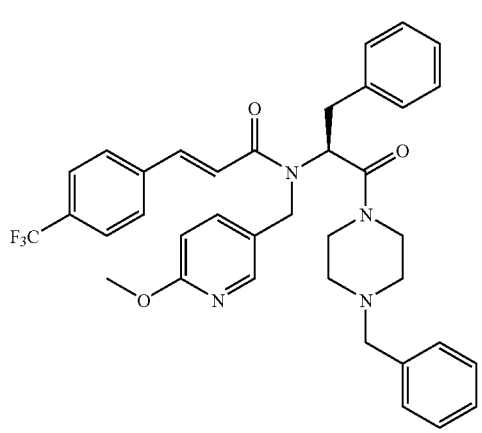

LC-MS:
$t_R = 1.07$
$[M + H]^+ = 643.21$

Example 137

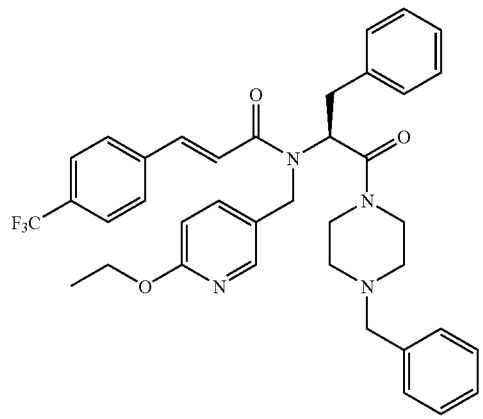

LC-MS:
$t_R = 1.11$
$[M + H]^+ = 657.22$

Example 138

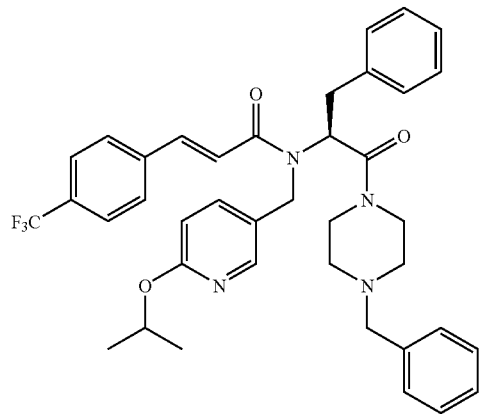

LC-MS:
$t_R = 1.14$
$[M + H]^+ = 671.28$

Examples 139-166 were prepared according to the procedure described for the preparation of Example 12:

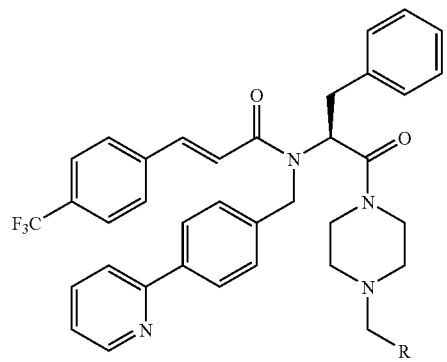

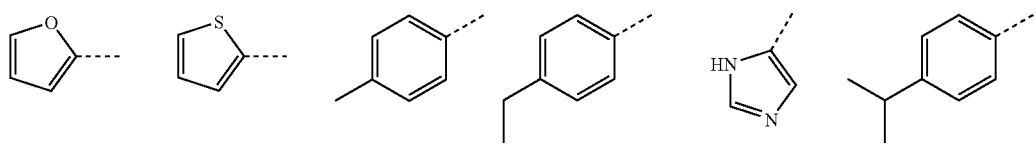

| | R | | | | | |
|---|---|---|---|---|---|---|
| LC-MS | furan-2-yl | thiophen-2-yl | 4-methylphenyl | 4-ethylphenyl | 1H-imidazol-5-yl | 4-isopropylphenyl |
| Ex-No.: | 139 | 140 | 141 | 142 | 143 | 144 |
| $t_R =$ | 0.88 | 0.87 | 0.90 | 0.92 | 0.77 | 0.97 |
| [M + H]+ = | 679.32 | 695.47 | 703.52 | 717.55 | 679.54 | 731.58 |

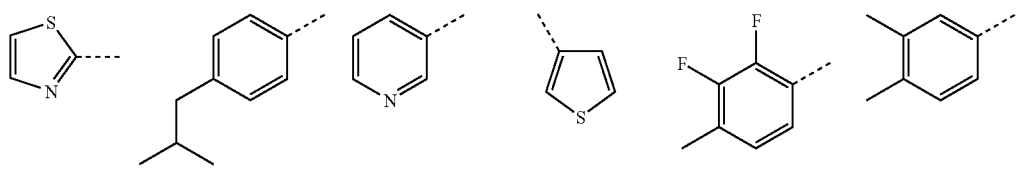

| | R | | | | | |
|---|---|---|---|---|---|---|
| LC-MS | thiazol-2-yl | 4-isobutylphenyl | pyridin-3-yl | thiophen-3-yl | 2,3-difluoro-4-methylphenyl | 3,4-dimethylphenyl |
| Ex-No.: | 145 | 146 | 147 | 148 | 149 | 150 |
| $t_R =$ | 0.86 | 0.96 | 0.82 | 0.88 | 0.91 | 0.92 |
| [M + H]+ = | 696.47 | 745.6 | 690.25 | 695.26 | 739.55 | 717.56 |

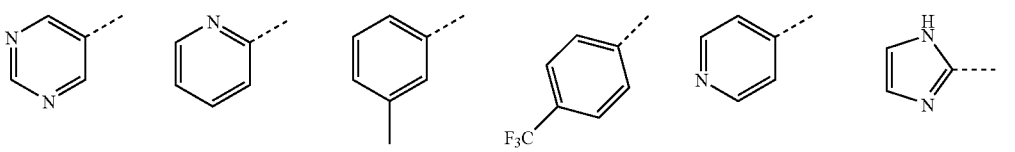

| | R | | | | | |
|---|---|---|---|---|---|---|
| LC-MS | pyrimidin-5-yl | pyridin-2-yl | 3-methylphenyl | 4-trifluoromethylphenyl | pyridin-4-yl | 1H-imidazol-2-yl |
| Ex-No.: | 151 | 152 | 153 | 154 | 155 | 156 |
| $t_R =$ | 0.82 | 0.86 | 0.91 | 0.92 | 0.82 | 0.80 |
| [M + H]+ = | 691.52 | 690.25 | 703.52 | 757.53 | 690.25 | 679.55 |

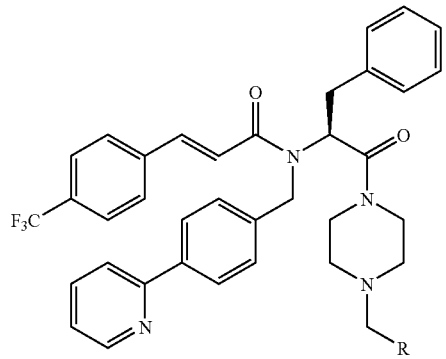
| | R | | | | | |
|---|---|---|---|---|---|---|
| LC-MS | 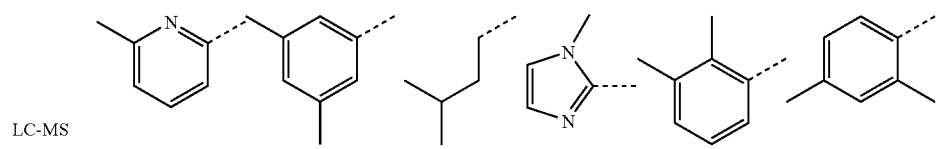 | | | | | |
| Ex-No.: | 157 | 158 | 159 | 160 | 161 | 162 |
| $t_R$ = | 0.85 | 0.92 | 0.89 | 0.82 | 0.91 | 0.94 |
| [M + H]+ = | 704.52 | 717.55 | 669.6 | 693.53 | 717.53 | 717.36 |
| | R | | | | |
|---|---|---|---|---|---|
| LC-MS | 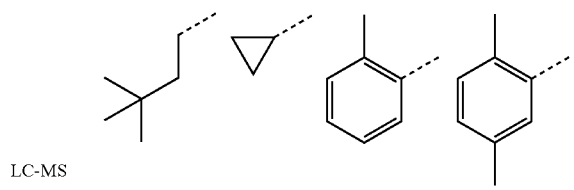 | | | | |
| Ex-No.: | 163 | 164 | 165 | 166 | |
| $t_R$ = | 0.90 | 0.85 | 0.91 | 0.90 | |
| [M + H]+ = | 683.6 | 653.54 | 703.36 | 717.37 | |

Examples 167 to 175 were prepared according to the procedures described for the preparation of Example 1:
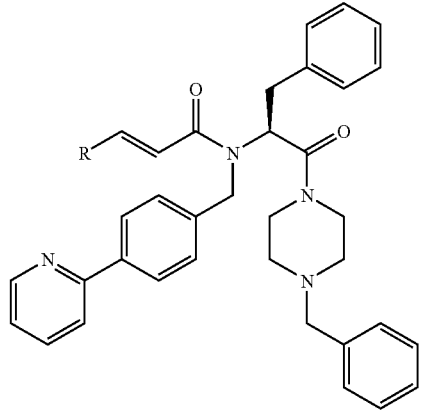
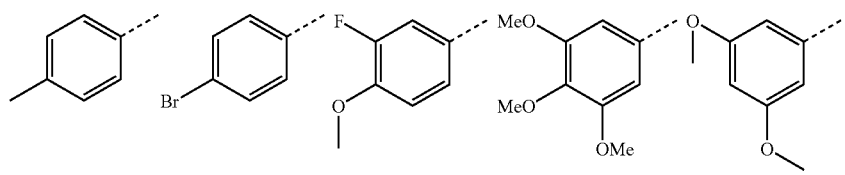
| LC-MS | | | | | |
|---|---|---|---|---|---|
| Ex-No.: | 167 | 168 | 159 | 170 | 171 |
| $t_R =$ | 0.83 | 0.84 | 0.85 | 0.81 | 0.81 |
| [M + H]+ = | 635.57 | 701.44 | 669.37 | 711.55 | 681.59 |
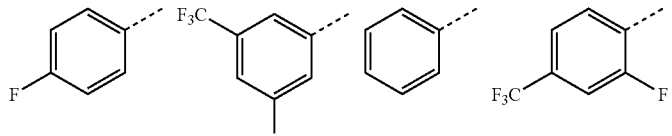
| LC-MS | | | | |
|---|---|---|---|---|
| Ex-No.: | 172 | 173 | 174 | 175 |
| $t_R =$ | 0.82 | 0.91 | 0.81 | 0.90 |
| [M + H]+ = | 639.59 | 707.44 | 621.57 | 707.31 |
The following compounds can be prepared according to the general procedures and the detailed experimental procedures described above:
-continued
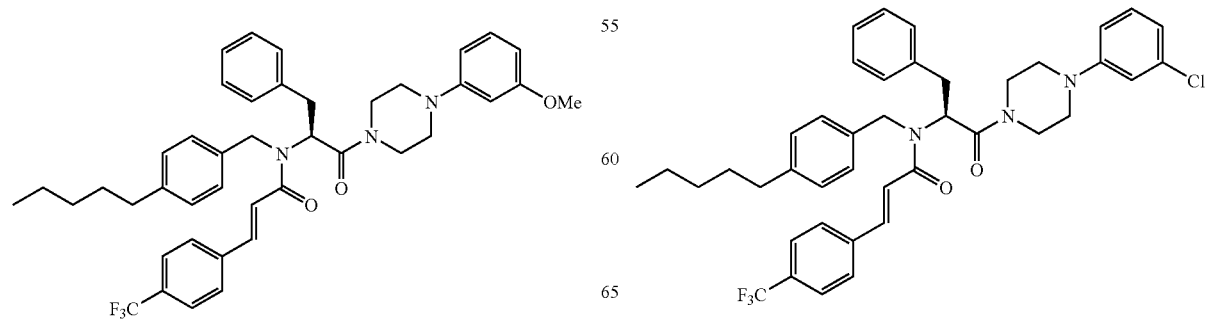

99
-continued
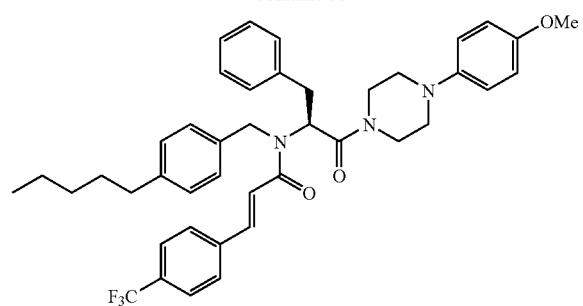
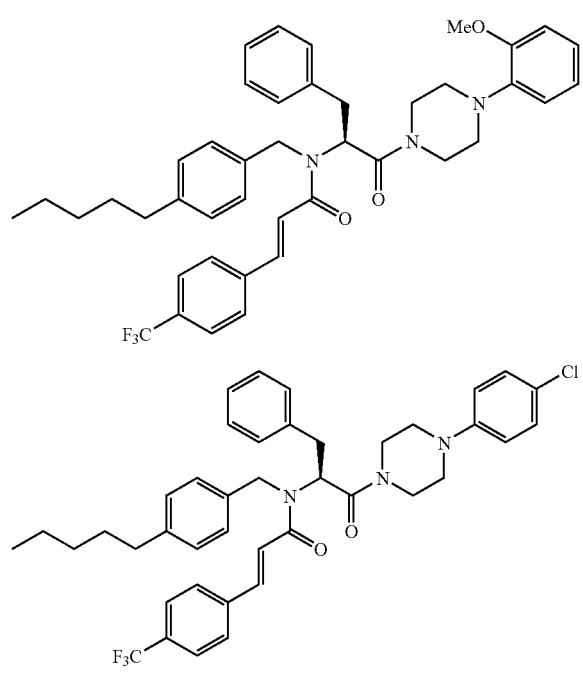
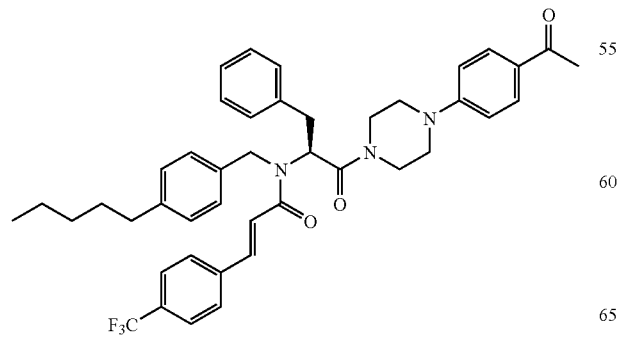
100
-continued
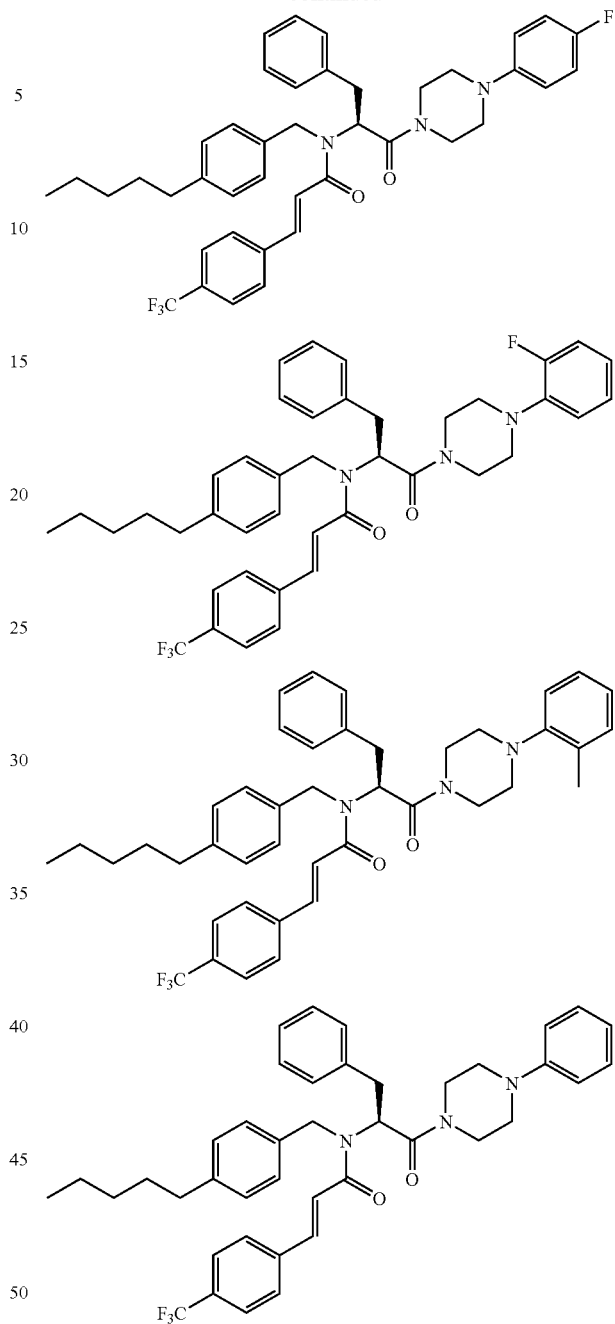

101
-continued
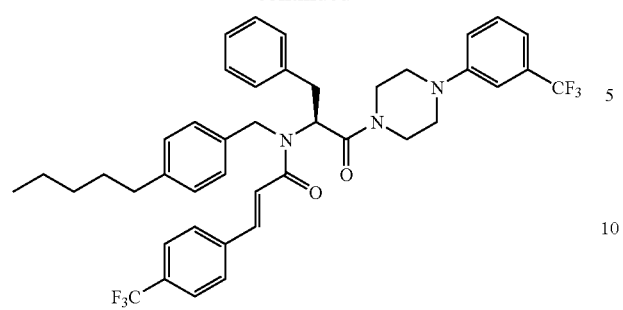
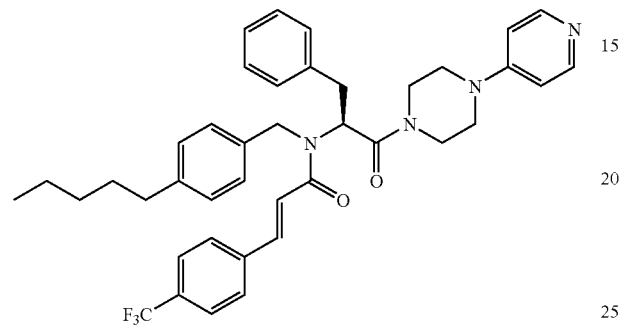
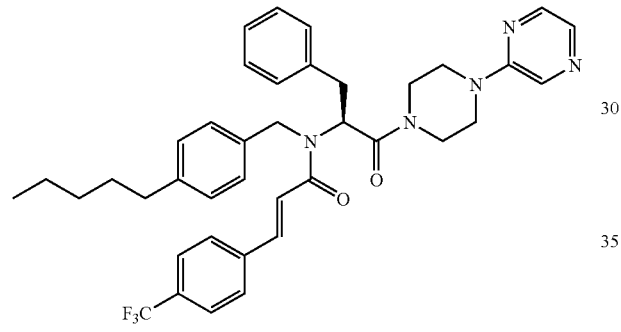
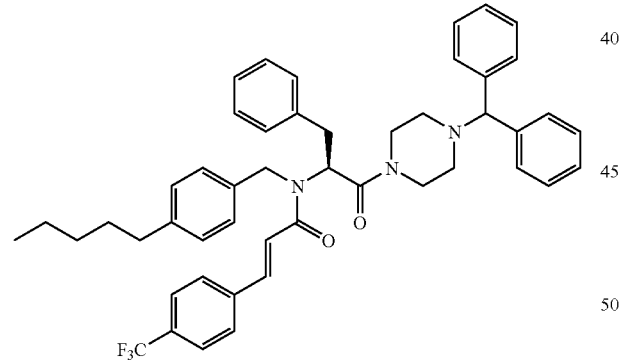
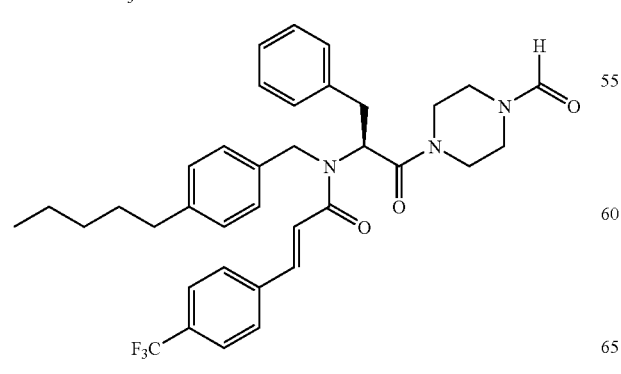
102
-continued
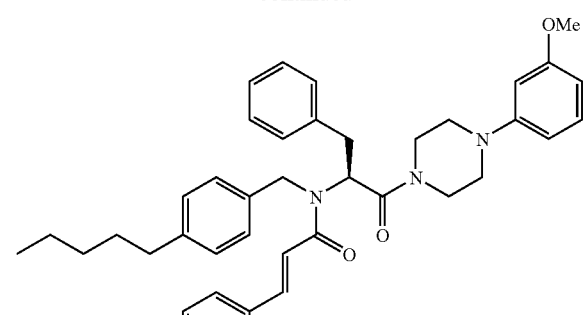
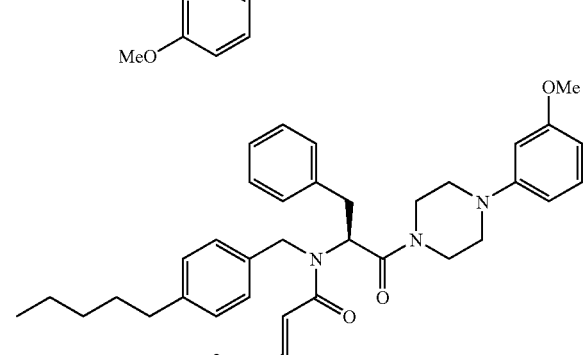
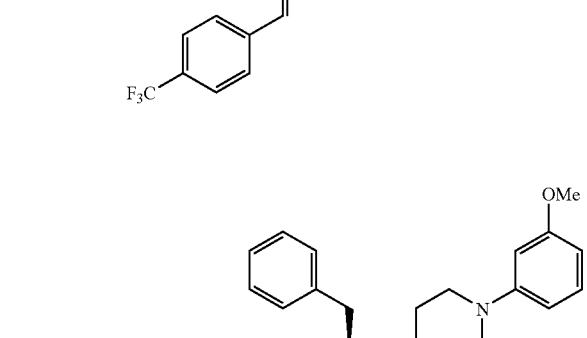
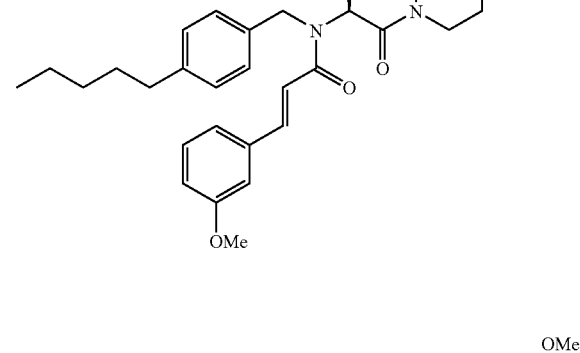
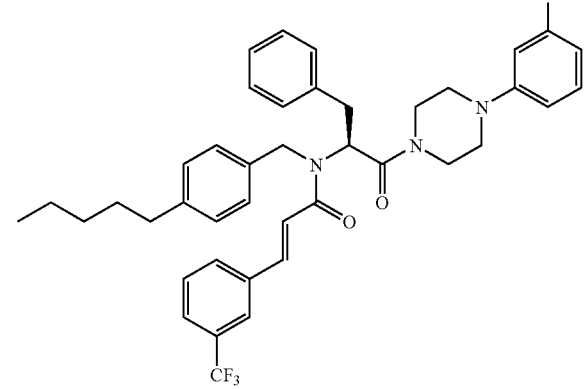

103
-continued
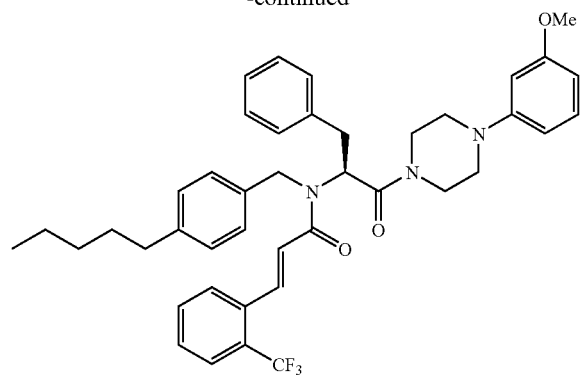
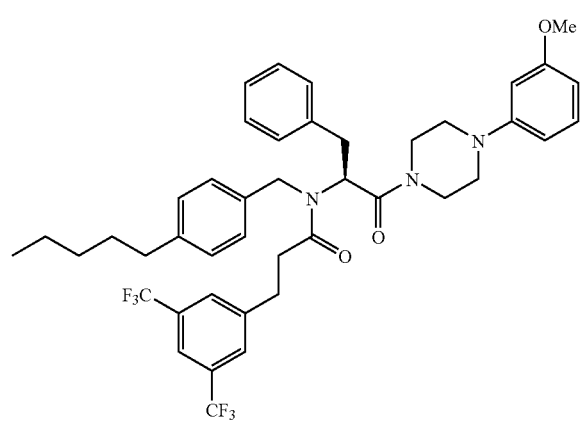
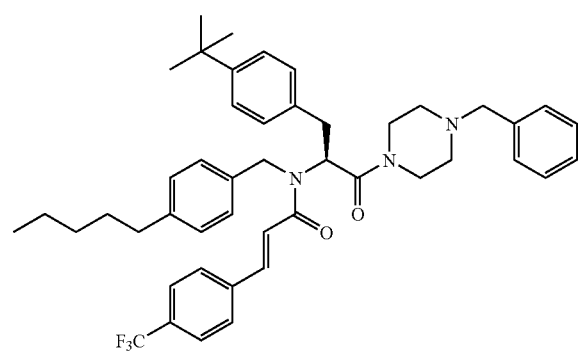
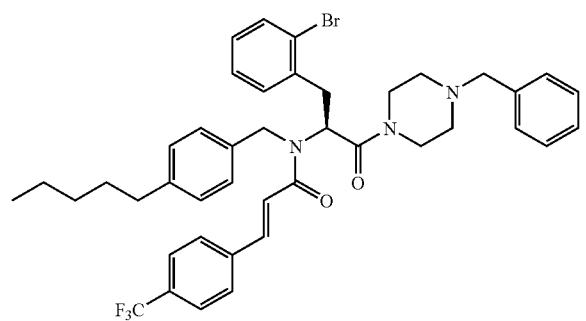
104
-continued
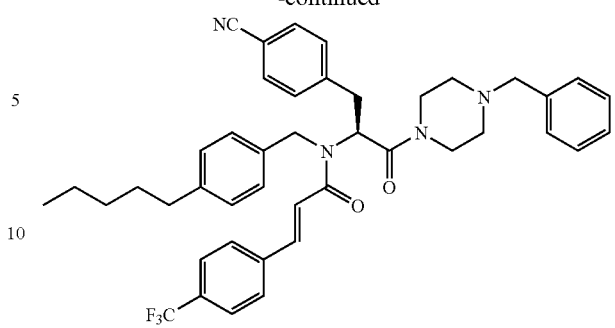
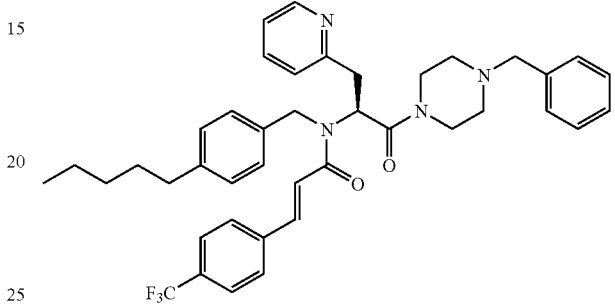
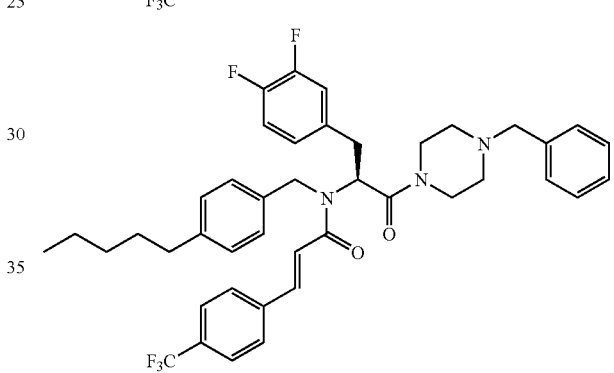
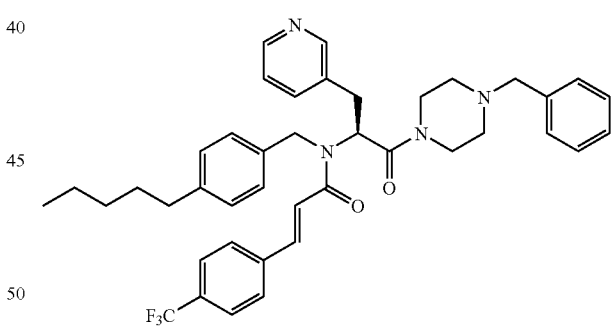
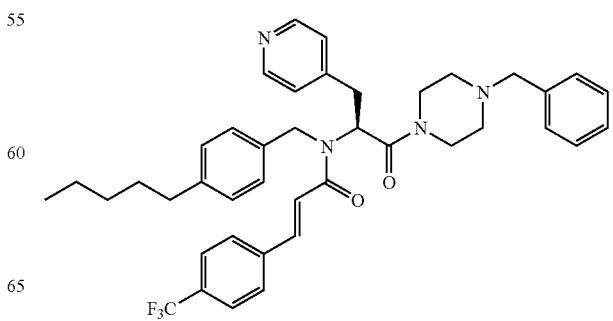

105
-continued
106
-continued
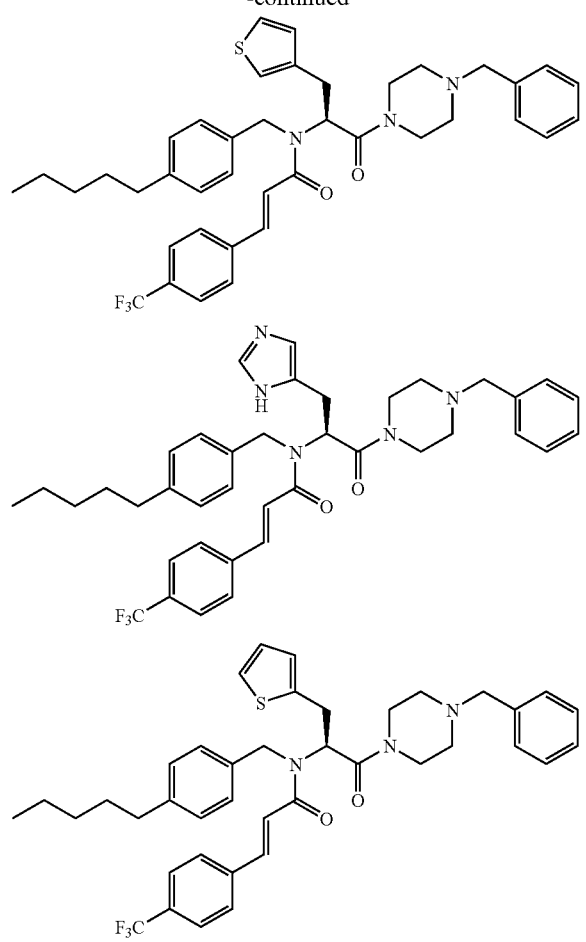
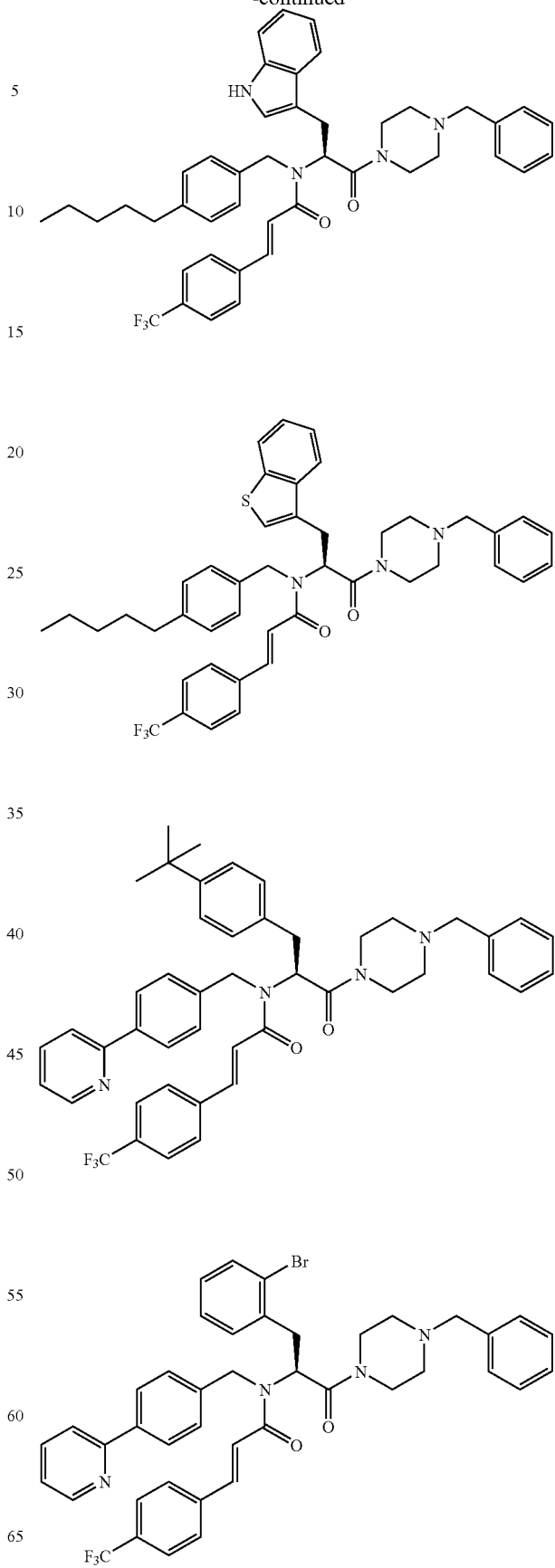

107
-continued
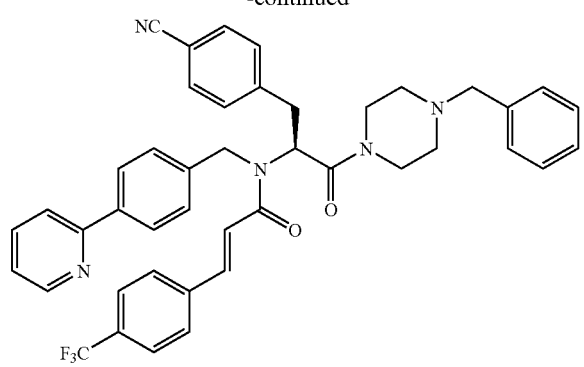
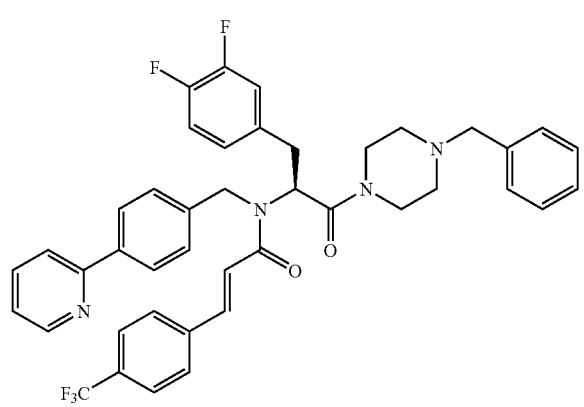
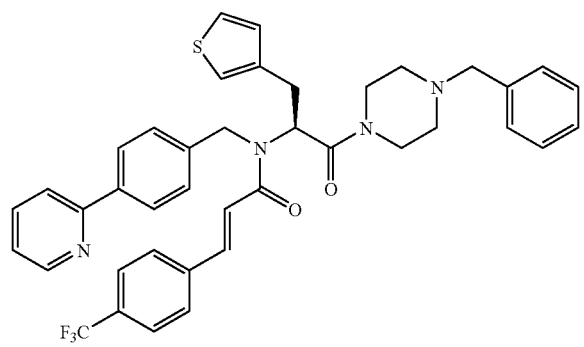
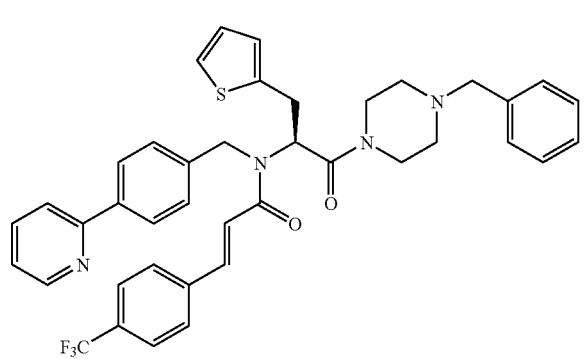
108
-continued
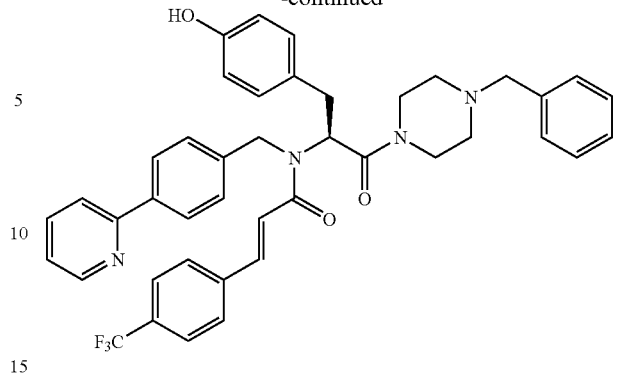
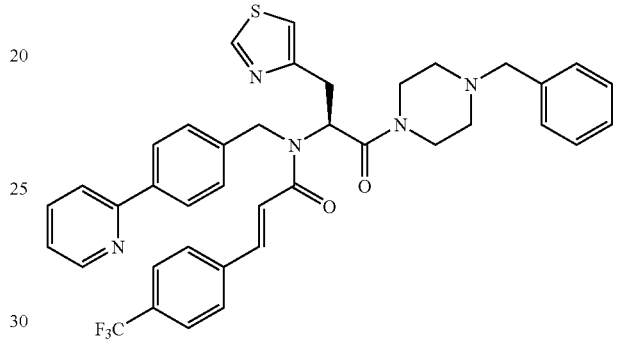
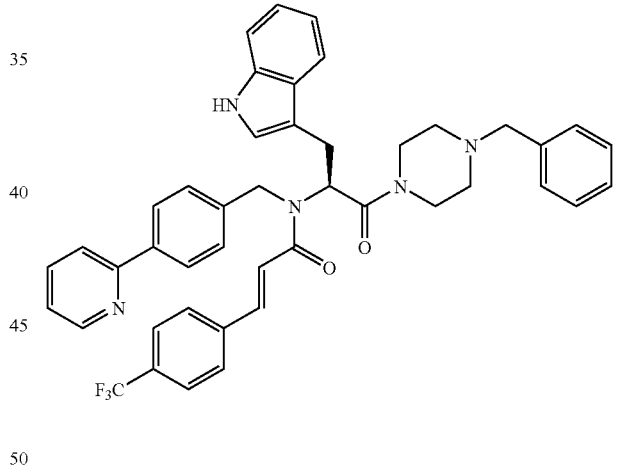
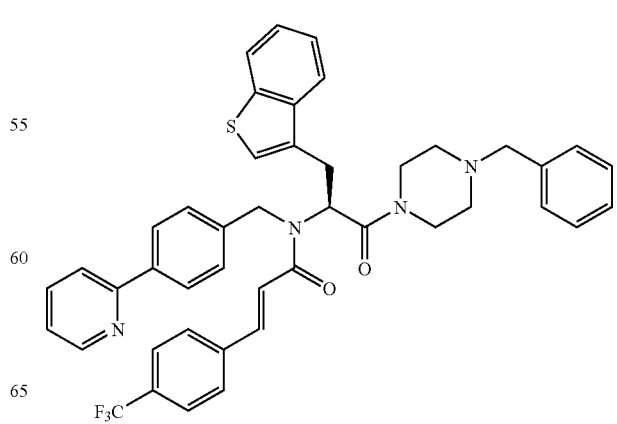

109
-continued
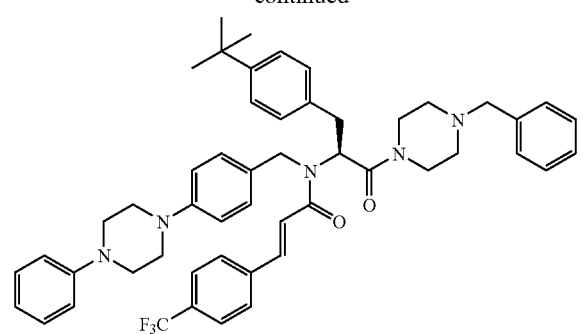
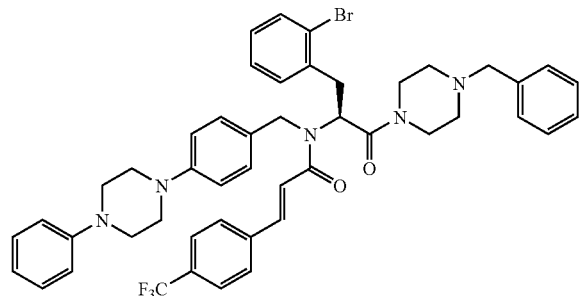
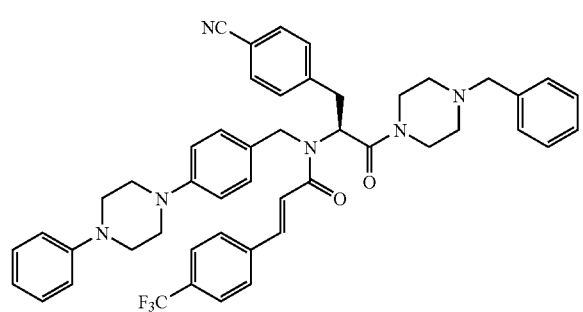
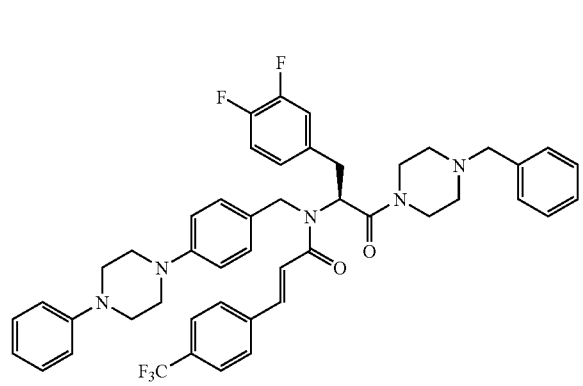
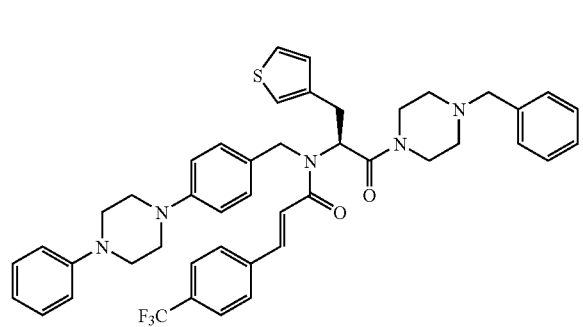
110
-continued
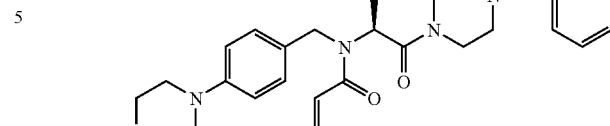
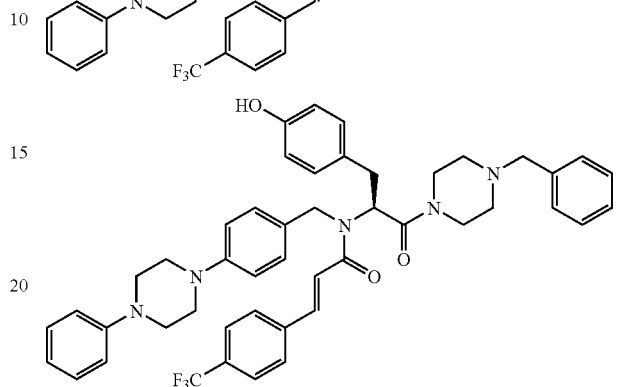
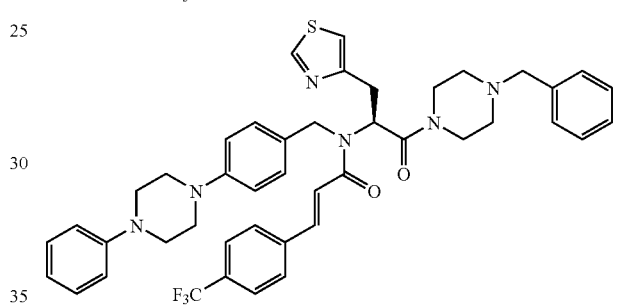
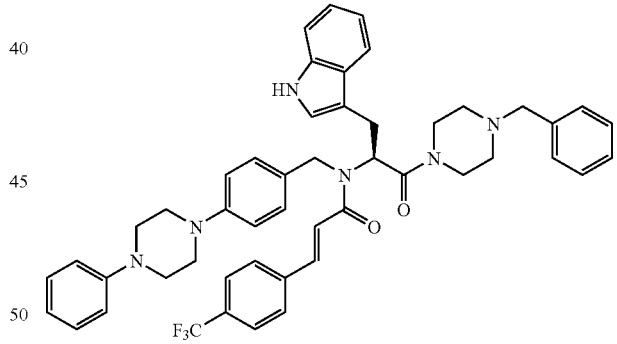
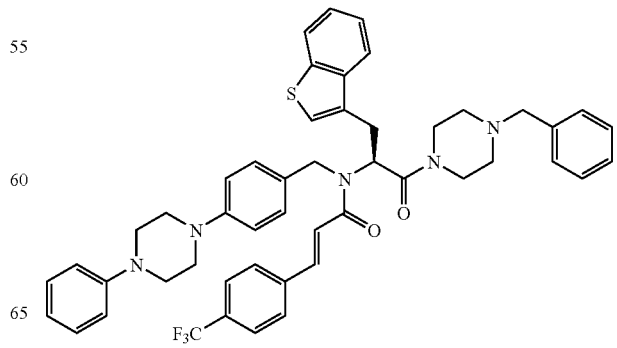

111
-continued
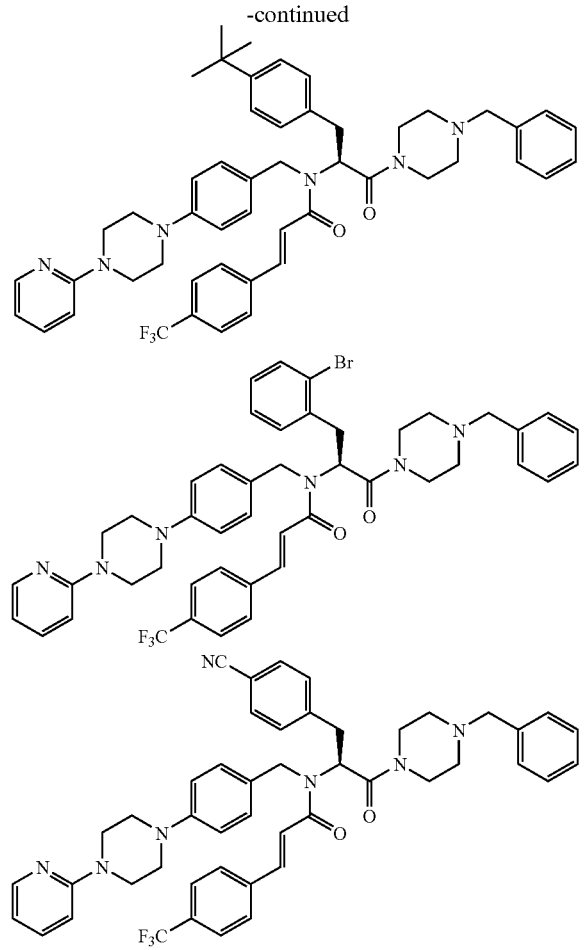
112
-continued
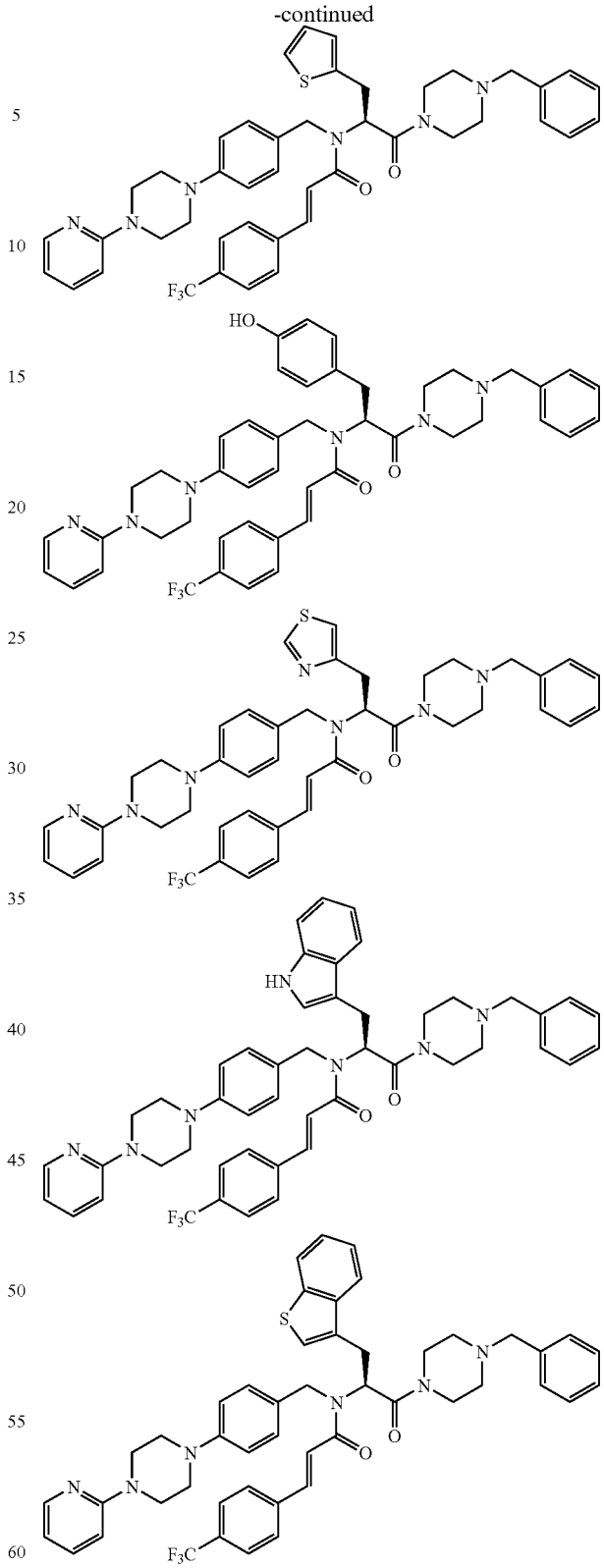
In Vitro Antimalarial Activity: *Plasmodium falciparum* In Vitro Assay
In vitro activity against erythrocytic stages of *P. falciparum* is determined using a [$^3$H] hypoxanthine incorporation assay. One strain resistant to chloroquine and pyrimethamine (*P.* falciparum K1) is used in the assays, and all test compounds are compared for activity with the standard drugs chloroquine (sigma C6628) and artemisinin (sigma-36, 159-3). Compounds are diluted in DMSO to 1 mM and added to parasite cultures incubated in RPMI 1640 medium without hypoxanthine, supplemented with HEPES (5.94 g/L), NaHCO$_3$ (2.1 g/L), neomycin (100 U/mL), Albumax (5 g/L) and washed human red cells at 2.5% haematocrit (0.3% parasitaemia). Seven serial doubling dilutions of each drug are prepared in 96-well microtitre plates and incubated in a humidifying atmosphere at 37° C.; 4% CO$_2$, 3% O$_2$, 93% N$_2$.

After 48 hours, 50 µl of [$^3$H] hypoxanthine (0.5 µCi) is added to each well of a plate. The plates are incubated for a further 24 hours under the same conditions. The plates are then harvested with a Betaplate cell harvester (Wallac) and washed with distilled water. The dried filters are inserted into a plastic foil with 10 mL of scintillation fluid, and counted in a Betaplate liquid scintillation counter. IC$_{50}$ values are calculated from sigmoidal inhibition curves using Microsoft Excel.

TABLE 1

IC$_{50}$ values (nM) for selected compounds:

| Compound of Example No.: | IC$_{50}$ (nM) on K1 |
|---|---|
| Example 1 | 3.8 |
| Example 2 | 70 |
| Example 3 | 375 |
| Example 4 | 7 |
| Example 5 | 19 |
| Example 6 | 588 |
| Example 15 | 11 |
| Example 29 | 7.5 |
| Example 33 | 6.9 |
| Example 37 | 18 |
| Example 38 | 11 |
| Example 43 | 8.3 |
| Example 81 | 7.4 |
| Example 87 | 13 |
| Example 125 | 4.8 |
| Example 129 | 9.5 |
| Example 159 | 2.4 |
| Chloroquine | 300 |
| Artemisinin | 2 |

In Vivo Antimalarial Efficacy Studies

In vivo antimalarial activity is assessed for groups of three female NMRI mice (20-22 g) intravenously infected on day 0 with *P. berghei* strain GFP-ANKA (0.2 mL heparinized saline suspension containing 2×10$^7$ parasitized erythrocytes). In control mice, parasitaemia typically rise to approximately 40% by day 3 after infection, and control mice die between day 5 and day 7 after infection. For the mice treated with compounds, compounds are either formulated in an aqueous-gelatine vehicle with 3 mg/mL compounds or in tween 80/ethanol (7%/3%) with 5 mg/mL.

Compounds are administered intraperitonealy or subcoutaneously either as two consecutive twice-daily dosings (BID) (2×75 mg/kg BID, 24 and 48 hours after infection) or as four consecutive daily doses (4×10 mg/kg or 4×50 mg/kg, 3, 24, 48 and 72 hours after infection). With the double BID-dose regimen, 24 hours after the last drug treatment, 1 µl tail blood is taken, resuspended in 1 mL PBS buffer and parasitemia determined with a FACScan (Becton Dickinson) by counting 100 000 red blood cells. Tail blood samples for the quadruple-dose regimen are processed on day 4 after infection. Activity is calculated as the difference between the mean value of the control and treated groups expressed as a percent relative to the control group. For parasetimias lower than 0.1%, the presence of parasites in the FACS gate is checked visually. The survival days of infected mice treated with compound is also recorded for each compound. Mice surviving for 30 days are checked for parasitemia and subsequently euthanised. A compound is considered curative if the animal survives to day 30 post-infection with no detectable parasites.

The invention claimed is:
1. A compound selected from the group consisting of a compound of the formula I:

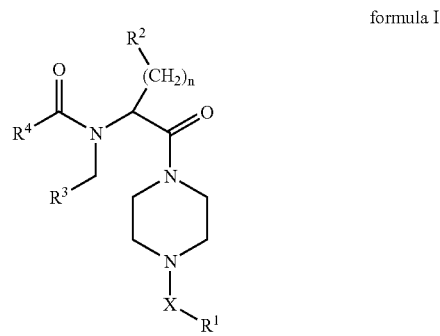

formula I wherein
X represents —(CH$_2$)$_{0-2}$— or —C(=O)—;
n represents the integer 0, 1 or 2;
R$^1$ represents hydrogen; alkyl; cycloalkyl; ethoxy-carbonyl; hydroxy-ethyl; benzo[1,3]dioxolyl; aryl that can be mono-, di-, tri-, or tetra-substituted, wherein the substituents are independently selected from halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —CF$_3$, —OCF$_3$, hydroxy, alkoxy-carbonyl, and carboxyl; furanyl that can be mono-, or di-substituted, wherein the substituents are independently selected from methyl, hydroxy-methyl, and bromine; thienyl that can be mono-substituted with methyl or chlorine; pyrimidinyl that can be mono-substituted with alkyl, halogen, cyclopropyl, CH$_3$—S—, or methylsulfonyl or that can be mono- or di-substituted with methoxy; pyridazinyl; benzothienyl; benzofuranyl; quinolinyl; isoquinolinyl; benzhydryl, wherein both phenyl rings can be mono- or di-substituted, wherein the substituents are independently selected from halogen, alkyl, alkoxy, —CF$_3$, —OCF$_3$, hydroxy, cyano, alkoxy-carbonyl, and alkyl-carbonyl; imidazolyl optionally mono-substituted with alkyl; thiazolyl; or oxazolyl;
R$^2$ represents hydrogen; alkyl; indolyl; carboxyl; alkoxy-carbonyl; amino-carbonyl; imidazolyl optionally mono-substituted with alkyl; cycloalkyl; aryl that can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —CF$_3$, —OCF$_3$, hydroxy, alkoxy-carbonyl, and carboxyl; benzothienyl; thiazolyl; or thienyl;
R$^3$ represents cycloalkyl; formyl; acetyl; ethoxy-carbonyl; hydroxy-ethyl; benzo[1,3]dioxolyl; indolyl; pyridyl that can be mono-, di-, or tri-substituted, wherein the substituents are independently selected from: halogen, alkyl, alkoxy, alkoxy-alkoxy, —CF$_3$, —OCF$_3$, hydroxy, alkoxy-carbonyl, carboxyl, hydroxy-C$_{1-5}$-alkyl, 2,3-dihydroxypropyl, di-(hydroxy-C$_{1-5}$-alkyl)-C$_{1-5}$-alkyl, —CH$_2$—(CH$_2$)$_k$—NR$^{31}$R$^{32}$, (azetidine-3-carboxylic acid)-1-yl-methyl, (azetidine-3-carboxylic acid C$_{1-5}$-alkylester)-1-yl-methyl, 2-[(azetidine-3-carboxylic acid)-1-yl]-ethyl, 2-[(azetidine-3-carboxylic acid C$_{1-5}$-alkylester)-1-yl]-ethyl, 3-[(azetidine-3-carboxylic acid)-1-yl]-propyl, 3-[(azetidine-3-carboxylic acid C$_{1-5}$-alkylester)-1-yl]-propyl, (pyrrolidine-3-carboxylic acid)-1-yl-methyl, (pyrrolidine-3-carboxylic acid C$_{1-5}$-alkylester)-1-yl-methyl, (pyrrolidine-2-carboxylic acid)-1-yl-methyl, (pyrrolidine-2-carboxylic acid C$_{1-5}$-alkylester)-1-yl-methyl, 2-[(pyrrolidine-3-carboxylic acid)-1-yl]-ethyl, 2-[(pyrrolidine-3-carboxylic acid C$_{1-5}$-alkylester)-1-yl]-ethyl, 2-[(pyrrolidine-2-carboxylic acid)-1-yl]-ethyl, 2-[(pyrrolidine-2-carboxylic acid C$_{1-5}$-alkylester)-1-yl]-ethyl, 3-[(pyrrolidine-3-carboxylic acid)-1-yl]-propyl, 3-[(pyrrolidine-3-carboxylic acid C$_{1-5}$-alkylester)-1-yl]propyl, 3-[(pyrrolidine-2-carboxylic acid)-1-yl]-propyl, 3-[(pyrrolidine-2-carboxylic acid C$_{1-5}$-alkylester)-1-yl]-propyl, —CH$_2$—(CH$_2$)$_p$—CONR$^{31}$R$^{32}$, —CO—NHR$^{31}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —(CH$_2$)$_p$CH(OH)—CH$_2$—NR$^{31}$R$^{32}$, hydroxy-C$_{2-5}$-alkoxy, di-(hydroxy-C$_{1-5}$-alkyl)-C$_{1-5}$-alkoxy, 2,3-dihydroxypropoxy, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(C$_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-(C$_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid C$_{1-5}$-alkylester)-1-yl]-ethoxy, 2-[(pyrrolidine-3-carboxylic acid)-1-yl]-ethoxy, 2-[(pyrrolidine-3-carboxylic acid C$_{1-5}$-alkylester)-1-yl]-ethoxy, 2-[(pyrrolidine-2-carboxylic acid)-1-yl]-ethoxy, 2-[(pyrrolidine-2-carboxylic acid C$_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid C$_{1-5}$-alkylester)-1-yl]-propoxy, 3-[(pyrrolidine-3-carboxylic acid)-1-yl]-propoxy, 3-[(pyrrolidine-3-carboxylic acid C$_{1-5}$-alkylester)-1-yl]-propoxy, 3-[(pyrrolidine-2-carboxylic acid)-1-yl]-propoxy, 3-[(pyrrolidine-2-carboxylic acid C$_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—C$_{1-12}$—CONR$^{31}$R$^{32}$, 1-(3-carboxy-azetidinyl)-1-oxo-2-ethoxy, 1-(pyrrolidine-2-carboxylic acid)-1-yl-1-oxo-2-ethoxy, 1-(pyrrolidine-3-carboxylic acid)-1-yl -1-oxo-2-ethoxy, 3-carbamoyl-propoxy, 3-(C$_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid C$_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid C$_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid C$_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(C$_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_p$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_p$CH(OH)—CH$_2$—NHCOR$^{34}$, —OCH$_2$—(CH$_2$)$_m$—NHCOR$^{34}$, —OCH$_2$—CH(OH)—CH$_2$—NHCOR$^{34}$, —SO$_2$NHR$^{31}$, morpholino, piperidino, oxo-piperidinyl, oxo-pyrrolidinyl, pyridyl, and phenyl wherein the phenyl-ring can again be mono-, di-, tri-, or tetra-substituted wherein the substituents are independently selected from halogen, alkyl, alkoxy, cyano, —CF$_3$, hydroxy, alkoxy-carbonyl, and carboxyl; furanyl that can be mono- or di-substituted, wherein the substituents are independently selected from methyl, hydroxy-methyl, bromine, and phenyl wherein the phenyl-ring can again be mono-, di-, or tri-substituted wherein the substituents are independently selected from halogen, alkyl, alkoxy, cyano, —CF$_3$, —OCF$_3$, hydroxy, alkoxy-carbonyl, alkyl-carbonyl, carboxyl, and methylene-dioxy; thienyl that can be mono-substituted with methyl, chlorine, or phenyl wherein the phenyl-ring can again be mono-, di-, or tri-substituted wherein the substituents are independently selected from halogen, alkyl, alkoxy, cyano, —CF$_3$, —OCF$_3$, hydroxy, alkoxy-carbonyl, alkyl-carbonyl, carboxyl, and methylene-dioxy; pyrimidinyl that can be mono-substituted with alkyl, halogen, cyclopropyl, CH$_3$—S—, methylsulfonyl, or phenyl wherein the phenyl-ring can again be mono-, di-, or tri-substituted wherein the substituents are independently selected from halogen, alkyl, alkoxy, cyano, —CF$_3$, and —OCF$_3$; pyrimidinyl mono- or di-substituted with methoxy; pyridazinyl; benzothienyl; benzofuranyl; quinolinyl; isoquinolinyl; or benzhydryl, wherein both phenyl rings can be mono- or di-substituted, wherein the substituents are independently selected from halogen, alkyl, alkoxy, —CF$_3$, —OCF$_3$, hydroxy, cyano, alkoxy-carbonyl, and alkyl-carbonyl; or R$^3$ represents a mono-, di-, tri-, or tetra-substituted aryl, wherein the substituents are independently selected from the group consisting of:

hydroxy-C$_{1-5}$-alkyl; 2,3-dihydroxypropyl; di-(hydroxy-C$_{1-5}$-alkyl)-C$_{1-5}$-alkyl; —CH$_2$—(CH$_2$)$_k$—NR$^{31}$R$^{32}$; (azetidine-3-carboxylic acid)-1-yl-methyl; (azetidine-3-carboxylic acid C$_{1-5}$-alkylester)-1-yl-methyl; 2-[(azetidine-3-carboxylic acid)-1-yl]-ethyl; 2-[(azetidine-3-carboxylic acid C$_{1-5}$-alkylester)-1-yl]-ethyl; 3-[(azetidine-3-carboxylic acid)-1-yl]-propyl; 3-[(azetidine-3-carboxylic acid C$_{1-5}$-alkylester)-1-yl]-propyl; (pyrrolidine-3-carboxylic acid)-1-yl-methyl; (pyrrolidine-3-carboxylic acid C$_{1-5}$-alkylester)-1-yl-methyl; (pyrrolidine-2-carboxylic acid)-1-yl-methyl; (pyrrolidine-2-carboxylic acid C$_{1-5}$-alkylester)-1-yl-methyl; 2-[(pyrrolidine-3-carboxylic acid)-1-yl]-ethyl; 2-[(pyrrolidine-3-carboxylic acid C$_{1-5}$-alkylester)-1-yl]-ethyl; 2-[(pyrrolidine-2-carboxylic acid)-1-yl]-ethyl; 2-[(pyrrolidine-2-carboxylic acid C$_{1-5}$-alkylester)-1-yl]-ethyl; 3-[(pyrrolidine-3-carboxylic acid)-1-yl]-propyl; 3-[(pyrrolidine-3-carboxylic acid C$_{1-5}$-alkylester)-1-yl]-propyl; 3-[(pyrrolidine-2-carboxylic acid)-1-yl]- propyl; 3-[(pyrrolidine-2-carboxylic acid $C_{1-5}$-alkylester)-1-yl]propyl; —$CH_2$—$(C_{1-12})_p$—$CONR^{31}R^{32}$; —CO—$NHR^{31}$; 1-(3-carboxy-azetidinyl)-2-acetyl; 1-(2-carboxy-pyrrolidinyl)-2-acetyl; 1-(3-carboxy-pyrrolidinyl)-2-acetyl; 1-(3-carboxy-azetidinyl)-3-propionyl; 1-(2-carboxy-pyrrolidinyl)-3-propionyl; 1-(3-carboxy-pyrrolidinyl)-3-propionyl; —$(CH_2)_p$CH(OH)—$CH_2$—$NR^{31}R^{32}$; hydroxy-$C_{2-5}$-alkoxy; di-(hydroxy-$C_{1-5}$-alkyl)-$C_{1-5}$-alkoxy; 2,3-dihydroxypropoxy; 2-hydroxy-3-methoxy-propoxy; —$OCH_2$—$(CH_2)_m$—$NR^{31}R^{32}$; 2-pyrrolidin-1-yl-ethoxy; 3-pyrrolidin-1-yl-propoxy; 2-piperazin-1-yl-ethoxy; 2-[4-($C_{1-5}$-alkyl)-piperazin-1-yl]-ethoxy; 2-[4-(2-hydroxy-ethyl)-piperazin-1-yl]-ethoxy; 3-piperazin-1-yl-propoxy; 3-[4-($C_{1-5}$-alkyl)-piperazin-1-yl]-propoxy; 3-[4-(2-hydroxy-ethyl)-piperazin-1-yl]-propoxy; 2-morpholin-4-yl-ethoxy; 3-morpholin-4-yl-propoxy; 2-[(azetidine-3-carboxylic acid)-1-yl]-ethoxy; 2-[(azetidine-3-carboxylic acid $C_{1-5}$-alkylester)-1-yl]-ethoxy; 2-[(pyrrolidine-3-carboxylic acid)-1-yl]-ethoxy; 2-[(pyrrolidine-3-carboxylic acid $C_{1-5}$-alkylester)-1-yl]-ethoxy; 2-[(pyrrolidine-2-carboxylic acid)-1-yl]ethoxy; 2-[(pyrrolidine-2-carboxylic acid $C_{1-5}$-alkylester)-1-yl]-ethoxy; 2-[(2-hydroxy-pyrrolidine)-1-yl]-ethoxy; 2-[(3-hydroxy-pyrrolidine)-1-yl]-ethoxy; 3-[(azetidine-3-carboxylic acid)-1-yl]-propoxy; 3-[(azetidine-3-carboxylic acid $C_{1-5}$-alkylester)-1-yl]-propoxy; 3-[(pyrrolidine-3-carboxylic acid)-1-yl]-propoxy; 3-[(pyrrolidine-3-carboxylic acid $C_{1-5}$-alkylester)-1-yl]-propoxy; 3-[(pyrrolidine-2-carboxylic acid)-1-yl]-Propoxy; 3-[(pyrrolidine-2-carboxylic acid $C_{1-5}$-alkylester)-1-yl]-propoxy; 3-[(2-hydroxy-pyrrolidine)-1-yl]-propoxy; 3-[(3-hydroxy-pyrrolidine)-1-yl]-propoxy; 2-amino-3-hydroxy-2-hydroxymethyl-propoxy; —O—$CH_2$—$CONR^{31}R^{32}$; 1-(3-carboxy-azetidinyl)-1-oxo-2-ethoxy; 1-(pyrrolidine-2-carboxylic acid)-1-yl-1-oxo-2-ethoxy; 1-(pyrrolidine-3-carboxylic acid)-1-yl-1-oxo-2-ethoxy; 3-carbamoyl-propoxy; 3-($C_{1-5}$-alkylcarbamoyl)propoxy; 3-(2-hydroxyethylcarbamoyl)propoxy; —$OCH_2$—CH(OH)—$CH_2$—$NR^{31}R^{32}$; 3-[(azetidine-3-carboxylic acid)-1-yl]-2-hydroxypropoxy; 3-[(azetidine-3-carboxylic acid $C_{1-5}$-alkylester)-1-yl]-2-hydroxypropoxy; 2-hydroxy-3-[(pyrrolidine-3-carboxylic acid)-1-yl]-propoxy; 2-hydroxy-3-[(pyrrolidine-3-carboxylic acid $C_{1-5}$-alkylester)-1-yl]propoxy; 2-hydroxy-3-[(pyrrolidine-2-carboxylic acid)-1-yl]-propoxy; 2-hydroxy-3-[(pyrrolidine-2-carboxylic acid $C_{1-5}$-alkylester)-1-yl]-propoxy; 2-hydroxy-3-[(2-hydroxy-pyrrolidine)-1-yl]-propoxy; 2-hydroxy-3-[(3-hydroxy-pyrrolidine)-1-yl]-propoxy; 2-hydroxy-3-pyrrolidin-1-yl-propoxy; 2-hydroxy-3-piperazin-1-yl-propoxy; 2-hydroxy-3-[4-($C_{1-5}$-alkyl)-piperazin-1-yl]-propoxy; 2-hydroxy-3-[4-(2-hydroxy-ethyl)-piperazin-1-yl]-propoxy; 2-hydroxy-3-morpholin-4-yl-propoxy; —$NR^{31}R^{32}$; —NHCO—$R^{31}$; —$CH_2$—$(CH_2)_k$—$NHSO_2R^{33}$; —$(CH_2)_p$CH(OH)—$CH_2$—$NHSO_2R^{33}$; —$OCH_2$—$(CH_2)_m$—$NHSO_2R^{33}$; —$OCH_2$—CH(OH)—$CH_2$—$NHSO_2R^{33}$; —$CH_2$—$(CH_2)_k$—$NHCOR^{34}$; —$(CH_2)_p$CH(OH)—$CH_2$—$NHCOR^{34}$; —$OCH_2$—$(CH_2)_m$—$NHCOR^{34}$; —$OCH_2$—CH(OH)—$CH_2$—$NHCOR^{34}$; —$SO_2NHR^{31}$; phenyl, wherein said phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; pyridyl, wherein said pyridyl ring can further be mono- or di-substituted, wherein the substituents are independently selected from alkyl, alkoxy, halogen, hydroxy, and —$CF_3$; furanyl, wherein said furanyl ring can further be mono- or di-substituted, wherein the substituents are independently selected from alkyl, alkoxy, and halogen; thienyl, wherein said thienyl ring can further be mono- or di-substituted, wherein the substituents are independently selected from alkyl, alkoxy, and halogen; oxadiazolyl, wherein said oxadiazolyl ring can further be mono-substituted with alkyl, pyridyl or phenyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; isoxazolyl, wherein said isoxazolyl ring can further be mono- or di-substituted, wherein the substituents are independently selected from alkyl, phenyl and pyridyl; halogen; alkyl; alkoxy; —$CF_3$; —$OCF_3$; hydroxy; cyano; alkoxy-carbonyl; alkyl-carbonyl; carboxyl; monoalkyl-amino; dialkyl-amino; pyrrolidino; morpholino; thiomorpholino; piperidino; N-benzyl-N-alkyl-amino; N-pyridyl-N-methyl-amino; (dialkyl-amino)-alkoxy; phenyl-alkoxy, wherein the phenyl ring can further be mono-, di-, or tri-substituted, wherein the substituents are independently selected from halogen, alkyl, alkoxy, —$CF_3$, hydroxy, cyano, alkoxy-carbonyl, alkyl-carbonyl, carboxyl, and methylene-dioxy; phenyl-amino-carbonyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; phenyl-alkyl-amino-carbonyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; alkyl-amino-carbonyl; dialkyl-amino-carbonyl; pyridyl-amino-carbonyl; phenyl-carbonyl-amino, wherein the phenyl ring can further be mono-, di-, or tri-substituted, wherein the substituents are independently selected from halogen, alkyl, alkoxy, —$CF_3$, hydroxy, cyano, alkoxy-carbonyl, alkyl-carbonyl, carboxyl, and methylene-dioxy; phenyl-alkyl-carbonyl-amino, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; alkyl-carbonyl-amino; pyridyl-carbonyl-amino; and tetrahydro-isoquinolinyl;

or $R^3$ represents the following group:

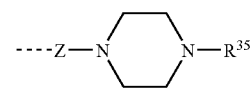

wherein Z represents phenyl or pyridyl;

$R^{31}$ represents hydrogen, methyl, ethyl, 1-propyl, 2-propyl, 2-hydroxyethyl, 2-hydroxy-1-hydroxymethyl-ethyl, 2,3-dihydroxypropyl, 2-$C_{1-5}$-alkoxyethyl, 3-hydroxypropyl, 3-$C_{1-5}$-alkoxypropyl, 2-aminoethyl, 2-($C_{1-5}$-alkylamino)ethyl, 2-(di-($C_{1-5}$-alkyl)amino)ethyl, carboxymethyl, 1-($C_{1-5}$-alkylcarboxy)methyl, 2-carboxyethyl, 2-($C_{1-5}$-alkylcarboxy)ethyl, phenyl, pyridyl, phenyl-alkyl, hydroxyalkyl-carbonyl, alkyl-carbonyl, cycloalkyl-carbonyl, or phenyl-carbonyl;

$R^{32}$ represents hydrogen, methyl, or ethyl;

$R^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

$R^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

p represents 0, 1, or 2;

$R^{35}$ represents alkyl; alkyl-carbonyl; alkoxy-carbonyl; cycloalkyl-carbonyl; aryl, wherein the aryl-ring can be mono-, di-, tri-, or tetra-substituted wherein the substituents are independently selected from halogen, alkyl, alkoxy, —$CF_3$, —$OCF_3$, hydroxy, alkoxy-carbonyl, and carboxyl; aryl-carbonyl, wherein the aryl-ring can be mono-, di-, tri-, or tetra-substituted wherein the substituents are independently selected from halogen, alkyl, alkoxy, —$CF_3$, —$OCF_3$, hydroxy, alkoxy-carbonyl, and carboxyl; aryl-alkyl, wherein the aryl-ring can be mono-, di-, tri-, or tetra-substituted wherein the substituents are independently selected from halogen, alkyl, alkoxy, —$CF_3$, —$OCF_3$, hydroxy, alkoxy-carbonyl, and carboxyl; pyridyl, wherein the pyridyl-ring can be mono-, di-, or tri-substituted wherein the substituents are independently selected from halogen, alkyl, alkoxy, —$CF_3$, —$OCF_3$, hydroxy, alkoxy-carbonyl, and carboxyl; pyridyl-alkyl, wherein the pyridyl-ring can be mono-, di-, or tri-substituted wherein the substituents are independently selected from halogen, alkyl, alkoxy, —$CF_3$, —$OCF_3$, hydroxy, alkoxy-carbonyl, and carboxyl; pyrimidinyl, wherein the pyrimidinyl-ring can be mono-, or di-substituted wherein the substituents are independently selected from halogen, alkyl, alkoxy, and —$CF_3$; furanyl-carbonyl; furanyl-alkyl, wherein the furanyl-ring can be mono-, or di-substituted wherein the substituents are independently selected from methyl, hydroxy-methyl, and bromine; thienyl-alkyl that can be mono-substituted with methyl or chlorine; benzothienyl-alkyl; benzofuranyl-alkyl; imidazolyl-alkyl; or thiazolyl-alkyl; and $R^4$ represents alkyl; cycloalkyl; benzo[1,3]dioxolyl; benzo[1,3]dioxolyl —$CH_2$—; benzothienyl; benzofuranyl; indazolyl; indolyl that can be mono- or di-substituted, wherein the substituents are independently selected from halogen, alkyl, alkoxy, —$CF_3$, —$OCF_3$, and hydroxy; quinolinyl; isoquinolinyl; benzhydryl, wherein both phenyl-rings can be mono- or di-substituted, wherein the substituents are independently selected from halogen, alkyl, alkoxy, —$CF_3$, —$OCF_3$, hydroxy, cyano, alkoxy-carbonyl, and alkyl-carbonyl; aryl that can be mono-, di-, tri-, or tetra-substituted, wherein the substituents are independently selected from phenyl, halogen, alkyl, alkoxy, —$CF_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —$CF_3$, —$OCF_3$, hydroxy, alkoxy-carbonyl, and carboxyl; aryl —CH=CH—, wherein aryl can be mono-, di-, tri-, or tetra-substituted, wherein the substituents are independently selected from phenyl, halogen, alkyl, alkoxy, —$CF_3$, hydroxy, cyano, alkoxy-carbonyl, alkyl-carbonyl, and carboxyl; aryl —$CH_2$— $CH_2$—, wherein aryl can be mono-, di-, tri-, or tetra-substituted, wherein the substituents are independently selected from phenyl, halogen, alkyl, alkoxy, —$CF_3$, hydroxy, cyano, alkoxy-carbonyl, alkyl-carbonyl, and carboxyl; pyridyl —CH=CH—, wherein pyridyl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl —$CH_2$—$CH_2$—, wherein pyridyl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; aryl —$CH_2$—, wherein aryl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl —$CH_2$—, wherein pyridyl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; thienyl —$CH_2$—; pyrimidinyl-CH=CH—; furanyl —CH=CH—; or thienyl —CH=CH—;

in free or an optically pure enantiomer, a mixture of enantiomers, a racemate, optically pure diastereomer, mixture of diastereomers, diastereomeric racemate, mixture of diastereomeric racemates, or a meso-form, as well as a salt form.

2. A compound according to claim 1, which has the formula I':

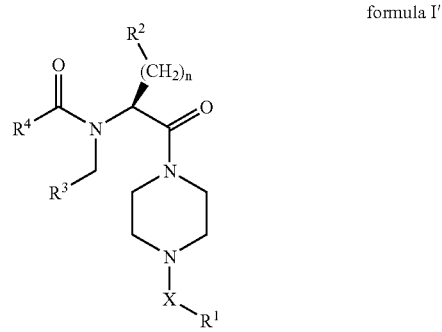

formula I' wherein n, X, $R^1$, $R^2$, $R^3$ and $R^4$ are as defined in claim 1.

3. A compound according to claim 1, wherein

X represents —$(CH_2)_{0-2}$— or —C(=O)—;

n represents the integer 0, 1 or 2;

$R^1$ represents hydrogen; alkyl; cycloalkyl; ethoxy-carbonyl; hydroxy-ethyl; benzo[1,3]dioxolyl; aryl that can be mono-, di-, tri-, or tetra-substituted, wherein the substituents are independently selected from halogen, alkyl, alkoxy, —$CF_3$, —$OCF_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —$CF_3$, —$OCF_3$, hydroxy, alkoxy-carbonyl, and carboxyl; furanyl that can be mono-, or di-substituted, wherein the substituents are independently selected from methyl, hydroxy-methyl, and bromine; thienyl that can be mono-substituted with methyl or chlorine; pyrimidinyl that can be mono-substituted with alkyl, halogen, cyclopropyl, $CH_3$—S—, or methylsulfonyl or that can be mono- or di-substituted with methoxy; pyridazinyl; benzothienyl; benzofuranyl; quinolinyl; isoquinolinyl; or benzhydryl, wherein both phenyl rings can be mono- or di-substituted, wherein the substituents are independently selected from halogen, alkyl, alkoxy, —$CF_3$, —$OCF_3$, hydroxy, cyano, alkoxy-carbonyl, and alkyl-carbonyl;

$R^2$ represents hydrogen; alkyl; indolyl; carboxyl; alkoxy-carbonyl; amino-carbonyl; imidazolyl; cycloalkyl; aryl that can be mono-, di-, tri, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —$CF_3$, —$OCF_3$, hydroxy, alkoxy-carbonyl, and carboxyl; benzothienyl; thiazolyl; or thienyl;

$R^3$ represents cycloalkyl; formyl; acetyl; ethoxy-carbonyl; hydroxy-ethyl; benzo[1,3]dioxolyl; pyridyl that can be mono-, di-, or tri-substituted, wherein the substituents are independently selected from phenyl, halogen, alkyl, alkoxy, —$CF_3$, —$OCF_3$, hydroxy, alkoxy-carbonyl, and carboxyl; furanyl that can be mono- or di-substituted, wherein the substituents are independently selected from phenyl, methyl, hydroxy-methyl, and bromine; thienyl that can be mono-substituted with phenyl, methyl, or chlorine; pyrimidinyl that can be mono-substituted with phenyl, alkyl, halogen, cyclopropyl, $CH_3$—S—, or methylsulfonyl or that can be mono- or di-substituted with methoxy; pyridazinyl; benzothienyl; benzofuranyl; quinolinyl; isoquinolinyl; or benzhydryl, wherein both phenyl rings can be mono- or di-substituted, wherein the substituents are independently selected from halogen, alkyl, alkoxy, —$CF_3$, —$OCF_3$, hydroxy, cyano, alkoxy-carbonyl, and alkyl-carbonyl; or $R^3$ represents a mono-, di-, tri-, or tetra-substituted aryl, wherein the substituents are independently selected from the group consisting of:

phenyl, wherein said phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; pyridyl, wherein said pyridyl ring can further be mono- or di-substituted, wherein the substituents are independently selected from alkyl, alkoxy, halogen, hydroxy, and —$CF_3$; furanyl, wherein said furanyl ring can further be mono- or di-substituted, wherein the substituents are independently selected from alkyl, alkoxy, and halogen; thienyl, wherein said thienyl ring can further be mono- or di-substituted, wherein the substituents are independently selected from alkyl, alkoxy, and halogen; oxadiazolyl, wherein said oxadiazolyl ring can further be mono-substituted with alkyl or phenyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; isoxazolyl, wherein said isoxazolyl ring can further be mono- or di-substituted, wherein the substituents are independently selected from alkyl, phenyl and pyridyl; halogen; alkyl; alkoxy; —$CF_3$; —$OCF_3$; hydroxy; cyano; alkoxy-carbonyl; alkyl-carbonyl; carboxyl; monoalkyl-amino; dialkyl-amino; pyrrolidino; morpholino; thiomorpholino; piperidino; N-benzyl-N-alkyl-amino; N-pyridyl-N-methyl-amino; (dialkyl-amino)-alkoxy; phenyl-alkoxy, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; phenyl-amino-carbonyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; phenyl-alkyl-amino-carbonyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; alkyl-amino-carbonyl; dialkyl-amino-carbonyl; pyridyl-amino-carbonyl; phenyl-carbonyl-amino, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; phenyl-alkyl-carbonyl-amino, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; alkyl-carbonyl-amino; and pyridyl-carbonyl-amino; and $R^4$ represents alkyl; cycloalkyl; benzo[1,3]dioxolyl; benzo[1,3]dioxolyl —$CH_2$—; benzothienyl; benzofuranyl; indazolyl; indolyl that can be mono- or di-substituted, wherein the substituents are independently selected from halogen, alkyl, alkoxy, —$CF_3$, —$OCF_3$, and hydroxy; quinolinyl; isoquinolinyl; benzhydryl, wherein both phenyl-rings can be mono- or di-substituted, wherein the substituents are independently selected from halogen, alkyl, alkoxy, —$CF_3$, —$OCF_3$, hydroxy, cyano, alkoxy-carbonyl, and alkyl-carbonyl; aryl that can be mono-, di-, tri-, or tetra-substituted, wherein the substituents are independently selected from phenyl, halogen, alkyl, alkoxy, —$CF_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —$CF_3$, —$OCF_3$, hydroxy, alkoxy-carbonyl, and carboxyl; aryl —CH═CH—, wherein aryl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; aryl —$CH_2$—$CH_2$—, wherein aryl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl —CH═CH—, wherein pyridyl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; pyridyl —$CH_2$—$CH_2$—, wherein pyridyl can be mono-, di-, tri-, or tetra-substituted, wherein the substituents are independently selected from phenyl, halogen, alkyl, alkoxy, —$CF_3$, —$OCF_3$, hydroxy, cyano, alkoxy-carbonyl, alkyl-carbonyl, and carboxyl; aryl —$CH_2$—, wherein aryl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl —CH$_2$—, wherein pyridyl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; or thienyl —CH$_2$—.

4. A compound according to claim 1, wherein

X represents —CH$_2$—;

n represents the integer 1;

R$^1$ represents aryl that can be mono-, di-, tri-, or tetra-substituted, wherein the substituents are independently selected from halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —CF$_3$, —OCF$_3$, hydroxy, alkoxy-carbonyl, and carboxyl; furanyl that can be mono- or di-substituted, wherein the substituents are independently selected from methyl, hydroxy-methyl, and bromine; thienyl that can be mono-substituted with methyl or chlorine; benzothienyl; benzofuranyl; quinolinyl; or isoquinolinyl; and R$^2$ represents aryl that can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —CF$_3$, hydroxy, alkoxy-carbonyl, and carboxyl; benzothienyl; thiazolyl; or thienyl.

5. A compound according to claim 4, wherein R$^1$ and R$^2$ both represent phenyl.

6. A compound according to claim 5, wherein R$^4$ represents a radical of the formula

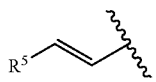

wherein R$^5$ represents phenyl that can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl.

7. A compound according to claim 1, wherein

X represents —(CH$_2$)$_{0-1}$— or —C(═O)—;

n represents the integer 1;

R$^1$ represents hydrogen; alkyl; ethoxy-carbonyl; hydroxy-ethyl; benzo[1,3]dioxolyl; aryl that can be mono-substituted with halogen, alkyl, alkoxy, —CF$_3$, or alkyl-carbonyl; pyridyl that can be mono-substituted with halogen, alkyl, alkoxy, or —CF$_3$; furanyl that can be mono- or di-substituted, wherein the substituents are independently selected from methyl, hydroxy-methyl, and bromine; thienyl that can be mono-substituted with methyl or chlorine; pyrimidinyl; isoquinolinyl; or benzhydryl;

R$^2$ represents indolyl; imidazolyl; aryl that can be mono- or di-substituted, wherein the substituents are independently selected from halogen, alkyl, hydroxy, and cyano; pyridyl; benzothienyl; thiazolyl; or thienyl;

R$^3$ represents aryl that is mono-substituted with phenyl, pyridyl, alkyl, alkoxy, pyrrolidino, (dialkyl-amino)-alkoxy or phenyl-alkoxy; and R$^4$ represents aryl —CH═CH—, wherein aryl is mono-substituted with alkoxy or —CF$_3$; or aryl —CH$_2$—CH$_2$—, wherein aryl is di-substituted with —CF$_3$.

8. A compound according to claim 1, wherein

X represents —(CH$_2$)—;

n represents the integer 1;

R$^1$ represents hydrogen; methyl; cycloalkyl; benzo[1,3]dioxolyl; aryl that can be mono-, di-, tri-, or tetra-substituted, wherein the substituents are independently selected from halogen, alkyl, alkoxy, —CF$_3$, —OCF$_3$, hydroxy, cyano, alkoxy-carbonyl, alkyl-carbonyl, and carboxyl; pyridyl that can be mono-, or di-substituted, wherein the substituents are independently selected from halogen, alkyl, alkoxy, —CF$_3$, —OCF$_3$, hydroxy, alkoxy-carbonyl, and carboxyl; furanyl that can be mono-, or di-substituted, wherein the substituents are independently selected from methyl, hydroxy-methyl, and bromine; thienyl that can be mono-substituted with methyl or chlorine; pyrimidinyl that can be mono-substituted with alkyl, halogen, or cyclopropyl or that can be mono- or di-substituted with methoxy; pyridazinyl; benzothienyl; benzofuranyl; quinolinyl; isoquinolinyl; imidazolyl; thiazolyl; or oxazolyl;

R$^2$ represents cycloalkyl; aryl that can be mono-, di-, or tri-substituted, wherein the substituents are independently selected from halogen, alkyl, alkoxy, —CF$_3$, and cyano; pyridyl that can be mono-, or di-substituted, wherein the substituents are independently selected from halogen, alkyl, alkoxy, —CF$_3$, and —OCF$_3$; thiazolyl; or thienyl;

R$^3$ represents cycloalkyl; pyridyl that can be mono-, di-, or tri-substituted, wherein the substituents are independently selected from: halogen, alkyl, alkoxy, —CF$_3$, —OCF$_3$, alkoxy-carbonyl, carboxyl, hydroxy-C$_{1-5}$-alkyl, 2,3-dihydroxypropyl, di-(hydroxy-C$_{1-5}$-alkyl)-C$_{1-5}$-alkyl, —CH$_2$—(CH$_2$)$_k$—NR$^{31}$R$^{32}$, (azetidine-3-carboxylic acid)-1-yl-methyl, (azetidine-3-carboxylic acid C$_{1-5}$-alkylester)-1-yl-methyl, 2-[(azetidine-3-carboxylic acid)-1-yl]-ethyl, 2-[(azetidine-3-carboxylic acid C$_{1-5}$-alkylester)-1-yl]-ethyl, 3-[(azetidine-3-carboxylic acid)-1-yl]-propyl, 3-[(azetidine-3-carboxylic acid C$_{1-5}$-alkylester)-1-yl]-propyl, (pyrrolidine-3-carboxylic acid)-1-yl-methyl, (pyrrolidine-3-carboxylic acid C$_{1-5}$-alkylester)-1-yl-methyl, (pyrrolidine-2-carboxylic acid)-1-yl-methyl, (pyrrolidine-2-carboxylic acid C$_{1-5}$-alkylester)-1-yl-methyl, 2-[(pyrrolidine-3-carboxylic acid)-1-yl]-ethyl, 2-[(pyrrolidine-3-carboxylic acid C$_{1-5}$-alkylester)-1-yl]ethyl, 2-[(pyrrolidine-2-carboxylic acid)-1-yl]-ethyl, 2-[(pyrrolidine-2-carboxylic acid C$_{1-5}$-alkylester)-1-yl]-ethyl, 3-[(pyrrolidine-3-carboxylic acid)-1-yl]-propyl, 3-[(pyrrolidine-3-carboxylic acid C$_{1-5}$-alkylester)-1-yl]-propyl, 3-[(pyrrolidine-2-carboxylic acid)-1-yl]-propyl, 3-[(pyrrolidine-2-carboxylic acid C$_{1-5}$-alkylester)-1-yl]-propyl, —CH$_2$—(CH$_2$)$_p$—CONR$^{31}$R$^{32}$, —CO—NHR$^{31}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —(CH$_2$)$_p$CH(OH)—CH$_2$—NR$^{31}$R$^{32}$, hydroxy-C$_{2-5}$-alkoxy, di-(hydroxy-C$_{1-5}$-alkyl)-C$_{1-5}$-alkoxy, 2,3-dihydroxypropoxy, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-ylpropoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl] ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 1-(3-carboxy-azetidinyl)-1-oxo-2-ethoxy, 1-(pyrrolidine-2-carboxylic acid)-1-yl-1-oxo-2-ethoxy, 1-(pyrrolidine-3-carboxylic acid)-1-yl-1-oxo-2-ethoxy, 3-carbamoyl-propoxy, 3-($C_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_p$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_p$CH(OH)—CH$_2$—NHCOR$^{34}$, —OCH$_2$—(CH$_2$)$_m$—NHCOR$^{34}$, —OCH$_2$—CH(OH)—CH$_2$—NHCOR$^{34}$, —SO$_2$NHR$^{31}$, and phenyl wherein the phenyl-ring can again be mono-, di-, tri-, or tetra-substituted wherein the substituents are independently selected from halogen, alkyl, alkoxy, —CF$_3$, —OCF$_3$, hydroxy, alkoxy-carbonyl, and carboxyl; furanyl that can be mono- or di-substituted, wherein the substituents are independently selected from methyl, hydroxy-methyl, bromine, and phenyl, wherein said phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; thienyl that can be mono-substituted with methyl, chlorine, or phenyl wherein said phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; benzothienyl; benzofuranyl; quinolinyl; or isoquinolinyl; or R$^3$ represents a mono-, di-, tri-, or tetra-substituted aryl, wherein the substituents are independently selected from the group consisting of:

hydroxy-$C_{1-5}$-alkyl; 2,3-dihydroxypropyl; di-(hydroxy-$C_{1-5}$-alkyl)-$C_{1-5}$-alkyl; —CH$_2$—(CH$_2$)$_k$—NR$^{31}$R$^{32}$; (azetidine-3-carboxylic acid)-1-yl-methyl; (azetidine-3-carboxylic acid $C_{1-5}$-alkylester)-1-yl-methyl; 2-[(azetidine-3-carboxylic acid)-1-yl]-ethyl; 2-[(azetidine-3-carboxylic acid $C_{1-5}$-alkylester)-1-yl]-ethyl; 3-[(azetidine-3-carboxylic acid)-1-yl]-propyl; 3-[(azetidine-3-carboxylic acid $C_{1-5}$-alkylester)-1-yl]-propyl; (pyrrolidine-3-carboxylic acid)-1-yl-methyl; (pyrrolidine-3-carboxylic acid $C_{1-5}$-alkylester)-1-yl-methyl; (pyrrolidine-2-carboxylic acid)-1-yl-methyl; (pyrrolidine-2-carboxylic acid $C_{1-5}$-alkylester)-1-yl-methyl; 2-[(pyrrolidine-3-carboxylic acid)-1-yl]-ethyl; 2-[(pyrrolidine-3-carboxylic acid $C_{1-5}$-alkylester)-1-yl]ethyl; 2-[(pyrrolidine-2-carboxylic acid)-1-yl]-ethyl; 2-[(pyrrolidine-2-carboxylic acid $C_{1-5}$-alkylester)-1-yl]-ethyl; 3-[(pyrrolidine-3-carboxylic acid)-1-yl]-propyl; 3-[(pyrrolidine-3-carboxylic acid $C_{1-5}$-alkylester)-1-yl]-propyl; 3-[(pyrrolidine-2-carboxylic acid)-1-yl]-propyl; 3-[(pyrrolidine-2-carboxylic acid $C_{1-5}$-alkylester)-1-yl]-propyl; —CH$_2$—(CH$_2$)$_p$—CONR$^{31}$R$^{32}$; —CO—NHR$^{31}$; 1-(3-carboxy-azetidinyl)-2-acetyl; 1-(2-carboxy-pyrrolidinyl)-2-acetyl; 1-(3-carboxy-pyrrolidinyl)-2-acetyl; 1-(3-carboxy-azetidinyl)-3-propionyl; 1-(2-carboxy-pyrrolidinyl)-3-propionyl; 1-(3-carboxy-pyrrolidinyl)-3-propionyl; —(CH$_2$)$_p$CH(OH)—CH$_2$—NR$^{31}$R$^{32}$; hydroxy-$C_{2-5}$-alkoxy; di-(hydroxy-$C_{1-5}$-alkyl)-$C_{1-5}$-alkoxy; 2,3-dihydroxypropoxy; 2-hydroxy-3-methoxy-propoxy; —OCH$_2$—(CH$_2$)$_m$—NR$^{31}$R$^{32}$; 2-pyrrolidin-1-yl-ethoxy; 3-pyrrolidin-1-yl-propoxy; 2-piperazin-1-yl-ethoxy; 2-[4-($C_{1-5}$-alkyl)-piperazin-1-yl]-ethoxy; 2-[4-(2-hydroxy-ethyl)-piperazin-1-yl]-ethoxy; 3-piperazin-1-yl-propoxy; 3-[4-($C_{1-5}$-alkyl)-piperazin-1-yl]-propoxy; 3-[4-(2-hydroxy-ethyl)-piperazin-1-yl]-propoxy; 2-morpholin-4-yl-ethoxy; 3-morpholin-4-yl-propoxy; 2-[(azetidine-3-carboxylic acid)-1-yl]-ethoxy; 2-[(azetidine-3-carboxylic acid $C_{1-5}$-alkylester)-1-yl]ethoxy; 2-[(pyrrolidine-3-carboxylic acid)-1-yl]-ethoxy; 2-[(pyrrolidine-3-carboxylic acid $C_{1-5}$-alkylester)-1-yl]-ethoxy; 2-[(pyrrolidine-2-carboxylic acid)-1-yl]-ethoxy; 2-[(pyrrolidine-2-carboxylic acid $C_{1-5}$-alkylester)-1-yl]-ethoxy; 2-[(2-hydroxy-pyrrolidine)-1-yl]-ethoxy; 2-[(3-hydroxy-pyrrolidine)-1-yl]-ethoxy; 3-[(azetidine-3-carboxylic acid)-1-yl]-propoxy; 3-[(azetidine-3-carboxylic acid $C_{1-5}$-alkylester)-1-yl]-propoxy; 3-[(pyrrolidine-3-carboxylic acid)-1-yl]-propoxy; 3-[(pyrrolidine-3-carboxylic acid $C_{1-5}$-alkylester)-1-yl]-propoxy; 3-[(pyrrolidine-2-carboxylic acid)-1-yl]-propoxy; 3-[(pyrrolidine-2-carboxylic acid $C_{1-5}$-alkylester)-1-yl]-propoxy; 3-[(2-hydroxy-pyrrolidine)-1-yl]-propoxy; 3-[(3-hydroxy-pyrrolidine)-1-yl]-propoxy; 2-amino-3-hydroxy-2-hydroxymethyl-propoxy; CONR$^{31}$R$^{32}$; 1-(3-carboxy-azetidinyl)-1-oxo-2-ethoxy; 1-(pyrrolidine-2-carboxylic acid)-1-yl-1-oxo-2-ethoxy; 1-(pyrrolidine-3-carboxylic acid)-1-yl-1-oxo-2-ethoxy; 3-carbamoyl-propoxy; 3-($C_{1-5}$-alkylcarbamoyl)propoxy; 3-(2-hydroxyethylcarbamoyl)propoxy; —OCH$_2$—CH(OH)—CH$_2$—NR$^{31}$R$^{32}$; 3-[(azetidine-3-carboxylic acid)-1-yl]-2-hydroxypropoxy; 3-[(azetidine-3-carboxylic acid $C_{1-5}$-alkylester)-1-yl]-2-hydroxypropoxy;

2-hydroxy-3-[(pyrrolidine-3-carboxylic acid)-1-yl]-propoxy; 2-hydroxy-3-[(pyrrolidine-3-carboxylic acid $C_{1-5}$-alkylester)-1-yl]-propoxy; 2-hydroxy-3-[(pyrrolidine-2-carboxylic acid)-1-yl]-propoxy; 2-hydroxy-3-[(pyrrolidine-2-carboxylic acid $C_{1-5}$-alkylester)-1-yl]-propoxy; 2-hydroxy-3-[(2-hydroxy-pyrrolidine)-1-yl]-propoxy; 2-hydroxy-3-[(3-hydroxy-pyrrolidine)-1-yl]-propoxy; 2-hydroxy-3-pyrrolidin-1-yl-propoxy; 2-hydroxy-3-piperazin-1-yl-propoxy; 2-hydroxy-3-[4-($C_{1-5}$-alkyl)-piperazin-1-yl]-propoxy; 2-hydroxy-3-[4-(2-hydroxy-ethyl)-piperazin-1-yl]-propoxy; 2-hydroxy-3-morpholin-4-yl-propoxy; —$NR^{31}R^{32}$; —NHCO—$R^{31}$; —$CH_2$—$(CH_2)_k$—$NHSO_2R^{33}$; —$(CH_2)_p CH(OH)$—$CH_2$—$NHSO_2R^{33}$; —$OCH_2$—$(CH_2)_m$—$NHSO_2R^{33}$; —$OCH_2$—$CH(OH)$—$CH_2$—$NHSO_2R^{33}$; —$CH_2$—$(CH_2)_k$—$NHCOR^{34}$; —$(CH_2)_p CH(OH)$—$CH_2$—$NHCOR^{34}$; —$OCH_2$—$(CH_2)_m$—$NHCOR^{34}$; —$OCH_2$—$CH(OH)$—$CH_2$—$NHCOR^{34}$; —$SO_2NHR^{31}$; phenyl, wherein said phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; pyridyl, wherein said pyridyl ring can further be mono- or di-substituted, wherein the substituents are independently selected from alkyl, alkoxy, halogen, hydroxy, and —$CF_3$; furanyl, wherein said furanyl ring can further be mono- or di-substituted, wherein the substituents are independently selected from alkyl, alkoxy, and halogen; thienyl, wherein said thienyl ring can further be mono- or di-substituted, wherein the substituents are independently selected from alkyl, alkoxy, and halogen; oxadiazolyl, wherein said oxadiazolyl ring can further be mono-substituted with alkyl or phenyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; isoxazolyl, wherein said isoxazolyl ring can further be mono- or di-substituted, wherein the substituents are independently selected from alkyl, phenyl and pyridyl; halogen; alkyl; alkoxy; —$CF_3$; —$OCF_3$; hydroxy; cyano; alkoxy-carbonyl; alkyl-carbonyl; carboxyl; monoalkyl-amino; dialkyl-amino; pyrrolidino; morpholino; thiomorpholino; piperidino; N-benzyl-N-alkyl-amino; N-pyridyl-N-methyl-amino; (dialkyl-amino)-alkoxy; phenyl-alkoxy, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; phenyl-amino-carbonyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; phenyl-alkyl-amino-carbonyl, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; alkyl-amino-carbonyl; dialkyl-amino-carbonyl; pyridyl-amino-carbonyl; phenyl-carbonyl-amino, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; phenyl-alkyl-carbonyl-amino, wherein the phenyl ring can further be mono-, di-, or tri-substituted, wherein the substituents are independently selected from halogen, alkyl, alkoxy, —$CF_3$, —$OCF_3$, hydroxy, cyano, alkoxy-carbonyl, alkyl-carbonyl, carboxyl, and methylene-dioxy; alkyl-carbonyl-amino; and pyridyl-carbonyl-amino;

or $R^3$ represents the following group:

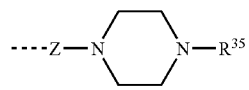

wherein Z represents phenyl or pyridyl;

$R^{31}$ represents hydrogen, methyl, ethyl, 1-propyl, 2-propyl, 2-hydroxyethyl, 2-hydroxy-1-hydroxymethyl-ethyl, 2,3-dihydroxypropyl, 2-$C_{1-5}$-alkoxyethyl, 3-hydroxypropyl, 3-$C_{1-5}$-alkoxypropyl, 2-aminoethyl, 2-($C_{1-5}$-alkylamino)ethyl, 2-(di-($C_{1-5}$-alkyl)amino)ethyl, carboxymethyl, 1-($C_{1-5}$-alkylcarboxy)methyl, 2-carboxyethyl, or 2-($C_{1-5}$-alkylcarboxy)ethyl;

$R^{32}$ represents hydrogen, methyl, or ethyl;

$R^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

$R^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

p represents 0, 1, or 2;

$R^{35}$ represents alkyl; alkyl-carbonyl; alkoxy-carbonyl; cycloalkyl-carbonyl; aryl, wherein the aryl-ring can be mono-, di-, tri-, or tetra-substituted wherein the substituents are independently selected from halogen, alkyl, alkoxy, —$CF_3$, —$OCF_3$, hydroxy, alkoxy-carbonyl, and carboxyl; aryl-carbonyl, wherein the aryl-ring can be mono-, di-, tri-, or tetra-substituted wherein the substituents are independently selected from halogen, alkyl, alkoxy, —$CF_3$, —$OCF_3$, hydroxy, alkoxy-carbonyl, and carboxyl; aryl-alkyl, wherein the aryl-ring can be mono-, di-, tri-, or tetra-substituted wherein the substituents are independently selected from halogen, alkyl, alkoxy, —$CF_3$, —$OCF_3$, hydroxy, alkoxy-carbonyl, and carboxyl; pyridyl, wherein the pyridyl-ring can be mono-, di-, or tri-substituted wherein the substituents are independently selected from halogen, alkyl, alkoxy, —$CF_3$, —$OCF_3$, hydroxy, alkoxy-carbonyl, and carboxyl; pyridyl-alkyl, wherein the pyridyl-ring can be mono-, di-, or tri-substituted wherein the substituents are independently selected from halogen, alkyl, alkoxy, —$CF_3$, —$OCF_3$, hydroxy, alkoxy-carbonyl, and carboxyl; pyrimidinyl, wherein the pyrimidinyl-ring can be mono-, or di-substituted wherein the substituents are independently selected from halogen, alkyl, alkoxy, and —$CF_3$; furanyl-carbonyl; furanyl-alkyl, wherein the furanyl-ring can be mono-, or di-substituted wherein the substituents are independently selected from methyl, hydroxy-methyl, and bromine; thienyl-alkyl that can be mono-substituted with methyl or chlorine; benzothienyl-alkyl; benzofuranyl-alkyl; imidazolyl-alkyl; or thiazolyl-alkyl; and R⁴ represents aryl —CH=CH—, wherein aryl can be mono-, di-, tri-, or tetra-substituted, wherein the substituents are independently selected from halogen, alkyl, alkoxy, —CF₃, —OCF₃, hydroxy, and cyano; pyridyl —CH=CH—, wherein pyridyl can be mono-, di-, or tri-substituted, wherein the substituents are independently selected from halogen, alkyl, alkoxy, —CF₃, —OCF₃, hydroxy, and cyano; pyrimidinyl —CH=CH—; furanyl —CH=CH—; or thienyl —CH=CH—.

9. A compound according to claim 1, wherein
X represents —CH₂— or a bond;
n represents the integer 1;
R¹ represents alkyl; cycloalkyl; hydroxy-ethyl; benzo[1,3]dioxolyl; phenyl that can be mono-substituted with halogen, alkyl, alkoxy, —CF₃, or alkyl-carbonyl, or phenyl that is di- or tri-substituted, wherein the substituents are independently selected from alkyl and halogen; pyridyl that can be mono-substituted with halogen, alkyl, or —CF₃; furanyl that can be mono-substituted with methyl, hydroxy-methyl, or bromine, or furanyl that is di-substituted with alkyl; thienyl that can be mono-substituted with methyl or chlorine; pyrimidinyl; isoquinolinyl; benzhydryl; imidazolyl optionally mono-substituted with alkyl; or thiazolyl; or X represents —C(=O)— and R¹ represents hydrogen;
R² represents indolyl; imidazolyl optionally mono-substituted with alkyl; phenyl that can be mono-substituted with halogen, alkyl, hydroxy, or cyano, or phenyl that is di-substituted with halogen; pyridyl; benzothienyl; thiazolyl; or thienyl;
R³ represents indolyl; pyridyl that can be mono-substituted with alkoxy, alkoxy-alkoxy, —NR³¹R³², morpholino, piperidino, oxo-piperidinyl, oxo-pyrrolidinyl, pyridyl, or phenyl; or phenyl which is mono-substituted with phenyl, pyridyl, alkyl, alkoxy, dialkyl-amino, morpholino, N-benzyl-N-alkyl-amino, (dialkyl-amino)-alkoxy, phenyl-alkoxy, or tetrahydro-isoquinolinyl; or R³ represents the following group:

wherein Z represents phenyl or pyridyl;
R³¹ represents 2-C₁₋₅-alkoxyethyl, phenyl, pyridyl, phenyl-alkyl, hydroxyalkyl-carbonyl, alkyl-carbonyl, cycloalkyl-carbonyl, or phenyl-carbonyl;
R³² represents hydrogen or methyl;
R³⁵ represents alkyl, alkyl-carbonyl, phenyl, pyridyl, or pyrimidinyl; and
R⁴ represents phenyl —CH=CH—, wherein phenyl can be mono-, di-, or tri-substituted, wherein the substituents are independently selected from halogen, alkyl, alkoxy, and —CF₃; or phenyl-C₁₋₁₂—CH₂—, wherein phenyl is di-substituted with —CF₃.

10. A pharmaceutical composition comprising a compound according to claim 1 and a pharmaceutically acceptable carrier material.

11. A method of preventing of treating protozoal infections using the compound of claim 1.

12. The method of claim 11 for the treatment of malaria.

13. A compound according to claim 2, wherein
X represents —(CH₂)₀₋₂— or —C(=O)—;
n represents the integer 0, 1 or 2;
R¹ represents hydrogen; alkyl; cycloalkyl; ethoxy-carbonyl; hydroxy-ethyl; benzo[1,3]dioxolyl; aryl that can be mono-, di-, tri-, or tetra-substituted, wherein the substituents are independently selected from halogen, alkyl, alkoxy, —CF₃, —OCF₃, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —CF₃, —OCF₃, hydroxy, alkoxy-carbonyl, and carboxyl; furanyl that can be mono-, or di-substituted, wherein the substituents are independently selected from methyl, hydroxy-methyl, and bromine; thienyl that can be mono-substituted with methyl or chlorine; pyrimidinyl that can be mono-substituted with alkyl, halogen, cyclopropyl, CH₃—S—, or methylsulfonyl or that can be mono- or di-substituted with methoxy; pyridazinyl; benzothienyl; benzofuranyl; quinolinyl; isoquinolinyl; or benzhydryl, wherein both phenyl rings can be mono- or di-substituted, wherein the substituents are independently selected from halogen, alkyl, alkoxy, —CF₃, —OCF₃, hydroxy, cyano, alkoxy-carbonyl, and alkyl-carbonyl;
R² represents hydrogen; alkyl; indolyl; carboxyl; alkoxy-carbonyl; amino-carbonyl; imidazolyl; cycloalkyl; aryl that can be mono-, di-, tri-, or tetra-substituted, wherein the substituents are independently selected from phenyl, halogen, alkyl, alkoxy, —CF₃, —OCF₃, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —CF₃, hydroxy, alkoxy-carbonyl, and carboxyl; benzothienyl; thiazolyl; or thienyl;
R³ represents cycloalkyl; formyl; acetyl; ethoxy-carbonyl; hydroxy-ethyl; benzo[1,3]dioxolyl; pyridyl that can be mono-, di-, or tri-substituted, wherein the substituents are independently selected from phenyl, halogen, alkyl, alkoxy, —CF₃, —OCF₃, hydroxy, alkoxy-carbonyl, and carboxyl; furanyl that can be mono- or di-substituted, wherein the substituents are independently selected from phenyl, methyl, hydroxy-methyl, and bromine; thienyl that can be mono-substituted with phenyl, methyl, or chlorine; pyrimidinyl that can be mono-substituted with phenyl, alkyl, halogen, cyclopropyl, CH₃—S—, or methylsulfonyl or that can be mono- or di-substituted with methoxy; pyridazinyl; benzothienyl; benzofuranyl; quinolinyl; isoquinolinyl; or benzhydryl, wherein both phenyl rings can be mono- or di-substituted, wherein the substituents are independently selected from halogen, alkyl, alkoxy, —CF₃, —OCF₃, hydroxy, cyano, alkoxy-carbonyl, and alkyl-carbonyl; or
R³ represents a mono-, di-, tri-, or tetra-substituted aryl, wherein the substituents are independently selected from the group consisting of:
phenyl, wherein said phenyl ring can further be mono-, di-, or tri-substituted, wherein the substituents are independently selected from halogen, alkyl, alkoxy, —CF₃, —OCF₃, hydroxy, cyano, alkoxy-carbonyl, alkyl-carbonyl, carboxyl, and methylene-dioxy; pyridyl, wherein said pyridyl ring can further be mono- or di-substituted, wherein the substituents are independently selected from alkyl, alkoxy, halogen, hydroxy, and —CF₃; furanyl, wherein said furanyl ring can further be mono- or di-substituted, wherein the substituents are independently selected from alkyl, alkoxy, and halogen; thienyl, wherein said thienyl ring can further be mono- or di-substituted, wherein the substituents are independently selected from alkyl, alkoxy, and halogen; oxadiazolyl, wherein said oxadiazolyl ring can further be mono-substituted with alkyl or phenyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; isoxazolyl, wherein said isoxazolyl ring can further be mono- or di-substituted, wherein the substituents are independently selected from alkyl, phenyl and pyridyl; halogen; alkyl; alkoxy; —CF$_3$; —OCF$_3$; hydroxy; cyano; alkoxy-carbonyl; alkyl-carbonyl; carboxyl; monoalkyl-amino; dialkyl-amino; pyrrolidino; morpholino; thiomorpholino; piperidino; N-benzyl-N-alkyl-amino; N-pyridyl-N-methyl-amino; (dialkyl-amino)-alkoxy; phenyl-alkoxy, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; phenyl-amino-carbonyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy;

phenyl-alkyl-amino-carbonyl, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; alkyl-amino-carbonyl; dialkyl-amino-carbonyl; pyridyl-amino-carbonyl; phenyl-carbonyl-amino, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; phenyl-alkyl-carbonyl-amino, wherein the phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; alkyl-carbonyl-amino; and pyridyl-carbonyl-amino; and R$^4$ represents alkyl; cycloalkyl; benzo[1,3]dioxolyl; benzo[1,3]dioxolyl —CH$_2$—; benzothienyl; benzofuranyl; indazolyl; indolyl that can be mono- or di-substituted, wherein the substituents are independently selected from halogen, alkyl, alkoxy, —CF$_3$, —OCF$_3$, and hydroxy; quinolinyl; isoquinolinyl; benzhydryl, wherein both phenyl-rings can be mono- or di-substituted, wherein the substituents are independently selected from halogen, alkyl, alkoxy, —CF$_3$, hydroxy, cyano, alkoxy-carbonyl, and alkyl-carbonyl; aryl that can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —CF$_3$, —OCF$_3$, hydroxy, alkoxy-carbonyl, and carboxyl; aryl —CH═CH—, wherein aryl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; aryl —CH$_2$—CH$_2$—, wherein aryl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl —CH═CH—, wherein pyridyl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl —CH$_2$—CH$_2$—, wherein pyridyl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; aryl —CH$_2$—, wherein aryl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl —CH$_2$—, wherein pyridyl can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; or thienyl —CH$_2$—.

14. A compound according to claim 2, wherein

X represents —CH$_2$—;

n represents the integer 1;

R$^1$ represents aryl that can be mono-, di-, tri-, or tetra-substituted, wherein the substituents are independently selected from halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —CF$_3$, —OCF$_3$, hydroxy, alkoxy-carbonyl, and carboxyl; furanyl that can be mono- or di-substituted, wherein the substituents are independently selected from methyl, hydroxy-methyl, and bromine; thienyl that can be mono-substituted with methyl or chlorine; benzothienyl; benzofuranyl; quinolinyl; or isoquinolinyl; and R$^2$ represents aryl that can be mono-, di-, tri-, or tetra-substituted, wherein the substituents are independently selected from phenyl, halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —CF$_3$, —OCF$_3$, hydroxy, alkoxy-carbonyl, and carboxyl; benzothienyl; thiazolyl; or thienyl.

15. A compound according to claim 3, wherein

X represents —CH$_2$—;

n represents the integer 1;

R$^1$ represents aryl that can be mono-, di-, tri-, or tetra-substituted, wherein the substituents are independently selected from halogen, alkyl, alkoxy, —CF$_3$, —OCF$_3$, hydroxy, cyano, alkoxy-carbonyl, alkyl-carbonyl, and carboxyl; pyridyl that can be mono-, di-, or tri-substituted, wherein the substituents are independently selected from halogen, alkyl, alkoxy, —CF$_3$, —OCF$_3$, hydroxy, alkoxy-carbonyl, and carboxyl; furanyl that can be mono- or di-substituted, wherein the substituents are independently selected from methyl, hydroxy-methyl, and bromine; thienyl that can be mono-substituted with methyl or chlorine; benzothienyl; benzofuranyl; quinolinyl; or isoquinolinyl; and R² represents aryl that can be mono-, di-, tri-, or tetra-substituted, wherein the substituents are independently selected from phenyl, halogen, alkyl, alkoxy, —CF₃, —OCF₃, hydroxy, cyano, alkoxy-carbonyl, alkyl-carbonyl, and carboxyl; pyridyl that can be mono-, di-, or tri-substituted, wherein the substituents are independently selected from phenyl, halogen, alkyl, alkoxy, —CF₃, —OCF₃, hydroxy, alkoxy-carbonyl, and carboxyl; benzothienyl; thiazolyl; or thienyl.

16. A compound according to claim 2, wherein
X represents —(CH₂)₀₋₁— or —C(=O)—;
n represents the integer 1;
R¹ represents hydrogen; alkyl; ethoxy-carbonyl; hydroxy-ethyl; benzo[1,3]dioxolyl; aryl that can be mono-substituted with halogen, alkyl, alkoxy, —CF₃, or alkyl-carbonyl; pyridyl that can be mono-substituted with halogen, alkyl, alkoxy, or —CF₃; furanyl that can be mono- or di-substituted, wherein the substituents are independently selected from methyl, hydroxy-methyl, and bromine; thienyl that can be mono-substituted with methyl or chlorine; pyrimidinyl; isoquinolinyl; or benzhydryl;
R² represents indolyl; imidazolyl; aryl that can be mono- or di-substituted, wherein the substituents are independently selected from halogen, alkyl, hydroxy, and cyano; pyridyl; benzothienyl; thiazolyl; or thienyl;
R³ represents aryl that is mono-substituted with phenyl, pyridyl, alkyl, alkoxy, pyrrolidino, (dialkyl-amino)-alkoxy or phenyl-alkoxy; and
R⁴ represents aryl —CH=CH—, wherein aryl is mono-substituted with alkoxy or —CF₃; or aryl —CH₂—CH₂—, wherein aryl is di-substituted with —CF₃.

17. A compound according to claim 3, wherein
X represents —(CH₂)₀₋₁— or —C(=O)—;
n represents the integer 1;
R¹ represents hydrogen; alkyl; ethoxy-carbonyl; hydroxy-ethyl; benzo[1,3]dioxolyl; aryl that can be mono-substituted with halogen, alkyl, alkoxy, —CF₃, or alkyl-carbonyl; pyridyl that can be mono-substituted with halogen, alkyl, alkoxy, or —CF₃; furanyl that can be mono- or di-substituted, wherein the substituents are independently selected from methyl, hydroxy-methyl, and bromine; thienyl that can be mono-substituted with methyl or chlorine; pyrimidinyl; isoquinolinyl; or benzhydryl;
R² represents indolyl; imidazolyl; aryl that can be mono- or di-substituted, wherein the substituents are independently selected from halogen, alkyl, hydroxy, and cyano; pyridyl; benzothienyl; thiazolyl; or thienyl;
R³ represents aryl that is mono-substituted with phenyl, pyridyl, alkyl, alkoxy, pyrrolidino, (dialkyl-amino)-alkoxy or phenyl-alkoxy; and
R⁴ represents aryl —CH=CH—, wherein aryl is mono-substituted with alkoxy or —CF₃; or aryl —CH₂—CH₂—, wherein aryl is di-substituted with —CF₃.

18. A compound according to claim 2, wherein
X represents —(CH₂)—;
n represents the integer 1;
R¹ represents hydrogen; methyl; cycloalkyl; benzo[1,3]dioxolyl; aryl that can be mono-, di-, tri-, or tetra-substituted, wherein the substituents are independently selected from halogen, alkyl, alkoxy, —CF₃, —OCF₃, hydroxy, cyano, alkoxy-carbonyl, alkyl-carbonyl, and carboxyl; pyridyl that can be mono-, or di-substituted, wherein the substituents are independently selected from halogen, alkyl, alkoxy, —CF₃, —OCF₃, hydroxy, alkoxy-carbonyl, and carboxyl; furanyl that can be mono-, or di-substituted, wherein the substituents are independently selected from methyl, hydroxy-methyl, and bromine; thienyl that can be mono-substituted with methyl or chlorine; pyrimidinyl that can be mono-substituted with alkyl, halogen, or cyclopropyl or that can be mono- or di-substituted with methoxy; pyridazinyl; benzothienyl; benzofuranyl; quinolinyl; isoquinolinyl; imidazolyl; thiazolyl; or oxazolyl;
R² represents cycloalkyl; aryl that can be mono-, di-, or tri-substituted, wherein the substituents are independently selected from halogen, alkyl, alkoxy, —CF₃, and cyano; pyridyl that can be mono-, or di-substituted, wherein the substituents are independently selected from halogen, alkyl, alkoxy, —CF₃, and —OCF₃; thiazolyl; or thienyl;
R³ represents cycloalkyl; pyridyl that can be mono-, di-, or tri-substituted, wherein the substituents are independently selected from: halogen, alkyl, alkoxy, —CF₃, —OCF₃, alkoxy-carbonyl, carboxyl, hydroxy-$C_{1-4}$-alkyl, 2,3-dihydroxypropyl, di-(hydroxy-$C_{1-5}$-alkyl)-$C_{1-5}$-alkyl, —CH₂—(CH₂)$_k$—NR³¹R³², (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —CH₂—(CH₂)$_p$—CONR³¹R³², —CO—NHR³¹, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, —(CH₂)$_p$CH(OH)—CH₂—NR³¹R³², hydroxy-$C_{2-5}$-alkoxy, di-(hydroxy-$C_{1-5}$-alkyl)-$C_{1-5}$-alkoxy, 2,3-dihydroxypropoxy, 2-hydroxy-3-methoxy-propoxy, —OCH₂—(CH₂),—NR³¹R³², 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid C$_{1-5}$-alkylester)-1-yl]-propoxy, 3-[(pyrrolidine-2-carboxylic acid)-1-yl]-propoxy, 3-[(pyrrolidine-2-carboxylic acid C$_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 1-(3-carboxy-azetidinyl)-1-oxo-2-ethoxy, 1-(pyrrolidine-2-carboxylic acid)-1-yl-1-oxo-2-ethoxy, 1-(pyrrolidine-3-carboxylic acid)-1-yl-1-oxo-2-ethoxy, 3-carbamoyl-propoxy, 3-(C$_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid C$_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid C$_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid C$_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(C$_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_p$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_p$CH(OH)—CH$_2$—NHCOR$^{34}$, —OCH$_2$—(CH$_2$)$_m$—NHCOR$^{34}$, —OCH$_2$—CH(OH)—CH$_2$—NHCOR$^{34}$, —SO$_2$NHR$^{31}$, and phenyl wherein the phenyl-ring can again be mono-, di-, tri-, or tetra-substituted wherein the substituents are independently selected from halogen, alkyl, alkoxy, —CF$_3$, —OCF$_3$, hydroxy, alkoxy-carbonyl, and carboxyl; furanyl that can be mono- or di-substituted, wherein the substituents are independently selected from methyl, hydroxy-methyl, bromine, and phenyl, wherein said phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; thienyl that can be mono-substituted with methyl, chlorine, or phenyl wherein said phenyl ring can further be mono-, di-, or tri-substituted, wherein the substituents are independently selected from halogen, alkyl, alkoxy, —CF$_3$, —OCF$_3$, hydroxy, cyano, alkoxy-carbonyl, alkyl-carbonyl, carboxyl, and methylene-dioxy; benzothienyl; benzofuranyl; quinolinyl; or isoquinolinyl; or R$^3$ represents a mono-, di-, tri-, or tetra-substituted aryl, wherein the substituents are independently selected from the group consisting of:

hydroxy-C$_{1-5}$-alkyl; 2,3-dihydroxypropyl; di-(hydroxy-C$_{1-5}$-alkyl)-C$_{1-5}$-alkyl; —CH$_2$—(CH$_2$)$_k$—NR$^{31}$R$^{32}$; (azetidine-3-carboxylic acid)-1-yl-methyl; (azetidine-3-carboxylic acid C$_{1-5}$-alkylester)-1-yl-methyl; 2-[(azetidine-3-carboxylic acid)-1-yl]-ethyl; 2-[(azetidine-3-carboxylic acid C$_{1-5}$-alkylester)-1-yl]-ethyl; 3-[(azetidine-3-carboxylic acid)-1-yl]-propyl; 3-[(azetidine-3-carboxylic acid C$_{1-5}$-alkylester)-1-yl]-propyl; (pyrrolidine-3-carboxylic acid)-1-yl-methyl; (pyrrolidine-3-carboxylic acid C$_{1-5}$-alkylester)-1-yl-methyl; (pyrrolidine-2-carboxylic acid)-1-yl-methyl; (pyrrolidine-2-carboxylic acid C$_{1-5}$-alkylester)-1-yl-methyl; 2-[(pyrrolidine-3-carboxylic acid)-1-yl]-ethyl; 2-[(pyrrolidine-3-carboxylic acid C$_{1-5}$-alkylester)-1-yl]-ethyl; 2-[(pyrrolidine-2-carboxylic acid)-1-yl]-ethyl; 2-[(pyrrolidine-2-carboxylic acid C$_{1-5}$-alkylester)-1-yl]ethyl; 3-[(pyrrolidine-3-carboxylic acid)-1-yl]-propyl; 3-[(pyrrolidine-3-carboxylic acid C$_{1-5}$-alkylester)-1-yl]-propyl; 3-[(pyrrolidine-2-carboxylic acid)-1-yl]-propyl; 3-[(pyrrolidine-2-carboxylic acid C$_{1-5}$-alkylester)-1-yl]-propyl; —CH$_2$—(CH$_2$)$_p$—CONR$^{31}$R$^{32}$; —CO—NHR$^{31}$; 1-(3-carboxy-azetidinyl)-2-acetyl; 1-(2-carboxy-pyrrolidinyl)-2-acetyl; 1-(3-carboxy-pyrrolidinyl)-2-acetyl; 1-(3-carboxy-azetidinyl)-3-propionyl; 1-(2-carboxy-pyrrolidinyl)-3-propionyl; 1-(3-carboxy-pyrrolidinyl)-3-propionyl; —(CH$_2$)$_p$CH(OH)—CH$_2$—NR$^{31}$R$^{32}$; hydroxy-C$_{2-5}$-alkoxy; di-(hydroxy-C$_{1-5}$-alkyl)-C$_{1-5}$-alkoxy; 2,3-dihydroxypropoxy; 2-hydroxy-3-methoxy-propoxy; —OCH$_2$—(CH$_2$)$_m$—NR$^{31}$R$^{32}$; 2-pyrrolidin-1-yl-ethoxy; 3-pyrrolidin-1-yl-propoxy; 2-piperazin-1-yl-ethoxy; 2-[4-(C$_{1-5}$-alkyl)-piperazin-1-yl]-ethoxy; 2-[4-(2-hydroxy-ethyl)-piperazin-1-yl]-ethoxy; 3-piperazin-1-yl-propoxy; 3-[4-(C$_{1-5}$-alkyl)-piperazin-1-yl]-propoxy; 3-[4-(2-hydroxy-ethyl)-piperazin-1-yl]-propoxy; 2-morpholin-4-yl-ethoxy; 3-morpholin-4-yl-propoxy; 2-[(azetidine-3-carboxylic acid)-1-yl]-ethoxy; 2-[(azetidine-3-carboxylic acid C$_{1-5}$-alkylester)-1-yl]ethoxy; 2-[(pyrrolidine-3-carboxylic acid)-1-yl]-ethoxy; 2-[(pyrrolidine-3-carboxylic acid C$_{1-5}$-alkylester)-1-yl]-ethoxy; 2-[(pyrrolidine-2-carboxylic acid)-1-yl]-ethoxy; 2-[(pyrrolidine-2-carboxylic acid C$_{1-5}$-alkylester)-1-yl]-ethoxy; 2-[(2-hydroxy-pyrrolidine)-1-yl]-ethoxy; 2-[(3-hydroxy-pyrrolidine)-1-yl]-ethoxy; 3-[(azetidine-3-carboxylic acid)-1-yl]propoxy; 3-[(azetidine-3-carboxylic acid C$_{1-5}$-alkylester)-1-yl]propoxy; 3-[(pyrrolidine-3-carboxylic acid)-1-yl]-propoxy; 3-[(pyrrolidine-3-carboxylic acid C$_{1-5}$-alkylester)-1-yl]-propoxy; 3-[(pyrrolidine-2-carboxylic acid)-1-yl]-propoxy; 3-[(pyrrolidine-2-carboxylic acid C$_{1-5}$-alkylester)-1-yl]-propoxy; 3-[(2-hydroxy-pyrrolidine)-1-yl]propoxy; 3-[(3-hydroxy-pyrrolidine)-1-yl]-propoxy; 2-amino-3-hydroxy-2-hydroxymethyl-propoxy; —O—CH$_2$—CONR$^{31}$R$^{32}$; 1-(3-carboxy-azetidinyl)-1-oxo-2-ethoxy; 1-(pyrrolidine-2-carboxylic acid)-1-yl-1-oxo-2-ethoxy; 1-(pyrrolidine-3-carboxylic acid)-1-yl-1-oxo-2-ethoxy; 3-carbamoyl-propoxy; 3-(C$_{1-5}$-alkylcarbamoyl)propoxy; 3-(2-hydroxyethylcarbamoyl)propoxy; —OCH$_2$—CH(OH)—CH$_2$—NR$^{31}$R$^{32}$; 3-[(azetidine-3-carboxylic acid)-1-yl]-2-hydroxypropoxy; 3-[(azetidine-3-carboxylic acid C$_{1-5}$-alkylester)-1-yl]-2-hydroxypropoxy; 2-hydroxy-3-[(pyrrolidine-3-carboxylic acid)-1-yl]-propoxy; 2-hydroxy-3-[(pyrrolidine-3-carboxylic acid C$_{1-5}$-alkylester)-1-yl]propoxy; 2-hydroxy-3-[(pyrrolidine-2-carboxylic acid)-1-yl]-propoxy; 2-hydroxy-3-[(pyrrolidine-2-carboxylic acid C$_{1-5}$-alkylester)-1-yl]-propoxy; 2-hydroxy-3-[(2-hydroxy-pyrrolidine)-1-yl]-propoxy; 2-hydroxy-3-[(3-hydroxy-pyrrolidine)-1-yl]-propoxy; 2-hydroxy-3-pyrrolidin-1-yl-propoxy; 2-hydroxy-3-piperazin-1-yl-propoxy; 2-hydroxy-3-[4-(C$_{1-5}$-alkyl)-piperazin-1-yl]-propoxy; 2-hydroxy-3-[4-(2-hydroxy-ethyl)-piperazin-1-yl]-propoxy; 2-hydroxy-3-morpholin-4-yl-propoxy; —NR$^{31}$R$^{32}$; —NHCO—R$^{31}$; —CH$_2$—(CH$_2$)$_k$—NHSO$_2$R$^{33}$; —(CH$_2$)$_p$CH(OH)—CH$_2$—NHSO$_2$R$^{33}$; —OCH$_2$—(CH$_2$)$_m$—NHSO$_2$R$^{33}$; —OCH$_2$—CH(OH)—CH$_2$—NHSO$_2$R$^{33}$; —CH$_2$—(CH$_2$)$_k$—NHCOR$^{34}$; —(CH$_2$)$_p$CH(OH)—CH$_2$—NHCOR$^{34}$; —OCH$_2$—

(CH₂)ₘ—NHCOR³⁴; —OCH₂—CH(OH)—CH₂—NHCOR³⁴; —SO₂NHR³¹; phenyl, wherein said phenyl ring can further be mono-, di-, or tri-substituted, wherein the substituents are independently selected from halogen, alkyl, alkoxy, —CF₃, —OCF₃, hydroxy, cyano, alkoxy-carbonyl, alkyl-carbonyl, carboxyl, and methylene-dioxy; pyridyl, wherein said pyridyl ring can further be mono- or di-substituted, wherein the substituents are independently selected from alkyl, alkoxy, halogen, hydroxy, and —CF₃; furanyl, wherein said furanyl ring can further be mono- or di-substituted, wherein the substituents are independently selected from alkyl, alkoxy, and halogen; thienyl, wherein said thienyl ring can further be mono- or di-substituted, wherein the substituents are independently selected from alkyl, alkoxy, and halogen; oxadiazolyl, wherein said oxadiazolyl ring can further be mono-substituted with alkyl or phenyl, wherein the phenyl ring can further be mono-, di-, or tri-substituted, wherein the substituents are independently selected from halogen, alkyl, alkoxy, —CF₃, —OCF₃, hydroxy, cyano, alkoxy-carbonyl, alkyl-carbonyl, carboxyl, and methylene-dioxy; isoxazolyl, wherein said isoxazolyl ring can further be mono- or di-substituted, wherein the substituents are independently selected from alkyl, phenyl and pyridyl; halogen; alkyl; alkoxy; —CF₃; —OCF₃; hydroxy; cyano; alkoxy-carbonyl; alkyl-carbonyl; carboxyl; monoalkyl-amino; dialkyl-amino; pyrrolidino; morpholino; thiomorpholino; piperidino; N-benzyl-N-alkyl-amino; N-pyridyl-N-methyl-amino; (dialkyl-amino)-alkoxy; phenyl-alkoxy, wherein the phenyl ring can further be mono-, di-, or tri-substituted, wherein the substituents are independently selected from halogen, alkyl, alkoxy, —CF₃, —OCF₃, hydroxy, cyano, alkoxy-carbonyl, alkyl-carbonyl, carboxyl, and methylene-dioxy; phenyl-amino-carbonyl, wherein the phenyl ring can further be mono-, di-, or tri-substituted, wherein the substituents are independently selected from halogen, alkyl, alkoxy, —CF₃, —OCF₃, hydroxy, cyano, alkoxy-carbonyl, alkyl-carbonyl, carboxyl, and methylene-dioxy; phenyl-alkyl-amino-carbonyl, wherein the phenyl ring can further be mono-, di-, or tri-substituted, wherein the substituents are independently selected from halogen, alkyl, alkoxy, —CF₃, —OCF₃, hydroxy, cyano, alkoxy-carbonyl, alkyl-carbonyl, carboxyl, and methylene-dioxy; alkyl-amino-carbonyl; dialkyl-amino-carbonyl; pyridyl-amino-carbonyl; phenyl-carbonyl-amino, wherein the phenyl ring can further be mono-, di-, or tri-substituted, wherein the substituents are independently selected from halogen, alkyl, alkoxy, —CF₃, —OCF₃, hydroxy, cyano, alkoxy-carbonyl, alkyl-carbonyl, carboxyl, and methylene-dioxy; phenyl-alkyl-carbonyl-amino, wherein the phenyl ring can further be mono-, di-, or tri-substituted, wherein the substituents are independently selected from halogen, alkyl, alkoxy, —CF₃, —OCF₃, hydroxy, cyano, alkoxy-carbonyl, alkyl-carbonyl, carboxyl, and methylene-dioxy; alkyl-carbonyl-amino; and pyridyl-carbonyl-amino;

or R³ represents the following group:

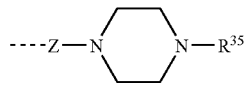

wherein Z represents phenyl or pyridyl;

R³¹ represents hydrogen, methyl, ethyl, 1-propyl, 2-propyl, 2-hydroxyethyl, 2-hydroxy-1-hydroxymethyl-ethyl, 2,3-dihydroxypropyl, 2-C₁₋₅-alkoxyethyl, 3-hydroxypropyl, 3-C₁₋₅-alkoxypropyl, 2-aminoethyl, 2-(C₁₋₅-alkylamino)ethyl, 2-(di-(C₁₋₅-alkyl)amino)ethyl, carboxymethyl, 1-(C₁₋₅-alkylcarboxy)methyl, 2-carboxyethyl, or 2-(C₁₋₅-alkylcarboxy)ethyl;

R³² represents hydrogen, methyl, or ethyl;

R³³ represents methyl, ethyl, propyl, isopropyl, butyl, 2-hydroxyethyl, 2-methoxyethyl, methylamino, ethylamino, propylamino, isopropylamino, n-butylamino, or dimethylamino;

R³⁴ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

p represents 0, 1, or 2;

R³⁵ represents alkyl; alkyl-carbonyl; alkoxy-carbonyl; cycloalkyl-carbonyl; aryl, wherein the aryl-ring can be mono-, di-, tri-, or tetra-substituted wherein the substituents are independently selected from halogen, alkyl, alkoxy, —CF₃, —OCF₃, hydroxy, alkoxy-carbonyl, and carboxyl; aryl-carbonyl, wherein the aryl-ring can be mono-, di-, tri-, or tetra-substituted wherein the substituents are independently selected from halogen, alkyl, alkoxy, —CF₃, —OCF₃, hydroxy, alkoxy-carbonyl, and carboxyl; aryl-alkyl, wherein the aryl-ring can be mono-, di-, tri-, or tetra-substituted wherein the substituents are independently selected from halogen, alkyl, alkoxy, —CF₃, —OCF₃, hydroxy, alkoxy-carbonyl, and carboxyl; pyridyl, wherein the pyridyl-ring can be mono-, di-, or tri-substituted wherein the substituents are independently selected from halogen, alkyl, alkoxy, —CF₃, —OCF₃, hydroxy, alkoxy-carbonyl, and carboxyl; pyridyl-alkyl, wherein the pyridyl-ring can be mono-, di-, or tri-substituted wherein the substituents are independently selected from halogen, alkyl, alkoxy, —CF₃, —OCF₃, hydroxy, alkoxy-carbonyl, and carboxyl; pyrimidinyl, wherein the pyrimidinyl-ring can be mono-, or di-substituted wherein the substituents are independently selected from halogen, alkyl, alkoxy, and —CF₃; furanyl-carbonyl; furanyl-alkyl, wherein the furanyl-ring can be mono-, or di-substituted wherein the substituents are independently selected from methyl, hydroxy-methyl, and bromine; thienyl-alkyl that can be mono-substituted with methyl or chlorine; benzothienyl-alkyl; benzofuranyl-alkyl; imidazolyl-alkyl; or thiazolyl-alkyl; and R⁴ represents aryl —CH=CH—, wherein aryl can be mono-, di-, tri-, or tetra-substituted, wherein the substituents are independently selected from halogen, alkyl, alkoxy, —CF₃, OCF₃, hydroxy, and cyano; pyridyl —CH=CH—, wherein pyridyl can be mono-, di-, or tri-substituted, wherein the substituents are independently selected from halogen, alkyl, alkoxy, —CF₃, —OCF₃, hydroxy, and cyano; pyrimidinyl —CH=CH—; furanyl —CH=CH—; or thienyl —CH=CH—.

19. A compound according to claim 2, wherein

X represents —CH₂— or a bond;

n represents the integer 1;

R¹ represents alkyl; cycloalkyl; hydroxy-ethyl; benzo[1,3]dioxolyl; phenyl that can be mono-substituted with halogen, alkyl, alkoxy, —CF₃, or alkyl-carbonyl, or phenyl that is di- or tri-substituted, wherein the substituents are independently selected from alkyl and halogen; pyridyl that can be mono-substituted with halogen, alkyl, or —$CF_3$; furanyl that can be mono-substituted with methyl, hydroxy-methyl, or bromine, or furanyl that is di-substituted with alkyl; thienyl that can be mono-substituted with methyl or chlorine; pyrimidinyl; isoquinolinyl; benzhydryl; imidazolyl optionally mono-substituted with alkyl; or thiazolyl; or X represents —C(=O)— and $R^1$ represents hydrogen;

$R^2$ represents indolyl; imidazolyl optionally mono-substituted with alkyl; phenyl that can be mono-substituted with halogen, alkyl, hydroxy, or cyano, or phenyl that is di-substituted with halogen; pyridyl; benzothienyl; thiazolyl; or thienyl;

$R^3$ represents indolyl; pyridyl that can be mono-substituted with alkoxy, alkoxy-alkoxy, —$NR^{31}R^{32}$, morpholino, piperidino, oxo-piperidinyl, oxo-pyrrolidinyl, pyridyl, or phenyl; or phenyl which is mono-substituted with phenyl, pyridyl, alkyl, alkoxy, dialkyl-amino, morpholino, N-benzyl-N-alkyl-amino, (dialkyl-amino)-alkoxy, phenyl-alkoxy, or tetrahydro-isoquinolinyl; or $R^3$ represents the following group:

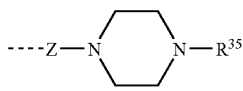

wherein Z represents phenyl or pyridyl;

$R^{31}$ represents 2-$C_{1-5}$-alkoxyethyl, phenyl, pyridyl, phenyl-alkyl, hydroxyalkyl-carbonyl, alkyl-carbonyl, cycloalkyl-carbonyl, or phenyl-carbonyl;

$R^{32}$ represents hydrogen or methyl;

$R^{35}$ represents alkyl, alkyl-carbonyl, phenyl, pyridyl, or pyrimidinyl; and $R^4$ represents phenyl —CH=CH—, wherein phenyl can be mono-, di-, or tri-substituted, wherein the substituents are independently selected from halogen, alkyl, alkoxy, and —$CF_3$; or phenyl —$CH_2$—$CH_2$—, wherein phenyl is di-substituted with —$CF_3$.

20. A compound according to claim 2, selected from the group consisting of:
N—[(S)-1-benzyl-2-(4-benzyl-piperazin-1-yl)-2-oxo-ethyl]-N-(4-pentyl-benzyl)-3-(4-trifluoromethyl-phenyl)-acrylamide,
N—[(S)-1-benzyl-2-(4-benzyl-piperazin-1-yl)-2-oxo-ethyl]-N-(4-pentyl-benzyl)-3-(3-trifluoromethyl-phenyl)-acrylamide,
N—[(S)-1-benzyl-2-(4-benzyl-piperazin-1-yl)-2-oxo-ethyl]-N-(4-pentyl-benzyl)-3-(2-trifluoromethyl-phenyl)-acrylamide,
N—[(S)-1-benzyl-2-(4-benzyl-piperazin-1-yl)-2-oxo-ethyl]-3-(4-methoxy-phenyl)-N-(4-pentyl-benzyl)-acrylamide,
N—[(S)-1-benzyl-2-(4-benzyl-piperazin-1-yl)-2-oxo-ethyl]-3-(3-methoxy-phenyl)-N-(4-pentyl-benzyl)-acrylamide, and
N—[(S)-1-benzyl-2-(4-benzyl-piperazin-1-yl)-2-oxo-ethyl]-3-(3,5-bis-trifluoromethyl-phenyl)-N-(4-pentyl-benzyl)-propionamide.

21. A compound according to claim 2, selected from the group consisting of:
N—[(S)-1-Benzyl-2-(4-benzyl-piperazin-1-yl)-2-oxo-ethyl]-N-(4-pyridin-2-yl-benzyl)-3-(4-trifluoromethyl-phenyl)-acrylamide,
N—[(S)-1-Benzyl-2-(4-benzyl-piperazin-1-yl)-2-oxo-ethyl]-N-(4-pyridin-4-yl-benzyl)-3-(4-trifluoromethyl-phenyl)-acrylamide,
N—[(S)-1-Benzyl-2-(4-benzyl-piperazin-1-yl)-2-oxo-ethyl]-N-(4-pyridin-3-yl-benzyl)-3-(4-trifluoromethyl-phenyl)-acrylamide,
N—[(S)-1-Benzyl-2-(4-benzyl-piperazin-1-yl)-2-oxo-ethyl]-N-[4-(4-pyridin-2-yl-piperazin-1-yl)-benzyl]-3-(4-trifluoromethyl-phenyl)-acrylamide,
N—[(S)-1-Benzyl-2-(4-benzyl-piperazin-1-yl)-2-oxo-ethyl]-N-(4-benzyloxy-benzyl)-3-(4-trifluoromethyl-phenyl)-acrylamide,
N—[(S)-1-Benzyl-2-(4-benzyl-piperazin-1-yl)-2-oxo-ethyl]-N-[4-(4-pyrimidin-2-yl-piperazin-1-yl)-benzyl]-3-(4-trifluoromethyl-phenyl)-acrylamide,
N-[4-(4-Acetyl-piperazin-1-yl)-benzyl]-N—[(S)-1-benzyl-2-(4-benzyl-piperazin-1-yl)-2-oxo-ethyl]-3-(4-trifluoromethyl-phenyl)-acrylamide,
N—[(S)-1-Benzyl-2-(4-benzyl-piperazin-1-yl)-2-oxo-ethyl]-N-[6-(4-pyrimidin-2-yl-piperazin-1-yl)-pyridin-3-ylmethyl]-3-(4-trifluoromethyl-phenyl)-acrylamide,
N—[(S)-1-Benzyl-2-(4-furan-2-ylmethyl-piperazin-1-yl)-2-oxo-ethyl]-N-(4-pyridin-2-yl-benzyl)-3-(4-trifluoromethyl-phenyl)-acrylamide,
N—[(S)-1-Benzyl-2-(4-benzyl-piperazin-1-yl)-2-oxo-ethyl]-N-(4-ethoxy-benzyl)-3-(4-trifluoromethyl-phenyl)-acrylamide,
N—[(S)-1-Benzyl-2-(4-benzyl-piperazin-1-yl)-2-oxo-ethyl]-N-(4-ethoxy-benzyl)-3-(4-trifluoromethyl-phenyl)-acrylamide,
N—[(S)-1-Benzyl-2-oxo-2-(4-thiophen-2-ylmethyl-piperazin-1-yl)-ethyl]-N-(4-pyridin-2-yl-benzyl)-3-(4-trifluoromethyl-phenyl)-acrylamide,
N—[(S)-1-Benzyl-2-(4-benzyl-piperazin-1-yl)-2-oxo-ethyl]-N-(4-ethyl-benzyl)-3-(4-trifluoromethyl-phenyl)-acrylamide,
N—{(S)-1-Benzyl-2-[4-(4-methyl-benzyl)-piperazin-1-yl]-2-oxo-ethyl}-N-(4-pyridin-2-yl-benzyl)-3-(4-trifluoromethyl-phenyl)-acrylamide,
N—{(S)-1-Benzyl-2-[4-(4-ethyl-benzyl)-piperazin-1-yl]-2-oxo-ethyl}-N-(4-pyridin-2-yl-benzyl)-3-(4-trifluoromethyl-phenyl)-acrylamide,
N—{(S)-1-Benzyl-2-[4-(3H-imidazol-4-ylmethyl)-piperazin-1-yl]-2-oxo-ethyl}-N-(4-pyridin-2-yl-benzyl)-3-(4-trifluoromethyl-phenyl)-acrylamide,
N—[(S)-1-Benzyl-2-(4-benzyl-piperazin-1-yl)-2-oxo-ethyl]-N-[2,4']bipyridinyl-5-ylmethyl-3-(4-trifluoromethyl-phenyl)-acrylamide,
N—{(S)-1-Benzyl-2-[4-(4-isopropyl-benzyl)-piperazin-1-yl]-2-oxo-ethyl}-N-(4-pyridin-2-yl-benzyl)-3-(4-trifluoromethyl-phenyl)-acrylamide,
N—[(S)-1-Benzyl-2-oxo-2-(4-thiazol-2-ylmethyl-piperazin-1-yl)-ethyl]-N-(4-pyridin-2-yl-benzyl)-3-(4-trifluoromethyl-phenyl)-acrylamide,
N—[(S)-1-Benzyl-2-(4-benzyl-piperazin-1-yl)-2-oxo-ethyl]-N-(4-pyridin-2-yl-benzyl)-3-p-tolyl-acrylamide,
N—[(S)-1-Benzyl-2-oxo-2-(4-pyridin-3-ylmethyl-piperazin-1-yl)-ethyl]-N-(4-pyridin-2-yl-benzyl)-3-(4-trifluoromethyl-phenyl)-acrylamide,
N—[(S)-1-Benzyl-2-oxo-2-(4-thiophen-3-ylmethyl-piperazin-1-yl)-ethyl]-N-(4-pyridin-2-yl-benzyl)-3-(4-trifluoromethyl-phenyl)-acrylamide,
N—{(S)-1-Benzyl-2-[4-(2,3-difluoro-4-methyl-benzyl)-piperazin-1-yl]-2-oxo-ethyl}-N-(4-pyridin-2-yl-benzyl)-3-(4-trifluoromethyl-phenyl)-acrylamide, N—{(S)-1-Benzyl-2-[4-(3,4-dimethyl-benzyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-oxo-2-(4-pyrimidin-5-ylmethyl-piperazin-1-yl)-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-ethoxy-benzyl)-3-(4-methoxy-phenyl)-acrylamide, N—[(S)-1-Benzyl-2-oxo-2-(4-pyridin-2-ylmethyl-piperazin-1-yl)-ethyl]-N-(4-pyridin-2-yl-benzyl)-3-(4-trifluoromethyl-phenyl)-acrylamide, N—{(S)-1-Benzyl-2-[4-(3-methyl-benzyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-p-tolyl-acrylamide, N—{(S)-1-Benzyl-2-oxo-2-[4-(4-trifluoromethyl-benzyl)-piperazin-1-yl]-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-3-(4-bromo-phenyl)-N-(4-pyridin-2-yl-benzyl)-acrylamide, N—[(S)-1-Benzyl-2-(4-benzyl-piperazin-1-yl)-2-oxo-ethyl]-3-(4-bromo-phenyl)-N-(4-ethyl-benzyl)-acrylamide, N—[(S)-1-Benzyl-2-(4-benzyl-piperazin-1-yl)-2-oxo-ethyl]-N-(4-ethyl-benzyl)-3-(3-fluoro-4-methoxy-phenyl)-acrylamide, N—[(S)-1-Benzyl-2-(4-benzyl-piperazin-1-yl)-2-oxo-ethyl]-N-(4-pyridin-2-yl-benzyl)-3-(6-trifluoromethyl-pyridin-3-yl)-acrylamide, N—[(S)-1-Benzyl-2-(4-benzyl-piperazin-1-yl)-2-oxo-ethyl]-N-(4-ethyl-benzyl)-3-(4-methoxy-2,3-dimethyl-phenyl)-acrylamide, N—[(S)-1-Benzyl-2-(4-benzyl-piperazin-1-yl)-2-oxo-ethyl]-N-[2,3']bipyridinyl-5-ylmethyl-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(4-methoxy-3-methyl-phenyl)-acrylamide, N—[(S)-1-Benzyl-2-(4-benzyl-piperazin-1-yl)-2-oxo-ethyl]-N-[4-(3-dimethylamino-propoxy)-benzyl]-3-(4-trifluoromethyl-phenyl)-acrylamide, N—{(S)-1-Benzyl-2-[4-(6-methoxy-pyridin-3-ylmethyl)-piperazin-1-yl]-2-oxo-ethyl}-N-(4-pentyl-benzyl)-3-(4-trifluoromethyl-phenyl)-acrylamide, N—[(S)-1-Benzyl-2-(4-benzyl-piperazin-1-yl)-2-oxo-ethyl]-3-(3,5-dimethoxy-phenyl)-N-(4-ethyl-benzyl)-acrylamide, N—[(S)-1-Benzyl-2-(4-benzyl-piperazin-1-yl)-2-oxo-ethyl]-3-(3-fluoro-4-methoxy-phenyl)-N-(4-pyridin-2-yl-benzyl)-acrylamide, N—[(S)-1-Benzyl-2-(4-benzyl-piperazin-1-yl)-2-oxo-ethyl]-N-[4-(3,4-dihydro-1H-isoquinolin-2-yl)-benzyl]-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(3-fluoro-4-trifluoromethyl-phenyl)-acrylamide, N—[(S)-1-Benzyl-2-(4-benzyl-piperazin-1-yl)-2-oxo-ethyl]-N-pyridin-3-ylmethyl-3-(4-trifluoromethyl-phenyl)-acrylamide, N—[(S)-1-Benzyl-2-(4-benzyl-piperazin-1-yl)-2-oxo-ethyl]-N-[4-(3-dimethylamino-propoxy)-benzyl]-3-(4-methoxy-phenyl)-acrylamide, N-Benzyl-N—[(S)-1-benzyl-2-(4-benzyl-piperazin-1-yl)-2-oxo-ethyl]-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(2-fluoro-4-trifluoromethyl-phenyl)-acrylamide, N-[2-(4-Benzyl-piperazin-1-yl)-(S)-1-(4-chloro-benzyl)-2-oxo-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-morpholin-4-yl-benzyl)-3-(4-trifluoromethyl-phenyl)-acrylamide, N—[(S)-1-Benzyl-2-oxo-2-(4-pyridin-4-ylmethyl-piperazin-1-yl)-ethyl]-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-[6-(4-pyridin-2-yl-piperazin-1-yl)-pyridin-3-ylmethyl]-3-(4-trifluoromethyl-phenyl)-acrylamide, N—{(S)-1-Benzyl-2-[4-(1H-imidazol-2-ylmethyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(4-ethyl-benzyl)-3-(4-methoxy-phenyl)-acrylamide, N-[2-(4-Benzyl-piperazin-1-yl)-2-oxo-(S)-1-pyridin-2-ylmethyl-ethyl]-N-(4-pyridin-2-yl-benzyl)-3-(4-trifluoromethyl-phenyl)-acrylamide, N—{(S)-1-Benzyl-2-[4-(6-methyl-pyridin-2-ylmethyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-N-(6-morpholin-4-yl-pyridin-3-ylmethyl)-3-(4-trifluoromethyl-phenyl)-acrylamide, N—[(S)-1-Benzyl-2-(4-benzyl-piperazin-1-yl)-2-oxo-ethyl]-N-[6-(2-oxo-pyrrolidin-1-yl)-pyridin-3-ylmethyl]-3-(4-trifluoromethyl-phenyl)-acrylamide, N—[(S)-1-Benzyl-2-(4-benzyl-piperazin-1-yl)-2-oxo-ethyl]-N-(6-phenyl-pyridin-3-ylmethyl)-3-(4-trifluoromethyl-phenyl)-acrylamide, N-[6-(4-Acetyl-piperazin-1-yl)-pyridin-3-ylmethyl]-N—[(S)-1-benzyl-2-(4-benzyl-piperazin-1-yl)-2-oxo-ethyl]-3-(4-trifluoromethyl-phenyl)-acrylamide, N—[(S)-1-Benzyl-2-(4-benzyl-piperazin-1-yl)-2-oxo-ethyl]-N-[4-(4-phenyl-piperazin-1-yl)-benzyl]-3-(4-trifluoromethyl-phenyl)-acrylamide, N—[(S)-1-Benzyl-2-(4-benzyl-piperazin-1-yl)-2-oxo-ethyl]-N-thiophen-3-ylmethyl-3-(4-trifluoromethyl-phenyl)-acrylamide, N—{(S)-1-Benzyl-2-[4-(3,5-dimethyl-benzyl)-piperazin-1-yl]-2-oxo-ethyl}-N-(4-pyridin-2-yl-benzyl)-3-(4-trifluoromethyl-phenyl)-acrylamide, N—[(S)-1-Benzyl-2-(4-benzyl-piperazin-1-yl)-2-oxo-ethyl]-3-(4-fluoro-phenyl)-N-(4-pyridin-2-yl-benzyl)-acrylamide, N—[(S)-1-Benzyl-2-(4-benzyl-piperazin-1-yl)-2-oxo-ethyl]-N-(4-ethyl-benzyl)-3-(4-fluoro-phenyl)-acrylamide, N—[(S)-1-Benzyl-2-(4-benzyl-piperazin-1-yl)-2-oxo-ethyl]-N-[6-(2-hydroxy-acetylamino)-pyridin-3-ylmethyl]-3-(4-trifluoromethyl-phenyl)-acrylamide, N-[2-(4-Benzyl-piperazin-1-yl)-2-oxo-(S)-1-thiazol-4-yl-methyl-ethyl]-N-(4-pyridin-2-yl-benzyl)-3-(4-trifluoromethyl-phenyl)-acrylamide, N—[(S)-1-Benzyl-2-(4-methyl-piperazin-1-yl)-2-oxo-ethyl]-N-(4-pentyl-benzyl)-3-(4-trifluoromethyl-phenyl)-acrylamide, N—[(S)-1-Benzyl-2-(4-benzyl-piperazin-1-yl)-2-oxo-ethyl]-N-[6-(2-methoxy-ethoxy)-pyridin-3-ylmethyl]-3-(4-trifluoromethyl-phenyl)-acrylamide, N—[(S)-1-Benzyl-2-(4-benzyl-piperazin-1-yl)-2-oxo-ethyl]-N-[4-(4-ethyl-piperazin-1-yl)-benzyl]-3-(4-trifluoromethyl-phenyl)-acrylamide,
N—[(S)-1-Benzyl-2-(4-benzyl-piperazin-1-yl)-2-oxo-ethyl]-N-(6-methoxy-pyridin-3-ylmethyl)-3-(4-trifluoromethyl-phenyl)-acrylamide,
N—[(S)-1-Benzyl-2-(4-benzyl-piperazin-1-yl)-2-oxo-ethyl]-N-thiazol-2-ylmethyl-3-(4-trifluoromethyl-phenyl)-acrylamide,
N—{(S)-1-Benzyl-2-[4-(2,3-dimethyl-benzyl)-piperazin-1-yl]-2-oxo-ethyl}-N-(4-pyridin-2-yl-benzyl)-3-(4-trifluoromethyl-phenyl)-acrylamide,
N—[(S)-1-Benzyl-2-oxo-2-(4-thiophen-2-ylmethyl-piperazin-1-yl)-ethyl]-N-pyridin-3-ylmethyl-3-(4-trifluoromethyl-phenyl)-acrylamide,
N—[(S)-1-Benzyl-2-(4-benzyl-piperazin-1-yl)-2-oxo-ethyl]-N-pyridin-4-ylmethyl-3-(4-trifluoromethyl-phenyl)-acrylamide,
N—[(S)-1-Benzyl-2-(4-furan-2-ylmethyl-piperazin-1-yl)-2-oxo-ethyl]-N-pyridin-3-ylmethyl-3-(4-trifluoromethyl-phenyl)-acrylamide,
N—[(S)-1-Benzyl-2-[4-(2,4-dimethyl-benzyl)-piperazin-1-yl]-2-oxo-ethyl]-N-(4-pyridin-2-yl-benzyl)-3-(4-trifluoromethyl-phenyl)-acrylamide,
N-[2-(4-Benzyl-piperazin-1-yl)-2-oxo-1-thiazol-2-ylmethyl-ethyl]-N-(4-pyridin-2-yl-benzyl)-3-(4-trifluoromethyl-phenyl)-acrylamide,
N—[(S)-1-Benzyl-2-(4-benzyl-piperazin-1-yl)-2-oxo-ethyl]-N-[6-(2-methoxy-ethylamino)-pyridin-3-ylmethyl]-3-(4-trifluoromethyl-phenyl)-acrylamide,
N—[(S)-1-Benzyl-2-(4-benzyl-piperazin-1-yl)-2-oxo-ethyl]-N-(6-ethoxy-pyridin-3-ylmethyl)-3-(4-trifluoromethyl-phenyl)-acrylamide,
N—[(S)-1-Benzyl-2-(4-benzyl-piperazin-1-yl)-2-oxo-ethyl]-N-(6-[(2-hydroxy-ethyl)-methyl-amino]-pyridin-3-ylmethyl)-3-(4-trifluoromethyl-phenyl)-acrylamide, and
N—[(S)-1-Benzyl-2-(4-benzyl-piperazin-1-yl)-2-oxo-ethyl]-3-(2-fluoro-4-trifluoromethyl-phenyl)-N-(4-pyridin-2-yl-benzyl)-acrylamide.

22. A pharmaceutical composition comprising a compound according to claim 2 and a pharmaceutically acceptable carrier material.

23. A pharmaceutical composition comprising a compound according to claim 3 and a pharmaceutically acceptable carrier material.

24. A pharmaceutical composition comprising a compound according to claim 4 and a pharmaceutically acceptable carrier material.

25. A pharmaceutical composition comprising a compound according to claim 5 and a pharmaceutically acceptable carrier material.

26. A pharmaceutical composition comprising a compound according to claim 6 and a pharmaceutically acceptable carrier material.

27. A pharmaceutical composition comprising a compound according to claim 7 and a pharmaceutically acceptable carrier material.

28. A pharmaceutical composition comprising a compound according to claim 8 and a pharmaceutically acceptable carrier material.

29. A pharmaceutical composition comprising a compound according to claim 9 and a pharmaceutically acceptable carrier material.

30. A pharmaceutical composition comprising a compound according to claim 23 and a pharmaceutically acceptable carrier material.

31. A pharmaceutical composition comprising a compound according to claim 25 and a pharmaceutically acceptable carrier material.

* * * * *

UNITED STATES PATENT AND TRADEMARK OFFICE
CERTIFICATE OF CORRECTION

PATENT NO. : 8,067,419 B2
APPLICATION NO. : 12/090816
DATED : November 29, 2011
INVENTOR(S) : Christoph Binkert et al.

Page 1 of 1

It is certified that error appears in the above-identified patent and that said Letters Patent is hereby corrected as shown below:

Column 115, line 55: "—O—$C_{1-12}$—$CONR^{31}R^{32}$" should read "—O—$CH_2$—$CONR^{31}R^{32}$"
Column 115, line 58: "carboxylic acid)-1-yl -1-oxo-2-ethoxy," should read "carboxylic acid)-1-yl-1-oxo-2-ethoxy"
Column 117, line 2: "—$CH_2$—$(C_{1-12})_p$—$CONR^{31}R^{32}$" should read "—$CH_2$—$(CH_2)_p$—$CONR^{31}R^{32}$"
Column 118, line 43: "—$CF_3$, hydroxy," should read "—$CF_3$, —$OCF_3$, hydroxy,"
Column 119, line 58: "—$CF_3$, hydroxy," should read "—$CF_3$, —$OCF_3$, hydroxy,"
Column 119, line 66: "—$CF_3$, hydroxy," should read "—$CF_3$, —$OCF_3$, hydroxy,"
Column 120, line 3-4: "—$CF_3$, hydroxy," should read "—$CF_3$, —$OCF_3$, hydroxy,"
Column 120, line 23: "thienyl —$CH_2$" should read "thienyl—$CH_2$"
Column 122, line 42: "—$CF_3$, hydroxy," should read "—$CF_3$, —$OCF_3$, hydroxy,"
Column 122, line 47: "aryl —CH=CH—" should read "aryl—CH=CH—"
Column 123, line 33: "—$CF_3$, hydroxy," should read "—$CF_3$, —$OCF_3$, hydroxy,"
Column 126, line 59: "—$CONR^{31}R^{32}$;" should read "—O—$CH_2$—$CONR^{31}R^{32}$;"
Column 129, line 59: "or phenyl-$C_{1-12}$—$CH_2$—, wherein" should read "or phenyl-$CH_2$—$CH_2$—, wherein"
Column 129, line 65: "A method of preventing of treating" should read "A method of treating"
Column 131, line 56: "—$CF_3$, hydroxy," should read "—$CF_3$, —$OCF_3$, hydroxy,"
Column 134, line 20: "carboxyl, hydroxy-$C_{1-4}$-" should read "carboxyl, hydroxy-$C_{1-5}$-"

Signed and Sealed this
Twenty-fourth Day of July, 2012

David J. Kappos
*Director of the United States Patent and Trademark Office*